(12) United States Patent
Blainey et al.

(10) Patent No.: US 10,816,547 B2
(45) Date of Patent: Oct. 27, 2020

(54) ARTIFICIAL TRANSCRIPTION FACTORS COMPRISING A SLIDING DOMAIN AND USES THEREOF

(71) Applicants: THE BROAD INSTITUTE, INC., Cambridge, MA (US); MASSACHUSETTS INSTITUTE OF TECHNOLOGY, Cambridge, MA (US)

(72) Inventors: Paul Blainey, Cambridge, MA (US); Anthony Kulesa, Boston, MA (US); Kan Xiong, Cambridge, MA (US)

(73) Assignees: THE BROAD INSTITUTE, INC., Cambridge, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 180 days.

(21) Appl. No.: 15/099,371

(22) Filed: Apr. 14, 2016

(65) Prior Publication Data

US 2016/0243251 A1 Aug. 25, 2016

Related U.S. Application Data

(63) Continuation-in-part of application No. PCT/US2014/060438, filed on Oct. 14, 2014.

(60) Provisional application No. 61/890,758, filed on Oct. 14, 2013.

(51) Int. Cl.
| | |
|---|---|
| *G01N 33/569* | (2006.01) |
| *C07K 14/47* | (2006.01) |
| *C07K 14/00* | (2006.01) |
| *A61K 47/64* | (2017.01) |
| *A61K 47/54* | (2017.01) |
| *A61K 31/4375* | (2006.01) |

(52) U.S. Cl.
CPC ... *G01N 33/56966* (2013.01); *A61K 31/4375* (2013.01); *A61K 47/549* (2017.08); *A61K 47/64* (2017.08); *A61K 47/645* (2017.08); *C07K 14/00* (2013.01); *C07K 14/4705* (2013.01); *C07K 2319/01* (2013.01); *C07K 2319/80* (2013.01); *G01N 2800/00* (2013.01)

(58) Field of Classification Search
None
See application file for complete search history.

(56) References Cited

U.S. PATENT DOCUMENTS

| 5,783,384 A * | 7/1998 | Verdine | C07K 1/22 435/6.14 |
|---|---|---|---|
| 2016/0243251 A1 * | 8/2016 | Blainey | C07K 14/00 |

FOREIGN PATENT DOCUMENTS

| EP | 1 097 993 | 5/2001 |
|---|---|---|
| WO | 2014012090 | 1/2014 |

OTHER PUBLICATIONS

International Search Report dated Feb. 20, 2015, which issued during prosecution of PCT/US2014/060438.
Tafvizi et al. "Tumor Suppressor p53 Slides on DNA with Low Friction and High Stability" Biophysical Journal: Biophysical Letters 2008, 95(1):1-3. DOI:10.1529/biophysj.108.13.122.
Zhao et al. "Intracellular Delivery of Artificial Transcription Factors Fused to the Protein Transduction Domain of HIV-1 Tat" Protein Expression and Purification 2013, 90(1):27-33. DOI: 10.1016/j.pep. 2013.04.2007.
Astriab-Fisher et al. "Antisense Inhibition of P-glycoprotein Expression Using Peptide-Oligonucleotide Conjugates" Biochemical Pharmacology 2000, 60(1):83-90. DOI: 10.1016/S0006-2952(00)00310-5.
Blainey et al. "Regulation of a Viral Proteinase by a Peptide and DNA in One-Dimensional Space IV: Viral Proteinase Slides Along DNA to Locate and Process its Substrates" Journal of Biological Chemistry 2013, 288(3):2092-2102. DOI: 10.1074/JBC.M112. 407460.
Tafvizi et al. "A Single-Molecule Characterization of p53 Search on DNA" Proceedings of the National Academy of Sciences, 2011, 108(2):563-568. DOI: 10.1073/pnas.1016020107.
PCT Written Opinion of the International Searching Authority dated Apr. 28, 2016 for PCT/US2014/060438.

* cited by examiner

*Primary Examiner* — Maury A Audet
(74) *Attorney, Agent, or Firm* — Burns & Levinson LLP; Christopher R. Cowles

(57) ABSTRACT

The present invention relates to compositions which may comprise a non-naturally occurring or engineered artificial transcription factor, wherein the transcription factor may comprise a sequence specific DNA binding domain, a sliding domain, and one or more linkers, wherein the DNA binding domain and the sliding domain are operably connected by the one or more linkers, and uses thereof. Methods involving the use of a non-naturally occurring or engineered artificial transcription factors and pharmaceutical compositions, methods for treating cancer, a degenerative disease, a genetic disease or an infectious disease as well as diagnostic methods are also contemplated by the present invention.

32 Claims, 20 Drawing Sheets

Specification includes a Sequence Listing.

- Non-specific binding rate
- Non-specific dissociation rate
- 1-D Diffusivity
- Linker flexibility
- Linker length
- Linker charge
- Domain motion
- Sequence specific binding affinity
- Minor/Major groove
- Stability ing US 10,816,547 B2

```
                              SEQUENCE LISTING

<160> NUMBER OF SEQ ID NOS: 53

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Val Gln Ser Leu Lys Arg Arg Arg Cys Phe
1               5                   10

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Arg Arg Arg
1

<210> SEQ ID NO 3
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Arg Ala Arg Asn Thr Glu Ala Ala Arg Arg Ser Arg Ala Arg Lys
1               5                   10                  15

Gly Gly Cys Gly Lys Arg Arg Arg
            20

<210> SEQ ID NO 4
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Arg Ala Arg Asn Thr Glu Ala Ala Arg Arg Ser Ser Arg Ala Arg
1               5                   10                  15

Ala Ala Ala Ala Ala Ala Lys Arg Arg Arg
            20                  25

<210> SEQ ID NO 5
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 5

Asn Val Lys Arg Arg Thr His Asn Asn Val Leu Glu Arg Gln Arg Asn
1               5                   10                  15

Glu Leu Lys Arg Ser Phe Phe Ala Leu Arg Asp Gln Gly Lys Arg Arg
            20                  25                  30

Arg

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Val Gln Ser Leu Lys Arg Arg Arg Cys Phe
1               5                   10

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Lys Arg Arg Arg
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<223> OTHER INFORMATION: See specification as filed for detailed
      description of substitutions and preferred embodiments

<400> SEQUENCE: 8

Xaa Lys Arg Arg Arg Cys Xaa
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid
<220> FEATURE:
<223> OTHER INFORMATION: See specification as filed for detailed
      description of substitutions and preferred embodiments
```

```
<400> SEQUENCE: 9

Lys Lys Arg Arg Arg Cys Xaa
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<223> OTHER INFORMATION: See specification as filed for detailed
      description of substitutions and preferred embodiments

<400> SEQUENCE: 10

Xaa Lys Arg Arg Arg Cys Phe
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Lys Arg Arg Arg Cys Phe
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Arg Arg Arg Cys Phe
1               5

<210> SEQ ID NO 13
<211> LENGTH: 13
<212> TYPE: PRT
<213> ORGANISM: Unknown
<220> FEATURE:
<223> OTHER INFORMATION: Description of Unknown: p53
      peptide

<400> SEQUENCE: 13

Ser Thr Ser Arg His Lys Lys Leu Met Phe Lys Thr Glu
1               5                   10

<210> SEQ ID NO 14
<211> LENGTH: 13
<212> TYPE: PRT
<213> ORGANISM: Human immunodeficiency virus

<400> SEQUENCE: 14

Gly Arg Lys Lys Arg Arg Gln Arg Arg Pro Pro Gln
1               5                   10
```

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 15

His His His His His His
1               5

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Lys Arg Ala Arg Asn Thr Glu Ala Ala Arg Arg Ser Arg Ala Arg
1               5                   10                  15

<210> SEQ ID NO 17
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Arg Ala Arg Asn Thr Glu Ala Ala Arg Arg Ser Arg Ala Arg Gly
1               5                   10                  15

Ser Gly Ser Gly Ser Lys Arg Arg Arg
            20                  25

<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Arg Ala Arg Asn Thr Glu Ala Ala Arg Arg Ser Arg Ala Arg Gly
1               5                   10                  15

Ser Gly Ser Gly Ser
            20

<210> SEQ ID NO 19
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asn Val Lys Arg Arg Thr His Asn Val Leu Glu Arg Gln Arg Arg Asn
1               5                   10                  15

Glu Leu Lys Arg Ser Phe Phe Ala Leu Arg Asp Gln
            20                  25

```
<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Arg Ala Arg Asn Thr Glu Ala Ala Arg Arg Ser Ser Arg Ala Arg
1               5                   10                  15

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asn Val Lys Arg Arg Thr His Asn Val Leu Glu Arg Gln Arg Arg Asn
1               5                   10                  15

Glu

<210> SEQ ID NO 22
<211> LENGTH: 11
<212> TYPE: PRT
<213> ORGANISM: Human immunodeficiency virus

<400> SEQUENCE: 22

Tyr Gly Arg Lys Lys Arg Arg Gln Arg Arg Arg
1               5                   10

<210> SEQ ID NO 23
<211> LENGTH: 7
<212> TYPE: PRT
<213> ORGANISM: Simian virus 40

<400> SEQUENCE: 23

Pro Lys Lys Lys Arg Lys Val
1               5

<210> SEQ ID NO 24
<211> LENGTH: 16
<212> TYPE: PRT
<213> ORGANISM: Xenopus sp.
<220> FEATURE:
<221> NAME/KEY: MOD_RES
<222> LOCATION: (3)..(12)
<223> OTHER INFORMATION: Any amino acid

<400> SEQUENCE: 24

Lys Arg Xaa Xaa Xaa Xaa Xaa Xaa Xaa Xaa Xaa Xaa Lys Lys Lys Leu
1               5                   10                  15

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Ile Val His Arg Lys Cys Phe
```

```
<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Phe Arg Arg Cys Gly Leu Arg Gln Val Lys
1               5                   10

<210> SEQ ID NO 27
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Pro Lys Lys Arg Lys Arg Arg Leu Tyr Gly Arg Lys Lys Arg Arg Gln
1               5                   10                  15

Arg Arg Arg

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(6)
<223> OTHER INFORMATION: This sequence may encompass 4-6 residues

<400> SEQUENCE: 28

Ala Ala Ala Ala Ala Ala
1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(6)
<223> OTHER INFORMATION: This sequence may encompass 4-6 residues

<400> SEQUENCE: 29

Gly Gly Gly Gly Gly Gly
1               5

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
```

```
gggcggcgac ctaaaaaaaa aaa                                              23
```

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31

```
gacgactagg acgacgacga ggatgacgac                                       30
```

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term TMR

<400> SEQUENCE: 32

Lys Arg Arg Arg
1

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term TMR

<400> SEQUENCE: 33

Arg Arg Arg Arg
1

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: TMR-Cys
<220> FEATURE:
<223> OTHER INFORMATION: C-term NH2

<400> SEQUENCE: 34

Lys Arg Arg Arg Cys
1               5

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term TMR
<220> FEATURE:
<223> OTHER INFORMATION: C-term NH2

```
<400> SEQUENCE: 35

Lys Arg Arg Arg
1

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: TMR-Cys

<400> SEQUENCE: 36

Cys Lys Lys Lys Lys Lys Lys Lys Lys Lys Lys Lys Lys Lys
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: TMR-Cys

<400> SEQUENCE: 37

Cys Arg Arg Arg Arg Arg Arg Arg Arg Arg Arg Arg Arg Arg
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term TMR

<400> SEQUENCE: 38

Lys Lys Lys Lys Lys Lys Lys Lys Lys Lys Lys Lys Lys
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term TMR

<400> SEQUENCE: 39

Arg Arg Arg Arg Arg Arg Arg Arg Arg Arg Arg Arg Arg
1               5                   10

<210> SEQ ID NO 40
<211> LENGTH: 4
<212> TYPE: PRT
<213> ORGANISM: Artificial Sequence
```

<220> FEATURE:
<223> OTHER INFORMATION: Description of Artificial Sequence: Synthetic
      peptide
<220> FEATURE:
<223> OTHER INFORMATION: N-term TMR
<220> FEATURE:
<223> OTHER INFORMATION: C-term NH2

<400> SEQUENCE: 40

Lys Lys Lys Lys
1

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term TMR
<220> FEATURE:
<223> OTHER INFORMATION: C-term NH2

<400> SEQUENCE: 41

Arg Arg Arg Lys
1

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term TMR
<220> FEATURE:
<223> OTHER INFORMATION: C-term NH2

<400> SEQUENCE: 42

Arg Arg Arg Arg
1

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term TMR-(CH2)5
<220> FEATURE:
<223> OTHER INFORMATION: C-term NH2

<400> SEQUENCE: 43

Lys Arg Arg Arg
1

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term TMR
<220> FEATURE:
<221> NAME/KEY: MOD_RES

```
<222> LOCATION: (1)..(4)
<223> OTHER INFORMATION: L-2-amino-3-guanidinopropionic acid
<220> FEATURE:
<223> OTHER INFORMATION: C-term NH2

<400> SEQUENCE: 44

Xaa Xaa Xaa Xaa
1

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term TMR
<220> FEATURE:
<221> NAME/KEY: MOD_RES
<222> LOCATION: (1)..(4)
<223> OTHER INFORMATION: L-homo-arginine
<220> FEATURE:
<223> OTHER INFORMATION: C-term NH2

<400> SEQUENCE: 45

Arg Arg Arg Arg
1

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term TMR
<220> FEATURE:
<221> NAME/KEY: MOD_RES
<222> LOCATION: (1)..(3)
<223> OTHER INFORMATION: Beta3-Arg
<220> FEATURE:
<221> NAME/KEY: MOD_RES
<222> LOCATION: (4)..(4)
<223> OTHER INFORMATION: Beta3-Lys
<220> FEATURE:
<223> OTHER INFORMATION: C-term NH2

<400> SEQUENCE: 46

Arg Arg Arg Lys
1

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term TMR
<220> FEATURE:
<221> NAME/KEY: MOD_RES
<222> LOCATION: (1)..(1)
<223> OTHER INFORMATION: Beta3-Lys
<220> FEATURE:
<221> NAME/KEY: MOD_RES
<222> LOCATION: (2)..(4)
<223> OTHER INFORMATION: Beta3-Arg
<220> FEATURE:
<223> OTHER INFORMATION: C-term NH2
```

<400> SEQUENCE: 47

Lys Arg Arg Arg
1

<210> SEQ ID NO 48
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term TMR
<220> FEATURE:
<223> OTHER INFORMATION: C-term NH2

<400> SEQUENCE: 48

Lys Arg Arg Arg
1

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term TMR-(CH2)5
<220> FEATURE:
<223> OTHER INFORMATION: C-term NH2

<400> SEQUENCE: 49

Lys Arg Arg Arg
1

<210> SEQ ID NO 50
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Arg Arg Arg
1

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term TMR

<400> SEQUENCE: 51

Lys Arg Arg Arg
1

<210> SEQ ID NO 52
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 52

Lys Lys Lys Lys Lys Lys Lys Lys Lys Lys Lys Lys
1               5                   10

<210> SEQ ID NO 53
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Lys Arg Ala Arg Asn Thr Glu Ala Ala Arg Arg Ser Arg Ala Arg Gly
1               5                   10                  15

Ser Gly Ser Gly Ser Gly Val Gln Ser Leu Lys Arg Arg Arg Cys Phe
            20                  25                  30
```

ARTIFICIAL TRANSCRIPTION FACTORS COMPRISING A SLIDING DOMAIN AND USES THEREOF

RELATED APPLICATIONS AND/OR INCORPORATION BY REFERENCE

This application is a continuation-in-part application of international patent application Serial No. PCT/US2014/060438 filed Oct. 14, 2014, which published as PCT Publication No. WO 2015/057671 on Apr. 23, 2015, which claims benefit of and priority to U.S. provisional patent application Ser. No. 61/890,758 filed Oct. 14, 2013.

Reference is made to international patent application PCT/US13/50451 filed Jul. 15, 2013 which claims priority to and benefit of U.S. provisional patent application Ser. No. 61/671,615 filed Jul. 13, 2012.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Nov. 27, 2017, is named 46783_01_2036_SL.txt and is 14,703 bytes in size.

FIELD OF THE INVENTION

The present invention relates to compositions which may comprise a non-naturally occurring or engineered small molecule transcription factors and uses thereof.

BACKGROUND OF THE INVENTION

Many viral proteins contain several, different domains that function at different steps during a virus infection. This is certainly true of the precursor to protein VI, pVI, and of its proteolytically processed product, protein VI, of adenovirus which are involved both early and late in infection. Early in infection, virus particles engage in a stepwise disassembly program coordinated in time and space during entry into cells leading to the delivery of the viral genome into the nucleus for replication. Protein VI is involved in endosome disruption. Late in infection, new virus particles are assembled and rendered infectious. pVI interacts with DNA to activate the adenovirus proteinase (AVP) and with hexon, the major structural proteins of adenovirus, to escort hexon into the nucleus.

Adenoviruses cause epidemic, endemic or sporadic disease and viremia, and are prevalent in the environment. They also cause fatal infections in immunosuppressed individuals. Adenovirus virions are assembled in part from precursor proteins. Of the 12 major virion proteins, 6 are precursor proteins in the young virion, an assembly intermediate.

Late in an adenovirus infection, the viral proteinase (AVP) becomes activated to process virion precursor proteins used in virus assembly. AVP is activated by pVIc, an 11-amino acid peptide from the C-terminus of the precursor protein pVI.

The high concentration of DNA inside the virion drives all the precursor proteins and AVP onto the DNA by mass action. For AVP-pVIc complexes, the DNA-bound state predominates by at least one hundred thousand-fold over free AVP. This, in combination with the sieving action of the dense DNA, diminishes AVP's effective three-dimensional diffusion constant by at least one million-fold. Given these circumstances, a question is by what mechanism can vital bimolecular associations occur when both enzymes and substrates are essentially irreversibly bound to a fixed matrix, the viral DNA.

A model postulated that AVP-pVIc complexes slide along the viral DNA to locate and process the virion precursor proteins. In infectious wild-type virus, pVIc is covalently attached to AVP, indicating that the AVP-pVIc complex is the form of AVP that processes the virion precursor proteins.

Peptides with rapid sliding activity along DNA have the potential to considerably expand the biochemical repertoire of biological systems and offer the possibility of new regulatory mechanisms based on localization to and transport along regions of the genome. Such mechanisms have the potential to feed back on the cell state in many ways, including the variable quantity of DNA in the cell over the course of the cell cycle, its physical configuration within the cell, and its epigenetic state. The extent to which one-dimensional biochemistry extends beyond nucleic acid metabolism in nature is unknown beyond the initial example Applicants illustrate here in adenovirus. However, based on the discovery of human peptides with sliding activity, the possibility cannot be ignored.

Misregulation of gene transcription is found ubiquitously in disease. In cancer, the overproduction of surface receptors can cause amplification of signals telling the cell to divide. The temporal and spatial expression of genes in the embryo is fundamental to proper development.

Citation or identification of any document in this application is not an admission that such document is available as prior art to the present invention.

SUMMARY OF THE INVENTION

Transcription factors are obvious drug targets, but their large DNA-interaction surface precludes them from traditional targeting with small molecule drugs. Synthetic peptide or polyamide DNA binders present a solution to inhibiting transcription factors.

Transcription factors must find their target in a dense matrix surrounded by competing inhibitors. Biophysical studies of the search process have determined that transcription factors solve this problem by combining both three dimensional and one dimensional (along DNA polymer) search mechanisms, yielding a dramatic speed-up in search kinetics.

While a one dimensional search in a flat potential is efficient, search in the rough potential predicted from physical models of DNA-protein interactions is actually prohibitively slow since proteins become trapped at sites with high sequence similarity to the target (the search-stability paradox). Models predict that transcription factors can avoid kinetic traps by switching between non-specific (fast sliding, low binding) and specific (no/slow sliding, high binding) search modes while still maintaining the speedup from one dimensional search modes originally suggested.

The present invention relates to a non-naturally occurring or engineered artificial transcription factor, wherein the transcription factor may comprise a sequence specific DNA binding domain, a sliding domain, and one or more linkers, wherein the DNA binding domain and the sliding domain (which may be a molecular sled) are operably connected by the one or more linkers.

The sequence specific domain may comprise a transcription factor (such as, for example, GCN4 or cMyc), a Dervan polyamide minor groove binder and/or a bZIP transcription factor DNA binding domain derivative.

In one embodiment, the sliding domain may be a pVIc, a refined pVIc or an alternative sled. The pVIc may have a sequence of GVQSLKRRRCF (SEQ ID NO: 1). The refined pVIc may have a sequence of KRRR (SEQ ID NO: 2). Alternative sleds include, but are not limited to, a p53 C-terminus, HIV tat and/or cationic homopolymers.

In advantageous embodiments, the artificial transcription factor may have a sequence of KRARNTEAARRSRARK-GGC-(G)n-KRRR (SEQ ID NO: 3) (such as but not limited to KRARNTEAARRSSRAR-AAAAAA-KRRR) (SEQ ID NO: 4) or NVKRRTHNNVLERQRNELKRSFFALRDQ-(G)n-KRRR (SEQ ID NO: 5).

In another embodiment, the artificial transcription factor may comprise a synthetic dsDNA binding molecule coupled to (G)n-GVQSLKRRRCF (SEQ ID NO: 6) or (G)n-KRRR (SEQ ID NO: 7).

The molecular sled may comprise a core sequence of amino acids XZ'ZZZ'X'X" wherein X, X' and X" is any amino acid, wherein X, X' or X" are optional Z' is any amino acid and is advantageously lysine (K), arginine (R) or histidine (H), wherein Z' is optional and Z is any basic residue, such as lysine (K), arginine (R) or histidine (H)

A minimum core is ZZ (i.e., about two amino acids long) and a maximum of about 30 amino acids, or a complex having a similar molecular weight is contemplated. Synthetic peptides, fragments of natural proteins, analogs thereof, and/or low molecular weight synthetic molecules with basic functionalities are contemplated in addition to basic amino acids.

Furthermore, the core sequence of amino acids XZ'ZZZ'X'X" may be capable of sliding on a negatively charged polymer track.

In an advantageous embodiment, the X of the core sequence may be lysine (K). In another advantageous embodiment, the X' of the core sequence may be cysteine (C). In another advantageous embodiment, the X" of the core sequence may be phenylalanine (F). In another advantageous embodiment, the core sequence may be XKRRRCX" (SEQ ID NO: 8). In another advantageous embodiment, the core sequence of the core sequence may be KKRRRCX" (SEQ ID NO: 9). In another advantageous embodiment, the core sequence of the core sequence may be XKRRRCF (SEQ ID NO: 10). In another advantageous embodiment, wherein the core sequence of the core sequence may be KKRRRCF (SEQ ID NO: 11). In yet another advantageous embodiment, the core sequence may be KRRRCF (SEQ ID NO: 12).

The linkers of the present invention may be attached with a covalent bond, a non-covalent bond and/or a neutrally charged ionic bond. The linker may also include a disulfide bond.

The linker may have a length of about one to about eighteen Angstroms or about the same length from about one to about twelve amino acids long. In an advantageous embodiment, the linkers may be poly alanine or poly glycine. In this embodiment, the linkers may be about four to about six residues in length.

In another embodiment, the linkers may have at least 4, at least 5, at least 6, at least 10, at least 20, at least 30, at least 40, at least 50, at least 60, at least 70, at least 80, at least 90 up to about 100 linear or straight-chain or branched carbon, nitrogen, oxygen, phosphorous, and/or sulfur atoms.

In another embodiment, the linker may be an organic linker, such as, but not limited to, an amide, carbon-sulfide, ester or ether. In an advantageous embodiment, the linker may be part of the core sequence of the molecular sled. In another embodiment, the linker may be a small component, such as biotin or digoxigenin. In another embodiment, the linker may be a peptide, such as an epitope.

The artificial transcription factor of the present invention may optionally comprise a cargo. The cargo may be linked to either the specific binding domain, the sliding domain and/or the linker. The cargo of the present invention may also encompass the linker and/or the sequence specific DNA binding domain. In an advantageous embodiment, the cargo is a therapeutic agent, such as a small molecule, a nucleic acid, a peptide, a protein or an analog or derivative thereof, or a particle, such as a nanoparticle, bed, organelle or large protein complex. Advantageously, the cargo is labeled.

The present invention also encompasses methods involving the use of the artificial transcription factor. The present invention also involves pharmaceutical compositions, methods for treating cancer, a degenerative disease, a genetic disease or an infectious disease as well as diagnostic methods.

The present invention also encompasses methods for altering phenotype or genotype as well as genomic engineering.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 5B discloses SEQ ID NO: 51.

FIG. 11A depicts the GCN4 helix, KRARNTEAARRSRAR (SEQ ID NO: 16), D+SD*: (12.8±5.5)×10$^6$ bp$^2$s$^{-1}$ and D+SEM*: (12.8±0.6)×10$^6$ bp$^2$s$^{-1}$. FIG. 11B depicts the GCN4 helix-linker-KRRR ('KRRR' disclosed as SEQ ID NO: 2), KRARN-TEAARRSRAR-GSGSGS-KRRR (SEQ ID NO: 17), D+SD: (11.3±4.1)×10$^6$ bp$^2$s$^{-1}$ and D+SEM: (11.3±0.6)×10$^6$ bp$^2$s$^{-1}$. FIG. 11C depicts the GCN4 helix-linker-pVIc, KRARNTEAARRSRAR-GSGSGS-pVIc ('KRARN-TEAARRSRAR-GSGSGS' disclosed as SEQ ID NO: 18), D+SD: (9.6±4.3)×10$^6$ bp$^2$s$^{-1}$ and D+SEM: (9.6±0.7)×10$^6$ bp$^2$s$^{-1}$.

FIG. 12A depicts the cMyc helix, NVKRRTHNVLERQRRNELKRSFFALRDQ (SEQ ID NO: 19), D+SD: (12.8±5.0)×10$^6$ bp$^2$s$^{-1}$ and D+SEM: (12.8±0.3)×10$^6$ bp$^2$s$^{-1}$. FIG. 12B depicts the cMyc helix, NVKRRTHNVLERQRRNELKRSFFALRDQ (SEQ ID NO: 19), D+SD: (12.8±5.0)×10$^6$ bp$^2$s$^{-1}$ and D+SEM: (12.8±0.3)×10$^6$ bp$^2$s$^{-1}$.

FIG. 15 discloses SEQ ID NOS 32, 35, 33, 42, 35, 34, 35, 41, 40, 42, 35 and 43, respectively, in order of appearance.

FIG. 16 discloses SEQ ID NOS 44, 42, 45, 35, 41, 35, 35, 41, 46, 35 and 47, respectively, in order of appearance.

DETAILED DESCRIPTION OF THE INVENTION

Figure 1:
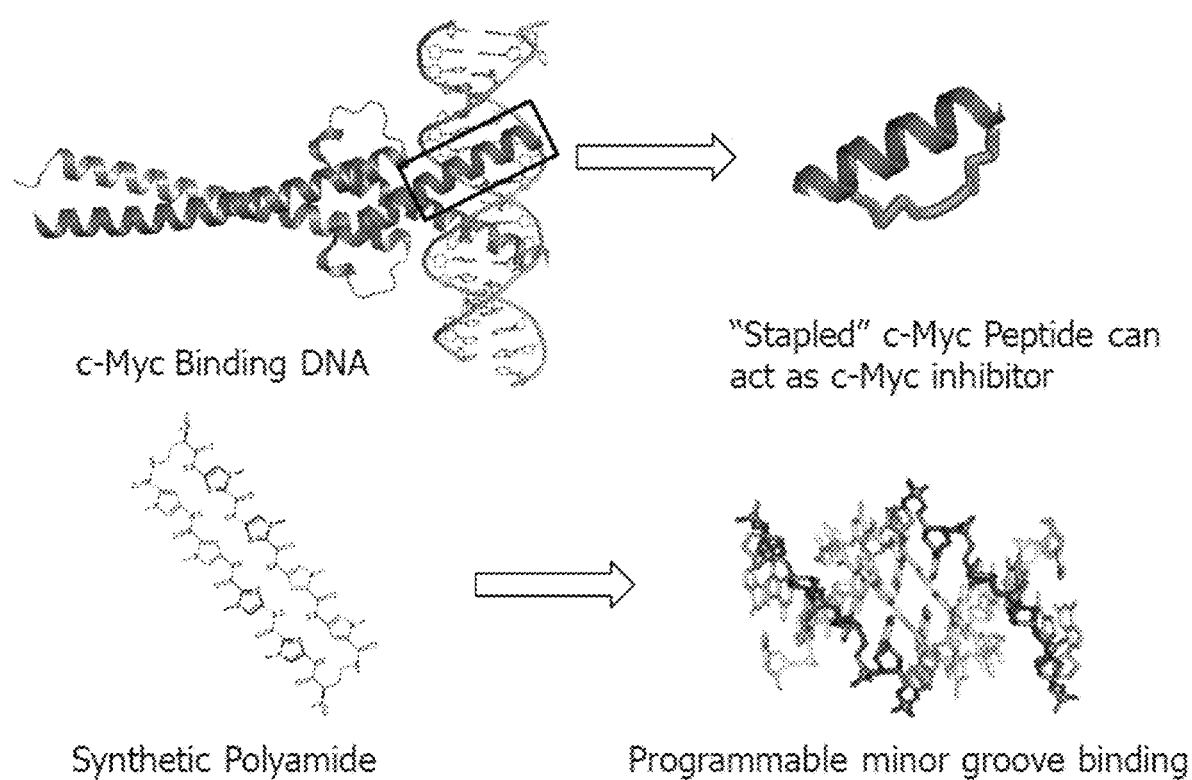
FIG. 1 depicts difficulties of transcription factors as drug targets.
Figure 2:
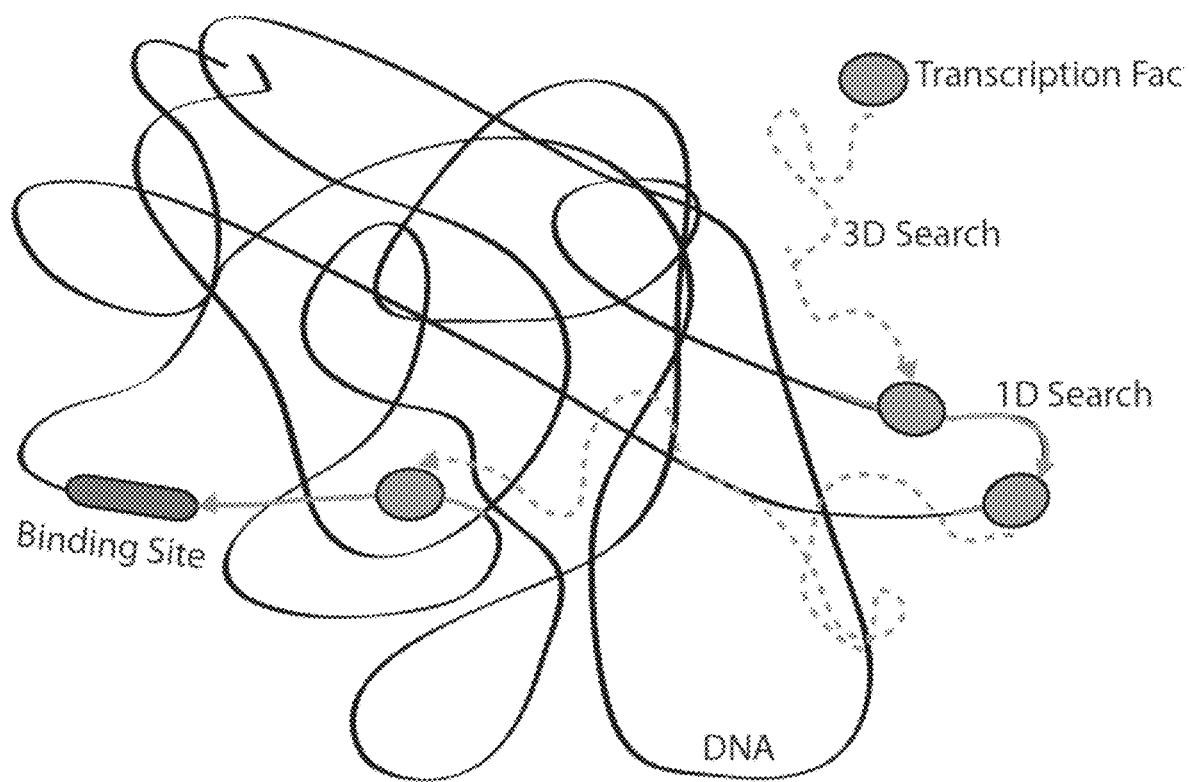
FIG. 2 depicts optimization of the transcription factor search process.
Figure 3A:
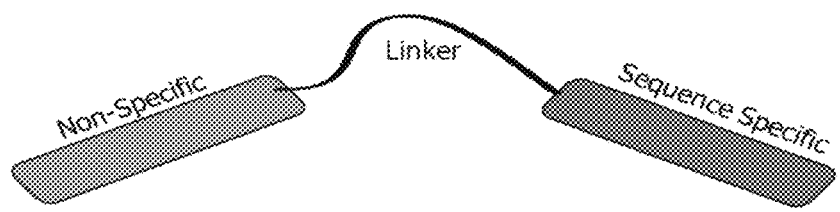
FIGS. 3A and 3B depict high throughput biophysical characterization of modular synthetic transcription factor library.
Figure 3B:
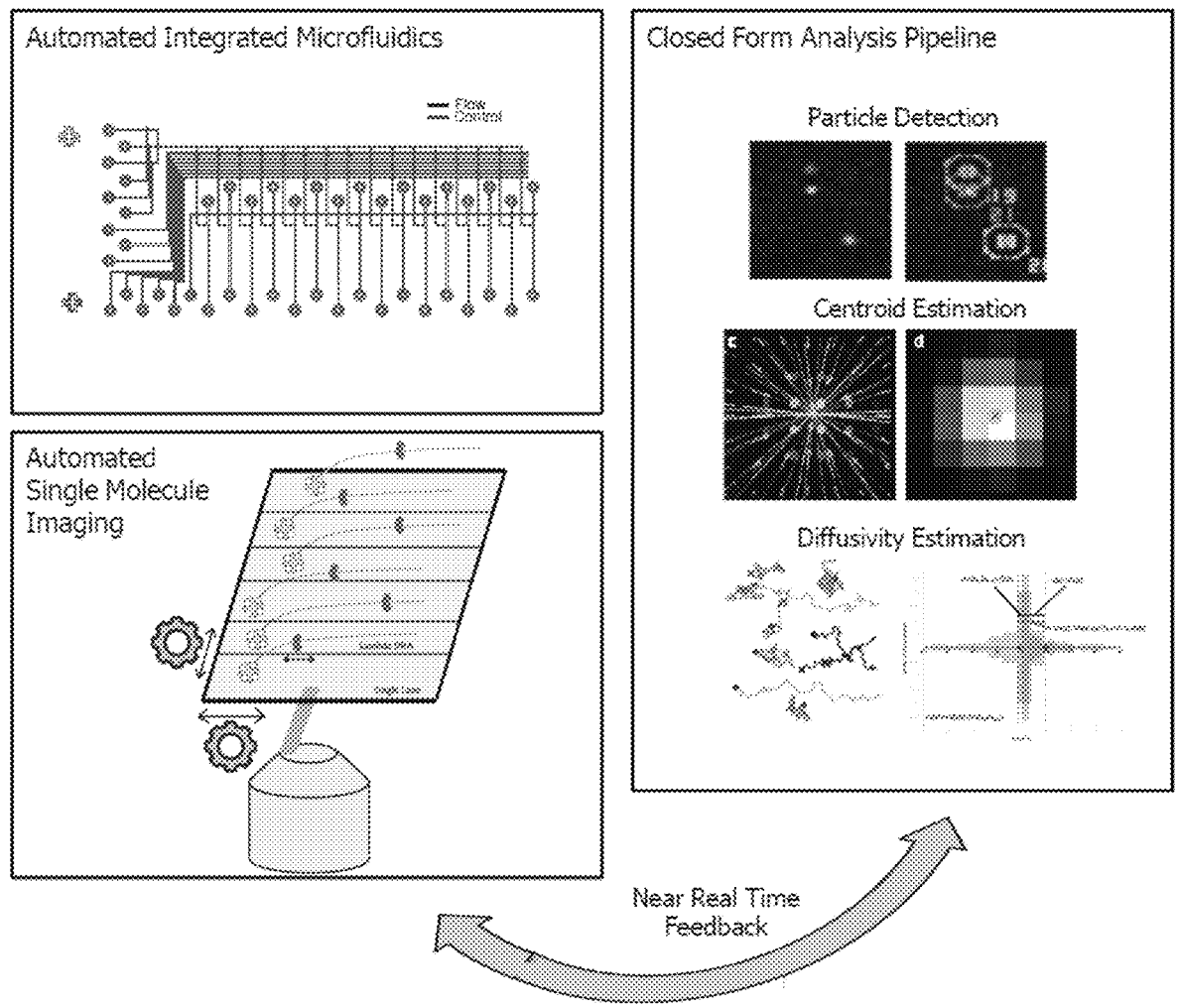
Figure 4:
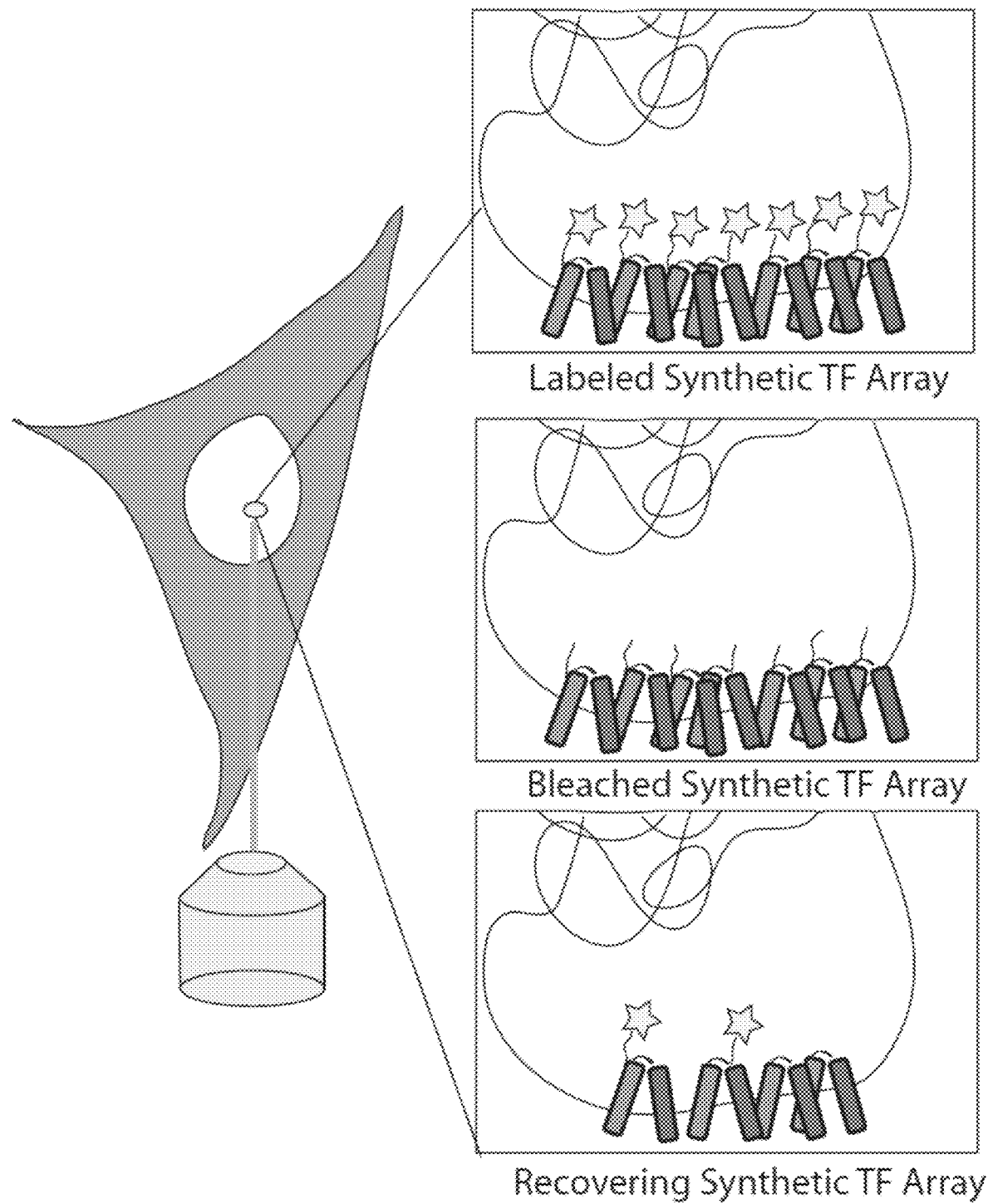
FIG. 4 depicts testing in vivo search dynamics.

The term "nucleic acid" or "nucleic acid sequence" refers to a deoxyribonucleic or ribonucleic oligonucleotide in either single- or double-stranded form. The term encompasses nucleic acids, i.e., oligonucleotides, containing known analogues of natural nucleotides. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant means" encompasses the ligation of nucleic acids having various coding regions or domains or promoter sequences from different sources into an expression cassette or vector for expression of, e.g., inducible or constitutive expression of polypeptide coding sequences in the vectors of invention.

The term "heterologous" when used with reference to a nucleic acid, indicates that the nucleic acid is in a cell or a virus where it is not normally found in nature; or, comprises two or more subsequences that are not found in the same relationship to each other as normally found in nature, or is recombinantly engineered so that its level of expression, or physical relationship to other nucleic acids or other molecules in a cell, or structure, is not normally found in nature. A similar term used in this context is "exogenous". For instance, a heterologous nucleic acid is typically recombinantly produced, having two or more sequences from unrelated genes arranged in a manner not found in nature; e.g., a human gene operably linked to a promoter sequence inserted into an adenovirus-based vector of the invention. As an example, a heterologous nucleic acid of interest can encode an immunogenic gene product, wherein the adenovirus is administered therapeutically or prophylactically as a carrier or drug-vaccine composition. Heterologous sequences can comprise various combinations of promoters and sequences, examples of which are described in detail herein.

A "therapeutic ligand" may be a substance which can bind to a receptor of a target cell with therapeutic effects.

A "therapeutic effect" may be a consequence of a medical treatment of any kind, the results of which are judged by one of skill in the field to be desirable and beneficial. The "therapeutic effect" may be a behavioral or physiologic change which occurs as a response to the medical treatment. The result may be expected, unexpected, or even an unintended consequence of the medical treatment. A "therapeutic effect" may include, for example, a reduction of symptoms in a subject suffering from infection by a pathogen.

A "target cell" may be a cell in which an alteration in its activity can induce a desired result or response.

An "antigen" may be a substance that is recognized by the immune system and induces an immune response.

An "immunogen" may be a substance that elicits an immune response from the immune system.

A "ligand" may be any substance that binds to and forms a complex with a biomolecule to serve a biological purpose. As used herein, "ligand" may also refer to an "antigen" or "immunogen". As used herein "antigen" and "immunogen" are used interchangeably.

As used herein, a "pathogen" may refer to a viral pathogen (e.g., virus) or a bacterial pathogen. "Pathogen" also encompasses "respiratory pathogens".

"Expression" of a gene or nucleic acid encompasses not only cellular gene expression, but also the transcription and translation of nucleic acid(s) in cloning systems and in any other context.

As used herein, a "vector" is a tool that allows or facilitates the transfer of an entity from one environment to another. By way of example, some vectors used in recombinant DNA techniques allow entities, such as a segment of DNA (such as a heterologous DNA segment, such as a heterologous cDNA segment), to be transferred into a target cell. The present invention comprehends recombinant vectors that can include viral vectors, bacterial vectors, protozoan vectors, DNA vectors, or recombinants thereof.

With respect to exogenous DNA for expression in a vector (e.g., encoding an epitope of interest and/or an antigen and/or a therapeutic) and documents providing such exogenous DNA, as well as with respect to the expression of transcription and/or translation factors for enhancing expression of nucleic acid molecules, and as to terms such as "epitope of interest", "therapeutic", "immune response", "immunological response", "protective immune response", "immunological composition", "immunogenic composition", and "vaccine composition", inter alia, reference is made to U.S. Pat. No. 5,990,091 issued Nov. 23, 1999, and WO 98/00166 and WO 99/60164, and the documents cited therein and the documents of record in the prosecution of that patent and those PCT applications; all of which are incorporated herein by reference. Thus, U.S. Pat. No. 5,990,091 and WO 98/00166 and WO 99/60164 and documents cited therein and documents of record in the prosecution of that patent and those PCT applications, and other documents cited herein or otherwise incorporated herein by reference, can be consulted in the practice of this invention; and, all exogenous nucleic acid molecules, promoters, and vectors cited therein can be used in the practice of this invention. In this regard, mention is also made of U.S. Pat. Nos. 6,706,693; 6,716,823; 6,348,450; U.S. patent application Ser. Nos. 10/424,409; 10/052,323; 10/116,963; 10/346,021; and WO 99/08713, published Feb. 25, 1999, from PCT/US98/16739.

As used herein, the terms "drug composition" and "drug", "vaccinal composition", "vaccine", "vaccine composition", "therapeutic composition" and "therapeutic-immunologic composition" cover any composition that induces protection against an antigen or pathogen. In some embodiments, the protection may be due to an inhibition or prevention of infection by a pathogen. In other embodiments, the protection may be induced by an immune response against the antigen(s) of interest, or which efficaciously protects against the antigen; for instance, after administration or injection into the subject, elicits a protective immune response against the targeted antigen or immunogen or provides efficacious protection against the antigen or immunogen expressed from the inventive adenovirus vectors of the invention. The term "pharmaceutical composition" means any composition that is delivered to a subject. In some embodiments, the composition may be delivered to inhibit or prevent infection by a pathogen.

The terms "immunogenic composition" and "immunological composition" and "immunogenic or immunological composition" cover any composition that confers in a subject a therapeutic effect and/or elicits in a subject an immune response against the antigen, immunogen, or pathogen of interest; for instance, after administration into a subject, elicits an immune response against the targeted immunogen or antigen of interest.

An "immunological response" to a composition, vaccine, antigen, immunogen, pathogen or ligand is the development in the host of a cellular and/or antibody-mediated immune response to the composition, vaccine, antigen, immunogen, pathogen or ligand interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display both a rapid (e.g., within <24 hrs.) therapeutic effect and a long-term protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

A "therapeutically effective amount" or an "immunologically effective amount" is an amount or concentration of the recombinant vector encoding the gene of interest, that, when administered to a subject, produces a therapeutic response or an immune response to the gene product of interest.

A "circulating recombinant form" refers to recombinant viruses that have undergone genetic reassortment among two or more subtypes or strains. Other terms used in the context of the present invention is "hybrid form", "recombined form", and "reassortant form".

"Clinical isolates" refer to viruses or microbes isolated from infected subjects in a clinical setting.

"Field isolates" refer to viruses or microbes that are isolated from infected subjects or from the environment.

The term "viral vector" as used herein includes but is not limited to retroviruses, adenoviruses, adeno-associated viruses, alphaviruses, and herpes simplex virus.

This invention solves the challenge of direct modulation of gene activity via small peptides which programmatically bind DNA to inhibit or activate transcription. While many diseases like cancer arise from dysfunction of genetic circuits, current approaches cannot practicably address these problems at the transcriptional level. Additionally, in biological research, synthetically designed genetic circuits and knock-outs/knock-downs are often digital in nature and cannot be gradually tuned to specific activity levels. Past attempts at addressing this issue include large proteins which programmatically target DNA sequences (zinc fingers, TAL effectors, CRISPR) to compete with and tune the binding of endogenous transcription factors, or even editing the genetic content of the genome as in gene therapy. Genome editing/gene therapy are generally not reversible, raising safety concerns. Alternative approaches involve large synthetic molecules, such as polyamides, and triplex forming nucleic acid analogs (PNA). Though effective in vitro, problems in delivery, nuclear uptake, and efficient target binding inhibits their use in vivo. This invention's biomimetic approaches provide an avenue to rationally overcome these issues by integrating the biophysical optimization of these processes in a peptide platform.

The key concept arises from mimicry of the biophysical properties evolved in natural DNA binding proteins that allow them to quickly search DNA for a target sequence. These properties include the multistate binding of DNA where at least one binding state constitutes a search mode in which the protein rapidly but blindly moves along the DNA, and at least one other binding state constitutes an interrogation mode where the target (e.g., a specific DNA sequence) is sampled. Theoretical models predict that by switching between these two modes of search, the protein may rapidly and stably bind its target while avoiding kinetic traps on decoy sequences with high target similarity. Coupling the "molecular sled" technology, a low molecular weight peptide which rapidly slides on DNA, with sequence-specific binding peptides may recapitulate these dual search modes, in a low molecular weight, engineerable, synthetic platform. Nature is known to modulate biochemical logic states and reactivity by controlling dimensionality. A widely recognized example is 3D to 2D Reduction-of-Dimensionality (RD) by targeting factors to cellular membranes, which increases the effective concentrations and accelerate protein-protein interaction. 3D to 1D RD also occurs, for example by targeting proteins to 1D on DNA where one-dimensional diffusion along DNA (including sliding and hopping processes) accelerates DNA target recognition. Previous studies showed that many proteins that drive central dogma processes and DNA metabolism exhibit sequence nonspecific sliding along DNA.[1-8]

Recent work on adenovirus proteins led to the discovery of the first natural protein-protein interactions driven by RD to 1D and the first peptidyl molecular sled, pVIc (GVQSLKRRRCF (SEQ ID NO: 1)).[9,10] Molecular sleds are small basic molecules such as peptides that bind and slide along DNA and can translocate cargo, for example a protein molecule, along DNA. pVIc is capable of sliding by itself as fast as 35.2±0.8 M(bp2/s)11, many times faster than the fastest-sliding proteins.[7,9,10] Molecular sleds are of interest as tools for accelerating and controlling chemical processes in 1D because of their small size and fast diffusion[10,12,13] Molecular sled approaches differ from previous methods utilizing sequence-specific DNA binding proteins[14,15] and strategies based on nucleic acid hybridization[16-18] to co-localize reacting species.

More recently, we began investigating the molecular basis for sliding and observed sliding activity across a wide range of basic polypeptide sequences that implicate mammalian nuclear localization sequences and many cell penetrating peptides as molecular sleds[11]. Here, to advance our understanding of structure-function relationships governing sequence nonspecific DNA binding and sliding activity, we make new chemical modifications to peptidyl molecular sleds.

The prevalence of molecular sled sequences in nature propelled us to ask if any synthetic small molecules are capable of sliding on DNA, specifically: 1) Is there anything special about peptides for sliding? Can non-natural backbone and side chain structures support sliding? 2) Can synthetic small molecules that are structurally unrelated to peptides slide on DNA? Answering these questions will rigorously test our understanding of the structural requirements for molecular sled activity and provide guidelines for designing molecular sleds with properties tailored for particular applications.

Applicants foresee the use of this invention in both research and therapeutic contexts. While knocking out genes (i.e. deleting them from the genome) or knocking down genes with RNAi has allowed the functional studies of many proteins in vivo, this "digital" approach precludes the study and control of many essential pathways. Others have gone to great lengths to achieve titrable control of transcription by a small molecule. Direct titration of the invention would allow the "analog" tuning of expression to more carefully study gene function, or provide a method to study function when knock outs or knock downs are lethal. As a therapeutic, this invention would allow the inhibition of any transcription factor (TFs are commonly identified as high value but 'undruggable' targets). By administering the peptide compounds orally, intravenously, and/or coupling with rational delivery methods, the invention could be used to correct genetic dysfunction in many diseases, such as the overexpression of oncogenic proteins in cancer.

Prototype peptide sequences may include KRARNTEAARRSRARKGGC-(G)n-KRRR (SEQ ID NO: 3), NVKRRTHNNVLERQRNELKRSFFALRDQ-(G)n-KRRR (SEQ ID NO: 5), [Synthetic dsDNA-binding molecule]-(G)n-GVQSLKRRRCF (SEQ ID NO: 6), [Synthetic dsDNA-binding molecule]-(G)n-KRRR (SEQ ID NO: 7).

The present invention contemplates synthesis of a large library of artificial transcription factors and characterizing biophysical properties in vitro.

In an advantageous embodiment, sequence specific domains may include Dervan polyamide minor groove binders and/or bZIP transcription factor DNA binding domain derivatives such as, but not limited to, GCN4 (which may comprise the sequence KRARNTEAARRSSRAR (SEQ ID NO: 20)) or cMyc (which may comprise the sequence NVKRRTHNVLERQRRNE(SEQ ID NO: 21)).

In an advantageous embodiment, sliding domains may be pVIc (which may comprise the sequence GVQSLKRRRCF (SEQ ID NO: 1)), a refined pVIc (which may comprise the sequence KRRR (SEQ ID NO: 2)) or alternative sleds such as, but not limited to, p53 c-terminus, HIV tat, or cationic homopolymers.

Cationic homopolymers include, but are not limited to, a HIV TAT protein transduction domain, a polyamine, a poly(guanidine) or a polyamide.

An example of a polyamine may be N,N'-Bis(3-aminopropyl)-1,3-propanediamine having a structure of:

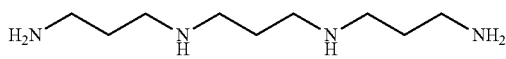

A poly(guanidine) may have a structure of:

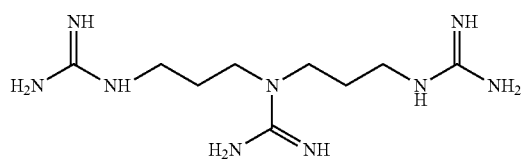 [SMILES: N=C(N)NCCCN(CCCNC(=N)N)C(=N)N]

An example of a polyamide may be distamydin A, which may have a structure of:

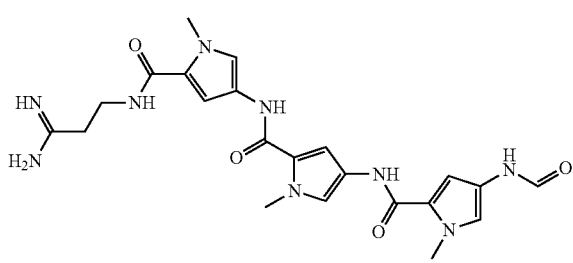 [SMILES: Cn1cc(NC(=O)c2cc(NC(=O)c3cc(NC=O)cn3C)cn2C)cc1C(=O)NCCC(=N)N]

In an advantageous embodiment, the artificial transcription factor of the present invention may comprise the sequence of KRARNTEAARRSSRAR-AAAAAA-KRRR (SEQ ID NO: 4).

In vitro biophysical characterization of search process may be as follows. The search dynamics may be studied in vitro by directly observing fluorescently tagged compounds search DNA and bind their targets with a fluorescence microscope. In an exemplary method, linear fragments of DNA derived from bacteriophage λ (~50 kb) are tethered on a glass coverslip and illuminated with TIRF microscopy. Flowing fluorescently tagged peptides over the coverslip stretches out the DNA hydrodynamically, and the peptides may be directly visualized as they search the DNA. Using computational algorithms, the peptides may be tracked and biophysical parameters such as the rate of diffusive translocation on DNA may be calculated from the estimated trajectories.

Using a custom microscope with integrated microfluidics and automated image capture and analysis, Applicants may characterize the biophysical properties (e.g. diffusivity, off rate, et cetera) of a large library of artificial transcription factor constructs. Other parameters, such as DNA binding affinities, may be measured using standard biochemical assays such as fluorescence polarization.

The in vivo characterization of search process may be as follows. Once the artificial transcription factor library has been characterized in vitro, Applicants may predict and compare how these biophysical properties impact the in vivo search dynamics. To measure the search dynamics in vivo, fluorescently tagged artificial transcription factors may be targeted to a large array of repeats at a specific genetic locus such that when all bound, a fluorescence microscope may visualize them as a punctate fluorescent spot. By photobleaching the spot and observing the recovery of fluorescence, Applicants may estimate both the on and off rates of binding the target sequence. Comparing this data against the in vitro data may help Applicants find the right "engineering space" in which to design the artificial transcription factors.

Mirny L A, Slutsky M, Wunderlich Z, Tafvizi A, Leith J, Kosmrlj A. "How a protein searches for its site on DNA: the mechanism of facilitated diffusion." *J Phys A: Math Theor.* 42, 2009 provides a comprehensive overview of the Mirny model for facilitated diffusion. Covers 1D-3D optimization, speed-stability paradox, and comparison with simulations and experimental results. This is the theoretical grounding for Applicants' rational design of artificial transcription factors, governing the kinetics and thermodynamics needed for efficient, potent molecules.

Slutsky M, Mirny L A. "Kinetics of Protein-DNA Interaction: Facilitated Target Location in Sequence-Dependent Potential." *Biophys J* 87, 2004 is an original paper which details 1D-3D search optimization and the proposed solution to the speed-stability paradox and provides additional theoretical grounding for Applicants' work.

Berg O G, Winter R B, von Hippel P H. "Diffusion-driven mechanisms of protein translocation on nucleic acids. 1. Models and Theory." Provides an original theoretical treatment of facilitated diffusion mechanisms and the effect of the kinetics of genome.

R B Winter, O G Berg, P H von Hippel. "Diffusion-driven mechanisms of protein translocation on nucleic acids 3. The *Escherichia coli* lac repressor-operator interaction: kinetic measurements and conclusions." Provides kinetic measurements of the *E. coli* lac repressor transcription factor show that it may bind its target faster than 3D diffusion would allow. Further experiments demonstrate support for 1D sliding model.

Tafvizi A, Huang F, Fersht A R, Mirny L A, van Oijen A M. "A single-molecule characterization of p53 search on DNA." Provides experimental evidence for a model of p53 sliding on DNA. p53 has both a sliding domain and a sequence-specific domain. Applicants take this as inspiration for the modular design of Applicants' small peptide transcription factors.

Hammer P, Leroy P, Mahmutovi A, Marklund E G, Berg O G, Elf J. "The lac repressor displays facilitated diffusion in living cells." Provides experimental confirmation of sliding occurring in vivo in *E. coli*.

Trauger J W, Baird E E, Dervan P B. "Recognition of DNA by designed ligands at subnanomolar concentrations." *Nature* 382, 1996 and Gottesfeld J M, Neely L, Trauger J W, Baird E E, Dervan P B. "Regulation of gene expression by small molecules." *Nature* 387, 1997 provide a description of Peter Dervan's synthetic polyamide minor groove binders which can be programmed to bind DNA sequences and were shown to inhibit gene expression.

Talanian R V, McKnight C J, Rutkowski R, Kim P S. "Minimum length of sequence-specific DNA binding peptide." *Biochemistry* 31, 1992 pertains to stabilizing a short peptide derived from bZIP transcription factor GCN4 by crafting a disulfide linked dimer and show that it is still able to recognize a specific sequence.

Vazquez M E, Caamano A M, Martinez-Costas J, Casted L, Mascarenas J L. "Design and synthesis of a peptide that binds specific DNA sequences through simultaneous interaction in the major and minor groove." *Angewandte Chemie* 40(24), 2001 use a minor groove binder distamycin (from which Dervin polyamides are derived) and conjugate it to a major groove binding peptide derived from the bZip transcription factor GCN4. They show that this stabilizes the helix and binds DNA.

Zhang F, Cong L, Lodato S, Kosuri S, Church G M, Arlotta P. "Efficient construction of sequence-specific TAL effectors for modulating mammalian transcription." *Nature Biotechnology* 29, 2011 relates to TAL effectors, which are large proteins derived from *Xanthomonas* sp. that can be programmed to bind arbitrary DNA sequences. Zhang et al demonstrate efficient ways of cloning new TALs for any DNA sequence and show that they can modulate transcription of endogenous genes.

Qi L S, Larson M H, Gilber L A, Doudna J A, Weissman J S, Arkin A P, Lim W A. "Repurposing CRISPR as an RNA-guided platform for sequence-specific control of gene expression." *Cell* 152(5), 2013 relates to a CRISPR-Cas complex. The CRISPR-Cas is a large protein-RNA complex which can bind any DNA sequence sufficient to hybridize with the RNA component. Qi et al employ this system to target CRISPR-Cas to arbitrary genetic loci and inhibit transcription.

Novina C D, Sharp P A. "The RNAi revolution." *Nature* 4320, 2004 provides a review on the use of RNAi to modulate translation, as an alternative to Applicants' methods which modulate transcription.

Knauert M P, Glazer P M. "Triplex forming oligonucleotides: sequence-specific tools for gene targeting." reviews triplex forming oligonucleotides (TNO) and peptide nucleic acids (PNAs) to inhibit transcription.

The molecular sled may comprise a core sequence of amino acids XZ'ZZZ'X'X" wherein X, X' and X" is any amino acid, wherein X, X' or X" are optional Z' is any amino acid and is advantageously lysine (K), arginine (R) or histidine (H), wherein Z' is optional and Z is any basic residue, such as lysine (K), arginine (R) or histidine (H)

A minimum core is ZZ (i.e., about two amino acids long) and a maximum of about 30 amino acids, or a complex having a similar molecular weight is contemplated. Synthetic peptides, fragments of natural proteins, analogs thereof, and/or low molecular weight synthetic molecules with basic functionalities are contemplated in addition to basic amino acids.

The core sequence of amino acids may be capable of sliding on a negatively charged polymer track.

In an advantageous embodiment, the X of the core sequence may be lysine (K). In another advantageous embodiment, the X' of the core sequence may be cysteine (C). In another advantageous embodiment, the X" of the core sequence may be phenylalanine (F). In another advantageous embodiment, the core sequence may be XKRRRCX" (SEQ ID NO: 8). In another advantageous embodiment, the core sequence of the core sequence may be KKRRRCX"(SEQ ID NO: 9). In another advantageous embodiment, the core sequence of the core sequence may be XKRRRCF (SEQ ID NO: 10). In another advantageous embodiment, the core sequence of the core sequence may be KKRRRCF (SEQ ID NO: 11). In yet another advantageous embodiment, the core sequence may be KRRRCF (SEQ ID NO: 12).

In one embodiment, X, X' or X" may comprise one or more naturally occurring or non-naturally occurring amino acids. The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The cargo of the present invention may encompass or may be identical or substantially similar to the sequence specific DNA binding domain.

The molecular sled and cargo of the present invention may be capable of penetrating a cell membrane. A classic example is the HIV TAT protein transduction domain, the peptide YGRKKRRQRRR (SEQ ID NO: 22). Such polycationic peptides are cell-penetrating. A subclass of cell penetrating peptides (CPP) with the K-K/R—X-K/R (classical monopartite) motif have additional signaling activity triggering nuclear import.

The molecular sled and cargo of the present invention may further comprise a nuclear localization signal (NLS). NLS is a sequence that has been identified in a variety of species of living organisms and viruses, and is generally a partial amino acid sequence rich in basic amino acids present in a variety of polypeptides that translocate into the nucleus within a cell. For instance, the literature of R. Truant and B. R. Cullen (MOLECULAR AND CELLULAR BIOLOGY, volume 19 (2), 1999, pp. 1210-1217) describes an NLS present in the human immunodeficiency virus (HIV). NLS sequences typically are small, mostly basic, amino acid sequences which can be classified into three general groups: (i) a monopartite NLS exemplified by the SV40 large T antigen NLS (PKKKRKV (SEQ ID NO: 23)); (ii) a bipartite motif consisting of two basic domains separated by a variable number of spacer amino acids and exemplified by the *Xenopus* nucleoplasmin NLS (KRXXXXXXXXXXK-KKL (SEQ ID NO: 24)); and (iii) noncanonical sequences such as M9 of the hnRNP A1 protein, the influenza virus nucleoprotein NLS, and the yeast Gal4 protein NLS (Dingwall and Laskey, Trends Biochem Sci 16:478-481, 1991).

The steps involved in the import mechanism of proteins into eukaryotic nuclei have been elucidated (Nigg, E. A., Nature, 386:779-87, 1997; Gorlich, D., EMBO J., 17:2721-7, 1998). To be transported, the NLS sequence is recognized by members of the importin family of proteins (also referred to as karyopherins), which then act as carriers to transport the substrate protein across the NPC. Inside the nucleus, the importin-substrate complex dissociates, liberating the substrate protein, and the importin carrier ultimately returns to the cytoplasm. The small GTPase Ran plays a pivotal role in this process by promoting, in its GTP-bound form, the dissociation of the import complex and the subsequent recycling of the importin carrier.

The invention contemplates any linker capable of connecting a molecular sled of the present invention with a molecular cargo.

The linkers of the present invention may be attached with a covalent bond, a non-covalent bond and/or a neutrally charged ionic bond. The linker may also include a disulfide bond. In another embodiment, the linkers may have at least 4, at least 5, at least 6, at least 10, at least 20, at least 30, at least 40, at least 50, at least 60, at least 70, at least 80, at least 90 up to about 100 linear or straight-chain or branched carbon, nitrogen, oxygen, phosphorous, and/or sulfur atoms.

The linker may have a length of about one to about eighteen Angstroms or about the same length from about one to about twelve amino acids long. In an advantageous embodiment, the linkers may be poly alanine or poly glycine. In this embodiment, the linkers may be about four to about six residues in length.

In an advantageous embodiment, linkers may be poly alanine (which may be about 4-6 residues in length) (SEQ ID NO: 28) or poly glycine (which may be about 4-6 residues in length) (SEQ ID NO: 29).

In an advantageous embodiment, the linker may be poly (ethylene glycol).

In another advantageous embodiment, the linker may be

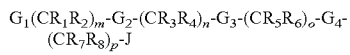

wherein $G_1$, $G_2$, $G_3$, and $G_4$ are each, independently, bifunctional groups selected from

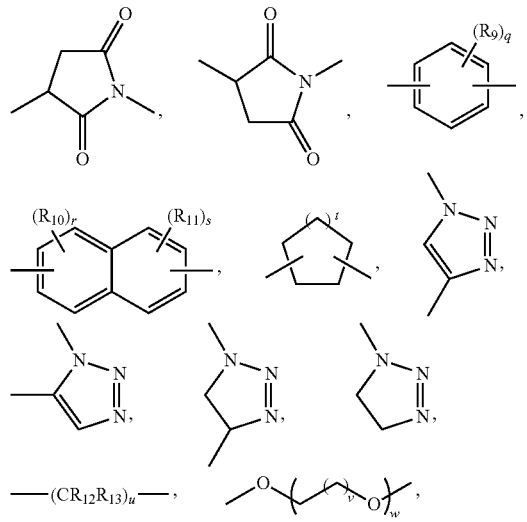

—(C=O)NR$_{14}$—, —NR$_{15}$(C=O), —O—, —O—O—, —O(C=O)—, —O(C=O)O—, —(C=O)O—, —(C=O)—, —P—, —O(PO$_2$)O—, —(PO)—, O(P—NR$_{16}$R$_{17}$)O—, —S—, —S—S—, —O(SO$_2$), —O(SO$_2$)O—, —(SO$_2$)O—, —(SO$_2$)—, —(SO)—, —(SO$_2$)NR$_{20}$—, —NR$_{21}$(SO$_2$)—, —NR$_{22}$—, a peptide, an oligonucleotide, and a combination thereof;

J is a capping group selected from —H, —OR$_{23}$, —NR$_{24}$R$_{25}$, —SR$_{26}$, —(C=O)NR$_{27}$R$_{28}$, —(C=O)OR$_{29}$, a peptide, an oligonucleotide, biotin or a derivative thereof, and digoxigenin or a derivative thereof; or J is a bifunctional group selected from

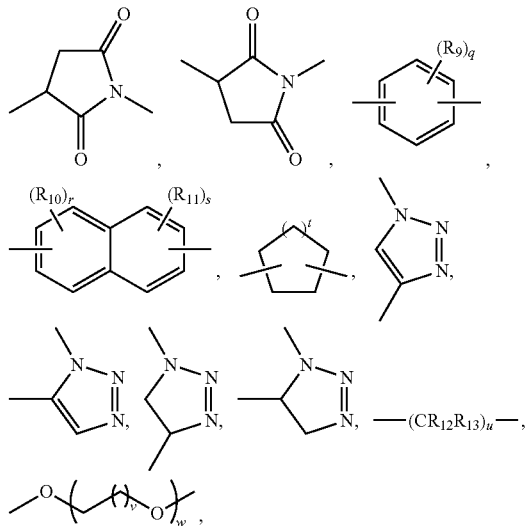

—(C=O)NR$_{14}$—, —NR$_{15}$(C=O), —O—, —O—O—, —O(C=O)—, —O(C=O)O—, —(C=O)O—, —(C=O)—, —P—, —O(PO$_2$)O—, —(PO)—, O(P—NR$_{16}$R$_{17}$)O—, —S—, —S—S—, —O(SO$_2$), —O(SO$_2$) O—, —(SO$_2$)O—, —(SO$_2$)—, —(SO)—, —(SO$_2$)NR$_{20}$—, —NR$_{21}$(SO$_2$)—, —NR$_{22}$—, a peptide, an oligonucleotide, and a combination thereof;

m, n, o, p, u, v, and w are each, independently, an integer from 0 to 20;

q is an integer from 0 to 4;

r, s, and t are each, independently, an integer from 0 to 3;

$R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, and $R_{22}$, are each, independently, hydrogen, halogen, cyano, nitro, $C_{1-10}$ alkyl, $C_{1-10}$ alkenyl, or $C_{1-10}$ alkynyl; wherein the $C_{1-10}$ alkyl, $C_{1-10}$ alkenyl, or $C_{1-10}$ alkynyl are each optionally substituted by one or more substituents selected from hydroxy, halogen, $C_{1-6}$ alkoxy, amino, and aryl and heteroaryl groups of 5 to 12 ring members.

Other linkers contemplated by the present invention include, but are not limited to, carbon with single and double bonds which encompass alkyl- and alkyne-containing linkers. Other chemical linkages may include aldehyde-amine, activated ester (e.g., NHS ester)-amine, Michael condensations (e.g., sulfahydryl with maleimide), and carboxylic acid-amine coupling (as in peptide synthesis, similar to addition to activated ester), "click" chemistry and coordination reactions (such as IDA with nickel or cobalt).

The linker of the present invention may be synthesized using chemical transformations and methods known to those of ordinary skill in the art. The chemical reactions described herein include using solvents, reagents, catalysts, protecting group and deprotecting group reagents, and certain reaction conditions. Synthetic chemistry transformations and protecting group methodologies (protection and deprotection) useful in synthesizing and/or attaching the linkers to the molecular sleds of the present invention are known in the art and include, for example, those disclosed in Advanced Organic Chemistry, second edition, Part B: Reactions and Synthesis, Carey and Sunberg, Plenum Press, N.Y. (1983); Advanced Organic Chemistry, Reactions, Mechanisms, and Structure, second edition, March, McGraw Hill, N.Y. (1977); and Comprehensive Organic Transformations, A Guide to Functional Group Preparations, second edition, Larock, N.Y. (1999); and reference cited therein. Suitable protection/deprotection methodologies and chemical reagents are further described, for example, in T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995) and subsequent editions thereof.

The linker according to the present invention may be synthesized using chemical transformations and methods known to those of ordinary skill in the art. The linker may comprise bifunctional groups and capping groups. Bifunctional groups are groups that have two valences available for bonding. Capping groups are groups that have one valence available for bonding. Examples of suitable functional groups appending such a bifunctional linker include, but are not limited to,

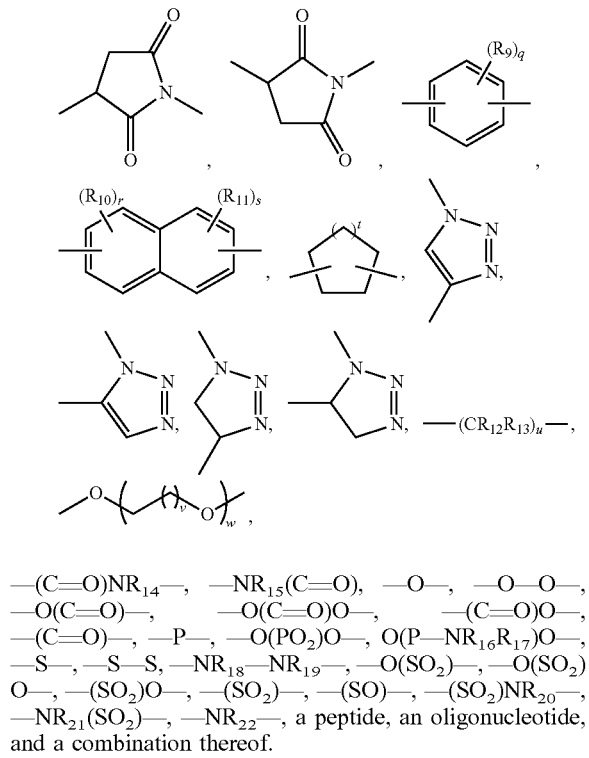

—(C=O)NR$_{14}$—, —NR$_{15}$(C=O), —O—, —O—O—, —O(C=O)—, —O(C=O)O—, —(C=O)O—, —(C=O)—, —P—, —O(PO$_2$)O—, O(P—NR$_{16}$R$_{17}$)O—, —S—, —S—S, —NR$_{18}$—NR$_{19}$—, —O(SO$_2$)—, —O(SO$_2$)O—, —(SO$_2$)O—, —(SO$_2$)—, —(SO)—, —(SO$_2$)NR$_{20}$—, —NR$_{21}$(SO$_2$)—, —NR$_{22}$—, a peptide, an oligonucleotide, and a combination thereof.

Examples of suitable capping groups include, but are not limited to, —H, —OR$_{23}$, —NR$_{24}$R$_{25}$, —SR$_{26}$, —(C=O)NR$_{27}$R$_{28}$, —(C=O)OR$_{29}$, a peptide, an oligonucleotide, biotin or a derivative thereof, and digoxigenin or a derivative thereof. R$_1$, R$_2$, R$_3$, R$_4$, R$_5$, R$_6$, R$_7$, R$_8$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, and R$_{22}$, are each defined herein.

The bifunctional and capping groups described herein may be assembled or synthesized using chemical transformations and methods known to those of ordinary skill in the art.

In another embodiment, the linker may be an organic linker, such as, but not limited to, an amide, carbon-sulfide, ester or ether. In an advantageous embodiment, the linker may be part of the core sequence of the molecular sled. In another embodiment, the linker may be a small component, such as biotin or digoxigenin. The linker may also be bioconjugated.

The present invention also contemplates peptides as linkers. For example, the core of the molecular sled may also be part of the linker.

In an advantageous embodiment, the peptide may be an epitope. Advantageously, the epitope may recognized by a FLAG or HISS antibody.

The molecular cargo may be covalently linked or hydrogen bonded to the one or more linkers. In another embodiment, capture of an endogenous protein/enzyme with an inhibitor, particularly a suicide inhibitor that covalently links with the enzyme, is also contemplated.

The cargo of the present invention may also encompass the linker and/or the sequence specific DNA binding domain. In an advantageous embodiment, the cargo is a therapeutic agent, such as a small molecule, a nucleic acid, a peptide, a protein or an analog or derivative thereof, or a particle, such as a nanoparticle, bed, organelle or large protein complex. Advantageously, the cargo is labeled.

The cargo may be naturally occurring. In an advantageous embodiment, the molecular cargo may be a therapeutic agent, such as a drug. The molecular cargo may be a small molecule, a nucleic acid, a peptide, a protein or an analog or derivative thereof.

If the cargo is a nucleic acid (such as the sequence specific DNA binding domain), the nucleic acid may be a double stranded DNA, single stranded DNA or RNA. Advantageously, the nucleic acid may contain a residue with a 2' O-Me, LNA, or a minor-groove-binding moiety modification.

In another advantageous embodiment, the cargo may be a protein, advantageously, an antibody. The antibody may target a nucleic acid binding protein. In another embodiment, the protein cargo may be a nucleic acid binding protein. Advantageously, the nucleic acid binding protein binds a specific sequence. In a particularly advantageous embodiment, the nucleic acid binding protein may be a DNA gyrase, a transcription activator-like effector (TALE) DNA binding protein, a transcription factor, chromatin remodeling factor, cell cycle promoting or inhibiting factor, epigenetic mark making or binding factor, DNA repair or other DNA metabolizing factor, or a zinc finger binding protein.

In another advantageous embodiment, the protein cargo may be an adenovirus proteinase (AVP), protein VI, pVI or streptavidin.

The cargo may also be modified with one or more gyrase inhibitors, such as but not limited to, Gemifloxacin or Norfloxacin.

The present invention also contemplates molecular capsules. In an advantageous embodiment, the molecular capsule may be a calixarene, cucurbituril, cyclodextrin or pillararene. The cucurbituril may comprise 5, 6, 7, 8 or 10 repeat units. George Church has an example of a capsule made of DNA (see, e.g., Douglas et al., Science 335, 831-834 (2012)).

The present invention also contemplates the cargo as a particle, such as, but not limited to, a nanoparticle, a bead, an organelle or a large protein complex.

In a particular advantageous embodiment, the molecular cargo may comprise a label. Examples of the labeling substance which may be employed include labeling substances known to those skilled in the art, such as fluorescent dyes, enzymes, coenzymes, chemiluminescent substances, and radioactive substances. Specific examples include radio-isotopes (e.g., $^{32}$P, $^{14}$C, $^{125}$I, $^{3}$H, and $^{131}$I), fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase, biotin, and ruthenium. In the case where biotin is employed as a labeling substance, preferably, after addition of a biotin-labeled antibody, streptavidin bound to an enzyme (e.g., peroxidase) is further added.

Advantageously, the label is a fluorescent label. Labeling may be by fluorescent labeling selected from the group of, but not limited to, Cy3, Cy5, Bodipy Texas Red, Bodipy Far Red, *Lucifer* Yellow, Bodipy 630/650-X, Bodipy R6G-X and 5-CR 6G. The fluorescent label may be a fluorescent protein, such as blue fluorescent protein, cyan fluorescent protein, green fluorescent protein, red fluorescent protein, yellow fluorescent protein or any photoconvertible protein. Colormetric labeling, bioluminescent labeling and/or chemiluminescent labeling may further accomplish labeling. Labeling further may include energy transfer between molecules in the hybridization complex by perturbation analysis, quenching, or electron transport between donor and acceptor molecules, the latter of which may be facilitated by double stranded match hybridization complexes. The fluorescent label may be a perylene or a terrylen.

In an advantageous embodiment, the linkers and/or molecular cargo may be light sensitive, wherein the molecular cargo is light-activated and/or light cleaves the one or more linkers to release the molecular cargo. The light-activated molecular cargo may be a major light-harvesting complex (LHCII). In another embodiment, the fluorescent label may induce free radical formation.

The negatively charged polymer track along which the molecular sled is capable of sliding may be a double stranded DNA, single stranded DNA, engineered DNA nanostructures (i.e., "DNA origami"), a nucleosome, chromatin, or other natural or engineered DNA-protein complex, RNA, a ribosome or other natural or engineered ribonucleoprotein complex, a synthetic polymer (e.g., polyglutamic acid) or a natural polymer, organic nanowires or surfaces, inorganic nanowires, negatively charged nano tubes or surfaces, including two dimensional negatively charged surfaces such as glass. The natural polymer may be actin or tubulin. In an advantageous embodiment, the molecular sled may be linked to its cargo binds to the negatively charged polymer track by electrostatic binding. The molecular sleds of the present invention may encircle the DNA topologically by a combination of covalent and/or non-covalent bonds which may further increase the processivity of the molecular sled.

In another embodiment, the molecular sled linked to its cargo is capable of sliding on actin. In this instance, the core amino acids X, Z', X' or X" may be S, I, V, H, R, K, C and/or F. Advantageously, X may be I, Z' may be V, ZZZ may be HRK, X' may be C and/or X" may be F. In a particularly advantageous embodiment, the core sequence may be SIVHRKCF (SEQ ID NO: 25). In another particularly advantageous embodiment, the core sequence may further comprise SGP.

The present invention also contemplates one or more additional sleds, linkers and/or cargos in addition to the molecular sled linked to its cargo. Advantageously, the molecular sled linked to its cargo may react with the one or more additional sleds, linkers and/or cargo. Such a reaction may occur on the polymer track, advantageously on a specific sequence of the polymer track. The polymer track may be DNA and the specific sequence may be a specific genomic locus. The reaction may be gene activation or epigenetic modification. For example, many transcription factors and histone deacetylase enzymes are known to bind to specific sequences. The DNA binding domains of transcription factors and histone deacetylase enzymes may be utilized as part of the molecular sled to bind a specific sequence.

The invention also contemplates the one or more additional sleds, linkers and/or cargo to comprise a PNA brake. The one or more additional sleds, linkers and/or cargo may contain a sled-PNA conjugate. For example, the sled-PNA conjugate may be a chromatin modifying factor.

The present invention also contemplates displaying the molecular sled on an exterior or inner membrane surface. A whole object (such as a vesicle, organelle, or entire cell) may constitute the cargo, or the surface may be used for the concentration of cargos or the recruitment of DNA/chromatin to the membrane surface.

The present invention also contemplates a nucleic acid encoding a molecular sled and a DNA, peptide or protein linker. In an advantageous embodiment, the expression of the sled may be inducible. In an advantageous embodiment, the nucleic acid may further encode the molecular cargo. Advantageously, the molecular cargo is a DNA, peptide or protein. The present invention also contemplates a virus particle which may comprise the above-disclosed nucleic acid. Advantageously, the virus particle is an adenovirus particle.

Also contemplated by the present invention are recombinant vectors and recombinant adenoviruses that can comprise subviral particles from more than one adenovirus serotype. For example, it is known that adenovirus vectors can display an altered tropism for specific tissues or cell types (Havenga, M. J. E. et al., 2002), and therefore, mixing and matching of different adenoviral capsids, i.e., fiber, or penton proteins from various adenoviral serotypes may be advantageous. Modification of the adenoviral capsids, including fiber and penton can result in an adenoviral vector with a tropism that is different from the unmodified adenovirus. Adenovirus vectors that are modified and optimized in their ability to infect target cells can allow for a significant reduction in the therapeutic or prophylactic dose, resulting in reduced local and disseminated toxicity.

Viral vector gene delivery systems are commonly used in gene transfer and gene therapy applications. Different viral vector systems have their own unique advantages and disadvantages. Viral vectors that may be used to express the pathogen-derived ligand of the present invention include but are not limited to adenoviral vectors, adeno-associated viral vectors, alphavirus vectors, herpes simplex viral vectors, and retroviral vectors, described in more detail below.

Additional general features of adenoviruses are such that the biology of the adenovirus is characterized in detail; the adenovirus is not associated with severe human pathology; the adenovirus is extremely efficient in introducing its DNA into the host cell; the adenovirus can infect a wide variety of cells and has a broad host range; the adenovirus can be produced in large quantities with relative ease; and the adenovirus can be rendered replication defective and/or non-replicating by deletions in the early region 1 ("E1") of the viral genome.

Adenovirus is a non-enveloped DNA virus. The genome of adenovirus is a linear double-stranded DNA molecule of approximately 36,000 base pairs ("bp") with a 55-kDa terminal protein covalently bound to the 5'-terminus of each strand. The adenovirus DNA contains identical inverted terminal repeats ("ITRs") of about 100 bp, with the exact length depending on the serotype. The viral origins of replication are located within the ITRs exactly at the genome ends. DNA synthesis occurs in two stages. First, replication proceeds by strand displacement, generating a daughter duplex molecule and a parental displaced strand. The displaced strand is single stranded and can form a "panhandle" intermediate, which allows replication initiation and generation of a daughter duplex molecule. Alternatively, replication may proceed from both ends of the genome simultaneously, obviating the requirement to form the panhandle structure.

During the productive infection cycle, the viral genes are expressed in two phases: the early phase, which is the period up to viral DNA replication, and the late phase, which coincides with the initiation of viral DNA replication. During the early phase, only the early gene products, encoded by regions E1, E2, E3 and E4, are expressed, which carry out a number of functions that prepare the cell for synthesis of viral structural proteins (Berk, A. J., 1986). During the late phase, the late viral gene products are expressed in addition to the early gene products and host cell DNA and protein synthesis are shut off. Consequently, the cell becomes dedicated to the production of viral DNA and of viral structural proteins (Tooze, J., 1981).

The E1 region of adenovirus is the first region of adenovirus expressed after infection of the target cell. This region consists of two transcriptional units, the E1A and E1B genes, both of which are required for oncogenic transformation of primary (embryonal) rodent cultures. The main functions of the E1A gene products are to induce quiescent cells to enter the cell cycle and resume cellular DNA synthesis, and to transcriptionally activate the E1B gene and the other early regions (E2, E3 and E4) of the viral genome. Transfection of primary cells with the E1A gene alone can induce unlimited proliferation (immortalization), but does not result in complete transformation. However, expression of E1A, in most cases, results in induction of programmed cell death (apoptosis), and only occasionally is immortalization obtained (Jochemsen et al., 1987). Co-expression of the E1B gene is required to prevent induction of apoptosis and for complete morphological transformation to occur. In established immortal cell lines, high-level expression of E1A can cause complete transformation in the absence of ElB (Roberts, B. E. et al., 1985).

The E1B encoded proteins assist E1A in redirecting the cellular functions to allow viral replication. The E1B 55 kD and E4 33 kD proteins, which form a complex that is essentially localized in the nucleus, function in inhibiting the synthesis of host proteins and in facilitating the expression of viral genes. Their main influence is to establish selective transport of viral mRNAs from the nucleus to the cytoplasm, concomitantly with the onset of the late phase of infection. The E1B 21 kD protein is important for correct temporal control of the productive infection cycle, thereby preventing premature death of the host cell before the virus life cycle has been completed. Mutant viruses incapable of expressing the E1B 21 kD gene product exhibit a shortened infection cycle that is accompanied by excessive degradation of host cell chromosomal DNA (deg-phenotype) and in an enhanced cytopathic effect (cyt-phenotype; Telling et al., 1994). The deg and cyt phenotypes are suppressed when in addition the E1A gene is mutated, indicating that these phenotypes are a function of E1A (White, E. et al., 1988). Furthermore, the E1B 21 kDa protein slows down the rate by which E1A switches on the other viral genes. It is not yet known by which mechanisms E1B 21 kD quenches these E1A dependent functions.

In contrast to, for example, retroviruses, adenoviruses do not efficiently integrate into the host cell's genome, are able to infect non-dividing cells, and are able to efficiently transfer recombinant genes in vivo (Brody et al., 1994). These features make adenoviruses attractive candidates for in vivo gene transfer of, for example, an antigen or immunogen of interest into cells, tissues or subjects in need thereof.

Adenovirus vectors containing multiple deletions are preferred to both increase the carrying capacity of the vector and reduce the likelihood of recombination to generate replication competent adenovirus (RCA). Where the adenovirus contains multiple deletions, it is not necessary that each of the deletions, if present alone, would result in a replication defective and/or non-replicating adenovirus. As long as one of the deletions renders the adenovirus replication defective or non-replicating, the additional deletions may be included for other purposes, e.g., to increase the carrying capacity of the adenovirus genome for heterologous nucleotide sequences. Preferably, more than one of the deletions prevents the expression of a functional protein and renders the adenovirus replication defective and/or non-replicating and/or attenuated. More preferably, all of the deletions are deletions that would render the adenovirus replication-defective and/or non-replicating and/or attenuated. However, the invention also encompasses adenovirus and adenovirus vectors that are replication competent and/or wild-type, i.e. comprises all of the adenoviral genes necessary for infection and replication in a subject.

Embodiments of the invention employing adenovirus recombinants may include E1-defective or deleted, or E3-defective or deleted, or E4-defective or deleted or adenovirus vectors comprising deletions of E1 and E3, or E1 and E4, or E3 and E4, or E1, E3, and E4 deleted, or the "gutless" adenovirus vector in which all viral genes are deleted. The adenovirus vectors can comprise mutations in E1, E3, or E4 genes, or deletions in these or all adenoviral genes. The E1 mutation raises the safety margin of the vector because E1-defective adenovirus mutants are said to be replication-defective and/or non-replicating in non-permissive cells, and are, at the very least, highly attenuated. The E3 mutation enhances the immunogenicity of the antigen by disrupting the mechanism whereby adenovirus down-regulates MHC class I molecules. The E4 mutation reduces the immunogenicity of the adenovirus vector by suppressing the late gene expression, thus may allow repeated re-vaccination utilizing the same vector. The present invention comprehends adenovirus vectors of any serotype or serogroup that are deleted or mutated in E1, or E3, or E4, or E1 and E3, or E1 and E4. Deletion or mutation of these adenoviral genes result in impaired or substantially complete loss of activity of these proteins.

The "gutless" adenovirus vector is another type of vector in the adenovirus vector family. Its replication requires a helper virus and a special human 293 cell line expressing both Ela and Cre, a condition that does not exist in a natural environment; the vector is deprived of all viral genes, thus the vector as a vaccine carrier is non-immunogenic and may be inoculated multiple times for re-vaccination. The "gutless" adenovirus vector also contains 36 kb space for accommodating antigen(s) or immunogen(s) of interest, thus allowing co-delivery of a large number of antigen(s) or immunogens into cells.

Adeno-associated virus (AAV) is a single-stranded DNA parvovirus which is endogenous to the human population. Although capable of productive infection in cells from a variety of species, AAV is a dependovirus, requiring helper functions from either adenovirus or herpes virus for its own replication. In the absence of helper functions from either of these helper viruses, AAV will infect cells, uncoat in the nucleus, and integrate its genome into the host chromosome, but will not replicate or produce new viral particles.

The genome of AAV has been cloned into bacterial plasmids and is well characterized. The viral genome consists of 4682 bases which include two terminal repeats of 145 bases each. These terminal repeats serve as origins of DNA replication for the virus. Some investigators have also proposed that they have enhancer functions. The rest of the genome is divided into two functional domains. The left portion of the genome codes for the rep functions which regulate viral DNA replication and viral gene expression. The right side of the viral genome contains the cap genes that encode the structural capsid proteins VP1, VP2 and VP3. The proteins encoded by both the rep and cap genes function in trans during productive AAV replication.

AAV is considered an ideal candidate for use as a transducing vector, and it has been used in this manner. Such AAV transducing vectors comprise sufficient cis-acting functions to replicate in the presence of adenovirus or herpes virus helper functions provided in trans. Recombinant AAV (rAAV) have been constructed in a number of laboratories and have been used to carry exogenous genes into cells of a variety of lineages. In these vectors, the AAV cap and/or rep genes are deleted from the viral genome and replaced with a DNA segment of choice. Current vectors can accommodate up to 4300 bases of inserted DNA.

To produce rAAV, plasmids containing the desired viral construct are transfected into adenovirus-infected cells. In addition, a second helper plasmid is cotransfected into these cells to provide the AAV rep and cap genes which are obligatory for replication and packaging of the recombinant viral construct. Under these conditions, the rep and cap proteins of AAV act in trans to stimulate replication and packaging of the rAAV construct. Three days after transfection, rAAV is harvested from the cells along with adenovirus. The contaminating adenovirus is then inactivated by heat treatment.

Herpes Simplex Virus 1 (HSV-1) is an enveloped, double-stranded DNA virus with a genome of 153 kb encoding more than 80 genes. Its wide host range is due to the binding of viral envelope glycoproteins to the extracellular heparin sulphate molecules found in cell membranes (WuDunn & Spear, 1989). Internalization of the virus then requires envelope glycoprotein gD and fibroblast growth factor receptor (Kaner, 1990). HSV is able to infect cells lytically or can establish latency. HSV vectors have been used to infect a wide variety of cell types (Lowenstein, 1994; Huard, 1995; Miyanohara, 1992; Liu, 1996; Goya, 1998).

There are two types of HSV vectors, called the recombinant HSV vectors and the amplicon vectors. Recombinant HSV vectors are generated by the insertion of transcription units directly into the HSV genome, through homologous recombination events. The amplicon vectors are based on plasmids bearing the transcription unit of choice, an origin of replication, and a packaging signal.

HSV vectors have the obvious advantages of a large capacity for insertion of foreign genes, the capacity to establish latency in neurons, a wide host range, and the ability to confer transgene expression to the CNS for up to 18 months (Carpenter & Stevens, 1996).

Retroviruses are enveloped single-stranded RNA viruses, which have been widely used in gene transfer protocols. Retroviruses have a diploid genome of about 7-10 kb, composed of four gene regions termed gag, pro, pol and env. These gene regions encode for structural capsid proteins, viral protease, integrase and viral reverse transcriptase, and envelope glycoproteins, respectively. The genome also has a packaging signal and cis-acting sequences, termed long-terminal repeats (LTRs), at each end, which have a role in transcriptional control and integration.

The most commonly used retroviral vectors are based on the Moloney murine leukaemia virus (Mo-MLV) and have varying cellular tropisms, depending on the receptor binding surface domain of the envelope glycoprotein.

Recombinant retroviral vectors are deleted from all retroviral genes, which are replaced with marker or therapeutic genes, or both. To propagate recombinant retroviruses, it is necessary to provide the viral genes, gag, pol and env in trans.

Lentiviruses are complex retroviruses that have the ability to infect and express their genes in both mitotic and post-mitotic cells. The most commonly known lentivirus is the human immunodeficiency virus (HIV), which uses the envelope glycoproteins of other viruses to target a broad range of cell types.

Alphaviruses, including the prototype Sindbis virus (SIN), Semliki Forest virus (SFV), and Venezuelan equine encephalitis virus (VEE), constitute a group of enveloped viruses containing plus-stranded RNA genomes within icosahedral capsids.

The viral vectors of the present invention are useful for the delivery of nucleic acids expressing antigens or immunogens to cells both in vitro and in vivo. In particular, the inventive vectors can be advantageously employed to deliver or transfer nucleic acids to animal cells, more preferably avian and mammalian cells. Nucleic acids of interest include nucleic acids encoding peptides and proteins, preferably therapeutic (e.g., for medical or veterinary uses) or immunogenic (e.g., for vaccines) peptides or proteins.

Preferably, the codons encoding the antigen or immunogen of interest are "optimized" codons, i.e., the codons are those that appear frequently in, e.g., highly expressed genes in the subject's species, instead of those codons that are frequently used by, for example, an influenza virus. Such codon usage provides for efficient expression of the antigen or immunogen in animal cells. In other embodiments, for example, when the antigen or immunogen of interest is expressed in bacteria, yeast or another expression system, the codon usage pattern is altered to represent the codon bias for highly expressed genes in the organism in which the antigen or immunogen is being expressed. Codon usage patterns are known in the literature for highly expressed genes of many species (e.g., Nakamura et al., 1996; Wang et al., 1998; McEwan et al. 1998).

As a further alternative, the viral vectors can be used to infect a cell in culture to express a desired gene product, e.g., to produce a protein or peptide of interest. Preferably, the protein or peptide is secreted into the medium and can be purified therefrom using routine techniques known in the art. Signal peptide sequences that direct extracellular secretion of proteins are known in the art and nucleotide sequences encoding the same can be operably linked to the nucleotide sequence encoding the peptide or protein of interest by routine techniques known in the art. Alternatively, the cells can be lysed and the expressed recombinant protein can be purified from the cell lysate. Preferably, the cell is an animal cell, more preferably a mammalian cell. Also preferred are cells that are competent for transduction by particular viral vectors of interest. Such cells include PER.C6 cells, 911 cells, and HEK293 cells.

A culture medium for culturing host cells includes a medium commonly used for tissue culture, such as M199-earle base, Eagle MEM (E-MEM), Dulbecco MEM (DMEM), SC-UCM102, UP-SFM (GIBCO BRL), EX-CELL302 (Nichirei), EX-CELL293-S(Nichirei), TFBM-01 (Nichirei), ASF104, among others. Suitable culture media for specific cell types can be found at the American Type Culture Collection (ATCC) or the European Collection of Cell Cultures (ECACC). Culture media can be supplemented with amino acids such as L-glutamine, salts, anti-fungal or anti-bacterial agents such as Fungizone®, penicillin-streptomycin, animal serum, and the like. The cell culture medium can optionally be serum-free.

The present invention also contemplates diagnostic methods for detecting cancer, a degenerative disease, a genetic disease or an infectious disease which may comprise any of the compositions disclosed herein to a suspected cancer cell, genetically diseased cell or infected cell and detecting the molecular sled in the suspected cancer cell or infected cell, thereby detecting cancer, a genetic disease or an infectious disease. The targeting may be to a marker specific to a cancer cell, genetically diseased cell or infected cell, wherein the targeting is by attachment to cargo of a particular size, by attachment via a pH-sensitive cleavable linker, or by a cargo with molecular recognition capability to target a cancer biomarker or a singular cargo or a second, additional cargo.

In particular, the present invention contemplates conjugating the molecular sled of the present invention on an oligomer. Therefore, any polymerase-chain reaction (PCR) diagnostic method may be modified by adding the molecular sled of the present invention to oligomeric primers. Allowing the DNA primers to move along DNA rapidly allows them to arrive at hybridization sites much more rapidly than conventional three-dimensional diffusion allows them to. In this way, the overall reaction time for PCR may be significantly reduced. Moreover, the reversibility of the ternary complex allows improved protocols for purification and immobilization of amplicons. Applicants believe that the PCR process, especially the annealing step, can be speeded up significantly by preparing single stranded (ss) DNA-pVIc conjugates that act as primers in PCR. These conjugates are able to reach their position for DNA strand invasion much faster than the unfunctionalized primers. The performance of oligonucleotide (ODN)-pVIc hybrids is assessed in real-time PCR experiments with a standard molecular beacon that efficiently reports amplicon formation. Special attention is paid to how much the annealing time of primers and primer concentration is reduced. Applicants are well aware of the fact that during the denaturation step the template gets fully or partially separated depending on the sequence composition. The presence of ssDNA should not impair the action of the molecular sled since binding of the oligopeptide was recently also suggested to take place on ss substrates. Assuming duration of 30 seconds for annealing during a standard PCR protocol (30 cycles), Applicants estimate a decrease in the whole PCR procedure by 7 to 10 minutes by employing molecular sled modified primers, which has tremendous economic potential taking into account the widespread use of this technique.

In clinical diagnostic embodiments, the molecular sleds of the present invention may be used in combination with an appropriate means, such as a label, to detect cancer, a degenerative disease, a genetic disease or an infectious disease. Typical methods of detection might utilize, for example, radioactive species, enzyme-active or other marker ligands such as avidin/biotin, which are detectable directly or indirectly. In preferred diagnostic embodiments, one will likely desire to employ an enzyme tag such as alkaline phosphatase or peroxidase rather than radioactive or other reagents that may have undesirable environmental effects. Enzyme tags, for example, often utilize calorimetric indicator substrates that are readily detectable spectrophotometrically, many in the visible wavelength range. Luminescent substrates could also be used for increased sensitivity. However, fluorescent tags may be preferred. The present invention further encompasses a diagnostic composition comprised of the methods of the present invention in the form of a kit. The diagnostic composition may comprise the components as defined hereinabove. The diagnostic composition of the present invention may be used as a kit, inter alia, for carrying out the methods of the present invention, for example diagnostic kits or research tools. Additionally, the kit of the invention may contain suitable means for any other scientific, medical and/or diagnostic purposes. Diagnostic compositions and kits of the present invention may be manufactured by standard procedures that are well known to one of skill in the art. Kits may advantageously include instructions for use and/or admixture of ingredients.

Finally, Applicants contemplate the use of the molecular sled in a number of in vivo applications. First, Applicants display the sled on the bacterial surface to speed up transformation. By allowing plasmid DNA to transiently bind to the outer membrane of E. coli, Applicants increase the uptake of plasmids upon electroporation or salt treatment. Secondly, the molecular sled is presented on the inner cell surface in order to accelerate the production of membrane proteins. By positioning the plasmid at the periphery of the membrane the initial step of membrane protein biogenesis is located at the final destination of the mature protein. In this way, Applicants significantly reduce or even avoid the diffusion of the ribosome nascent chain complex. Thirdly, Applicants couple the sled to antibiotics. By using antibiotics that target DNA-bound proteins (such as gyrase inhibitors), Applicants drastically decrease the time required to find gyrase proteins inside the crowded environment of the cell. An improvement in these kinetics may lead to higher efficacies of this class of antibiotics and to potentially much lower dosages needed for treatment.

Bacterial transformation is a technique widely applied in molecular biology to introduce foreign plasmid DNA into bacteria. In molecular cloning, the ligation of inserts into vectors is an extremely low yielding process and therefore requires high transformation efficiencies for successful gene incorporation. Moreover, in protein evolution a low transfection efficiency is a major bottleneck hampering sampling of large sequence space. The successful uptake of plasmids by transformation of competent cells is in essence determined by a kinetic barrier. Currently, standard protocols rely on having a high concentration of plasmid in the bacterial cultures while electroporation or exposure to calcium chloride transiently permeates the bacterial membrane. One improvement is to locally increase the plasmid concentration by allowing the DNA to bind non-specifically to DNA-binding moieties expressed on the bacterial surface.

Here, Applicants display the molecular sled on the surface of Gram negative bacteria by fusion to outer membrane proteins. Well suited targets include, but are not limited to, Int550 (C-terminal fusion), FhuA (N- and C-terminal fusion) and the AIDA-I autotransporter. Especially the latter has been shown to be suited for surface exposure of passenger peptides and even a stable presentation of functional lactamase on the E. coli outer membrane was achieved. With such a presenting system the DNA is stably localized and kept in a mobile state at the cell surface. These combined features result in enhanced DNA uptake through transiently induced pores in the cell wall compared to wild type cells.

The corresponding transformation efficiency is determined by adding equal amounts of plasmid DNA containing an antibiotic resistance gene to the same number of cells. Subsequent spreading of dilution series on plates supplemented with and without the corresponding antibiotic allow calculating the transformation efficiency.

Instead of presenting the molecular sled to the outside of the cell, displaying the sliding peptide on the inner surface of the cytoplasmic membrane offers exciting opportunities as well. Fusion of the molecular sled to cytoplasmic termini of inner membrane proteins such as, but not limited to, YidC (N- or C terminus), the N-terminus of FtsQ or YddG (N- and C-terminus) results in localization of plasmid or genomic DNA close to the inner cell surface. This situation enables bringing the first step of membrane protein biogenesis, the transcription, closer to the mature protein's final destination. Usually, the translation of mRNA into the membrane protein is stalled as soon as the first hydrophobic transmembrane segment emerges from the ribosome. Subsequently, this complex is transported to the membrane and transferred to the insertion pore (SecYEG). Upon this binding event translation is restarted and the protein is cotranslationally inserted into the membrane. By bringing the first step of membrane protein biogenesis close to the membrane a significant acceleration of protein production is anticipated. The overexpression of membrane proteins in contrast to soluble proteins is still a major obstacle in current biotechnological research and industry.

Another in vivo application is increasing the efficiency of antibiotics with the molecular sled. For that purpose known antimicrobial agents are selected that interfere with the bacterial DNA machinery. The conjugation of the molecular sled with DNA gyrase inhibitors leads to improved drug efficiency. DNA gyrase is an important protein involved in bacterial DNA replication, because it helps to release the strain that arises from unwinding of the ds DNA by helicase. The mode of action of bacterial topoisomerase II inhibitors is the stabilization of the cleavage complexes in an open form with the generation of chromosome breaks. The bacterial DNA gyrases convert into potent cellular toxins leading to cell death. The molecular sled is attached to the amino group of gemifloxacin, a gyrase inhibitor of the 4th generation. The attachment point of the molecular sled is chosen in such a way that it is well separated from the pharmacophore scaffold and therefore should not interfere with drug action. Alternatively, the molecular sled may be coupled to Norfloxacin (2nd generation inhibitor). In both conjugates, the antibiotic activity is strongly increased due to the fact that the 3D diffusion of the drugs is reduced to a one dimensional search process. After the synthesis of the novel conjugate its antimicrobial activity may be tested against E. coli ATCC 25922, which is a standard strain to evaluate the efficiency of antibiotics. Two methods, the Kirby-Bauer Disk Test and the determination of the Minimal Inhibitory Concentration (MIC) are employed for that purpose.

Another example of the application of the molecular sled is potency enhancement of the antibiotics from gyrase and topoisomerase inhibitor classes. Antibiotics from this group form stable complexes with the aforementioned proteins once they cleave bacterial DNA, preventing them from reconnecting DNA strands. Left with chromosomal breaks, bacteria are unable to survive.

However, this class of antibiotics is notorious for its side-effects: phototoxicity, QTc interval prolongation, tendon tear etc. Here Applicants reduce the required dosage of the drug by increasing its potency by chemically attaching a molecular sled to gyrase and topoisomerase inhibitors. Molecules of antibiotic need to find and inactivate their targets that are situated on DNA. Instead of relying only on three dimensional (3D) diffusion, antibiotic with pVIc attached to it slide along bacterial DNA in one dimension (1D). Thus, the search process is much more effective.

One of the antibiotics from gyrase and topoisomerase inhibitor class is gemifloxacin.

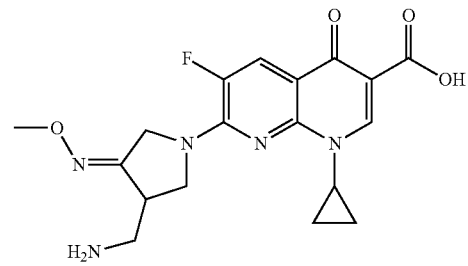 [SMILES: CO/N=C1\CN(c2nc3c(cc2F)c(=O)c(C(=O)O)cn3C2CC2)CC1CN]

Applicants attach pVIc to the primary amine of gemifloxacin because this position is situated far from the pharmacophore of the drug and therefore does not interfere with its action.

The modification is conducted in two steps, the first one being an attachment of a PEG linker

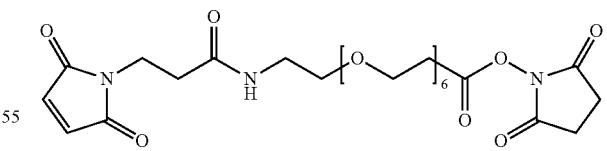

to the primary amine of gemifloxacin by performing a conventional click chemistry of NHS ester to primary amine coupling. The resulting compound GFX-PEG is purified by HPLC.

The second step is a direct coupling of the maleimide group of GFX-PEG to the Cys10' of the pVIc. The final product (gemifloxacin-pVIc) is pur

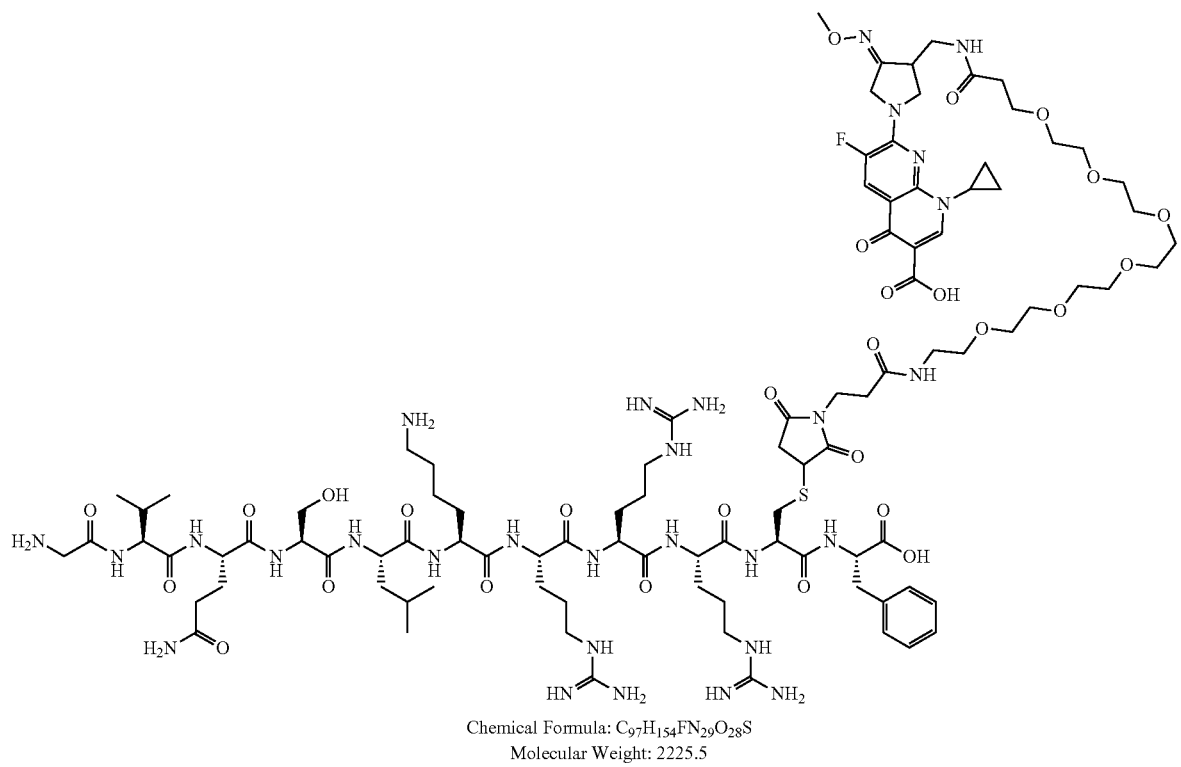 [SMILES: CO/N=C1\CN(c2nc3c(cc2F)c(=O)c(C(=O)O)cn3C2CC2)CC1CNC(=O)CCOCCOCCOCCOCCOCCOCCNC(=O)CCN1C(=O)CC(SC[C@H](NC(=O)[C@H](CCCNC(=N)N)NC(=O)[C@H](CCCNC(=N)N)NC(=O)[C@H](CCCNC(=N)N)NC(=O)[C@H](CCCCN)NC(=O)[C@H](CC(C)C)NC(=O)[C@H](CO)NC(=O)[C@H](CCC(N)=O)NC(=O)[C@@H](NC(=O)CN)C(C)C)C(=O)N[C@@H](Cc2ccccc2)C(=O)O)C1=O]
Chemical Formula: $C_{97}H_{154}FN_{29}O_{28}S$
Molecular Weight: 2225.5

The pVIc peptide influences bacterial uptake of the antibiotic. To have a valid comparison the same modification of gemifloxacin is carried out with a scrambled pVIc peptide with a sequence SFRRCGLRQVK(SEQ ID NO: 26), or other highly basic peptide sequences such as longer, fusions of natural cell penetrating peptides with NLS sequences (for example PKKRKRRLYGRKKRRQRRR(SEQ ID NO: 27) from Johnson et al. 2010, Journal of Investigative Dermatology (2011) 131, 753-761 which do not slide or slide rapidly along DNA. Other basic peptides may not necessarily slide or slide rapidly along DNA (see, e.g., Robillard et al., J. Comb. Chem. 2003, 5, 821-825; Robillard et al., Journal of Inorganic Biochemistry 96 (2003) 331-338 and Wang et al., J. Med. Chem. 2001, 44, 3682-3691) and some other basic peptides do not make it into the nucleus or help with isoform specificity (see, e.g., Canzoneri et al., Bioorganic & Medicinal Chemistry Letters 19 (2009) 6588-6590).

The antimicrobial activity of the three compounds, gemifloxacin-pVIc, gemifloxacin-random pVIc and gemifloxacin is tested against *E. coli* ATCC 25922, which is a standard strain to evaluate the efficiency of antibiotics. Two methods, the Kirby-Bauer Disk Test and the determination of the Minimal Inhibitory Concentration (MIC), are employed for that purpose.

The advantages of this system to speed up antibiotic recognition is to avoid liver delivery passage, avoid gastrointestinal degradation, reduce the IC50 and required concentration to be delivered (such as, but not limited to, about 25%, about 30%, about 35%, about 40%, about 45%, about 50%, about 55%, about 60%, about 65%, about 70% or about 75% reduction of the antibiotic delivered when compared to a conventional antibiotic administration system). Methods of antibiotic administration are known in the art and when coupled with the methods of the present invention, one of skill in the art can adjust the dosage of the antibiotic delivered by the molecular sled of the present invention.

In another embodiment of the present invention, DNA amplification may be accelerated with primers modified with the molecular sleds of the present invention. When PCR primers are modified with the molecular sleds of the invention, the PCR primers find their complementary position on the template more quickly than unmodified primers. Applicants found that primers modified with the molecular sleds of the present invention speed up DNA amplification as compared to DNA primers without a molecular sled. Therefore, the present invention also encompasses methods of accelerating PCR amplification comprising attaching a molecular sled to a PCR primer. A primer-molecular sled may be synthesized by methods known in the art (see, e.g., Ching-Hsuan Tung; M. Jonathan Rudolph; Stanley Stein. Bioconjugate Chem. 1991, 2, 464-465 and Andrew W. Fraley; Bénédicte Pons; Deniz Dalkara; Gerard Nullans; Jean-Paul Behr; Guy Zuber. J. Am. Chem. Soc. 2006, 128, 10763-10771).

The present invention will be further illustrated in the following Examples which are given for illustration purposes only and are not intended to limit the invention in any way.

Example 1

Cell Uptake Experiments. CF1-MEFs (from Global Stem, 6001-G) were seeded at a density of 50,000 cells/well in MEF media to 24-well plates and incubated overnight at 37° C. with 5% CO2. After ~12 hours, the growth media was changed to remove dead cells, and live cells were incubated for another 12 hours. TMR-labeled peptide stock solutions (prepared in RNA-ase free water) were added into each well of 24-well plates, and cells were incubated for another 0.5 hours. Cells were imaged by fluorescence microscopy.

Figure 5A:
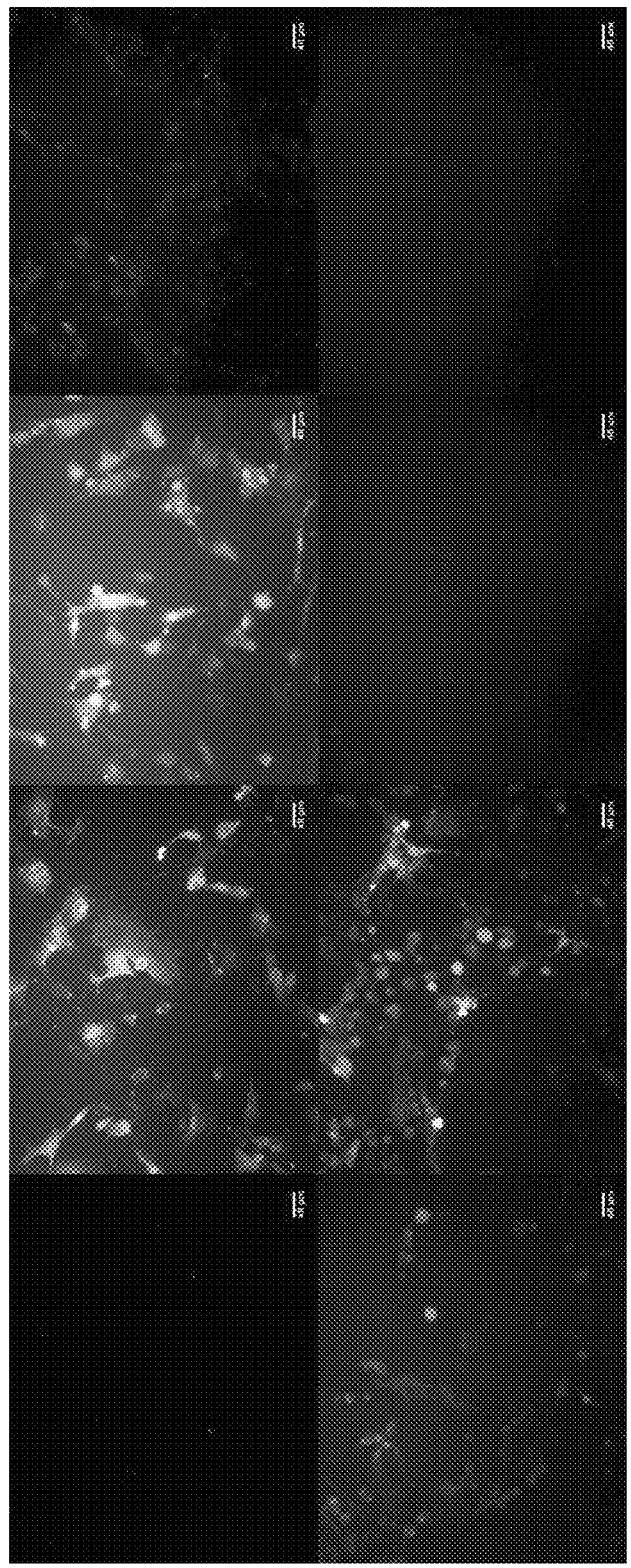
FIG. 5A depicts fluorescence images of CF1-MEFs cells after incubation with TMR-labeled peptides for 0.5 hours.
Figure 5B:
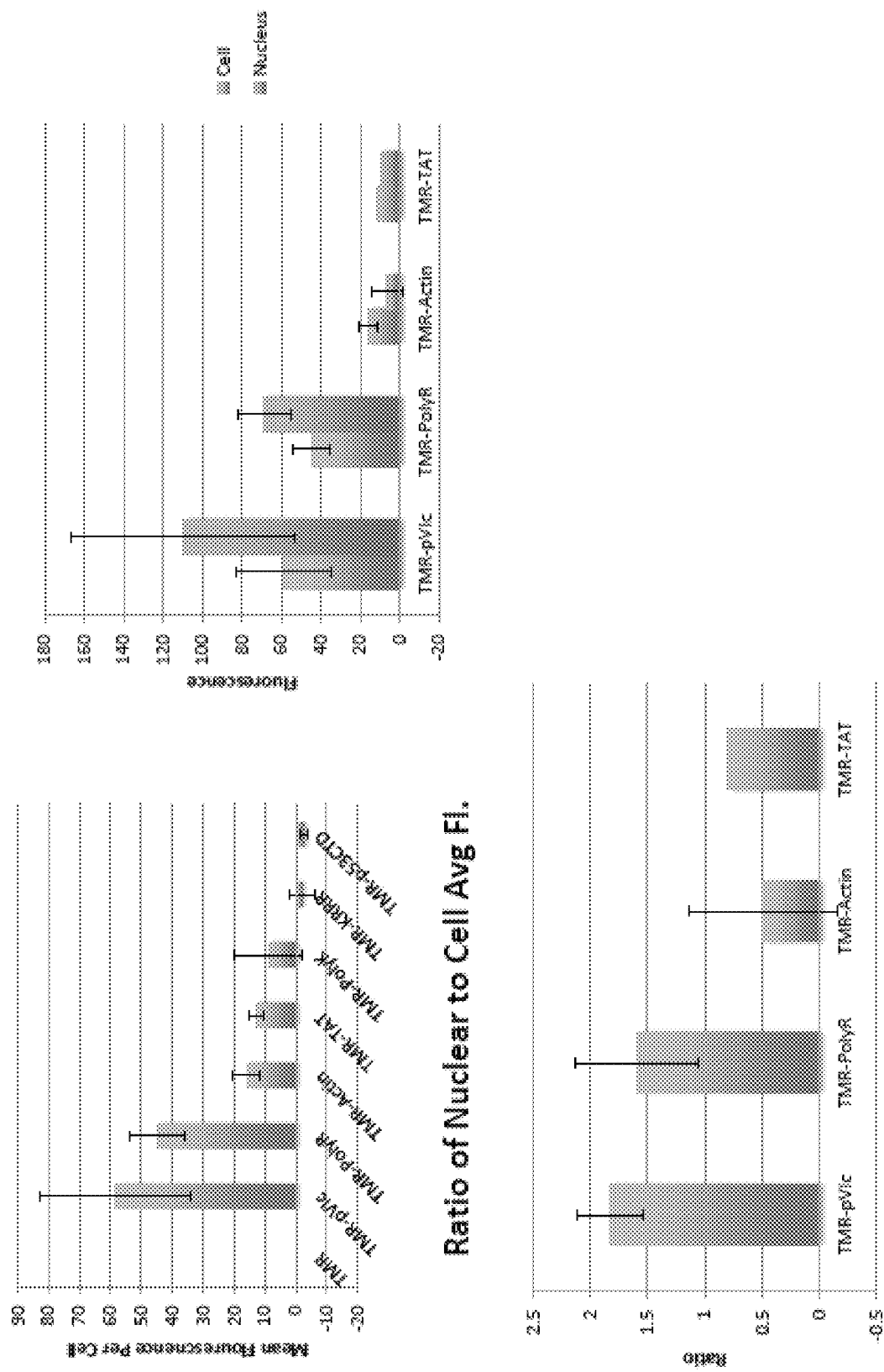
FIG. 5B depicts quantitative analysis results from FIG. 5A images.

FIG. 5A depicts fluorescence images of CF1-MEFs cells after incubation with TMR-labeled peptides for 0.5 hours.

All N-terminus tetramethylrhodamine (TMR)-labeled peptides were purchased from MIT Biopolymer lab (≥75% purity).

The sliding assay, based upon total internal reflection fluorescence microscopy, used phage λ DNA molecules (48,502 base pairs) attached at one end to a glass cover slip surface by a biotin-streptavidin linkage. A flow cell was constructed on top of the cover slip such that when laminar flow is applied, the DNA stretches in the direction of flow and orients itself parallel to and in close proximity to the surface of the cover slip. Evanescent waves from a laser reflecting off the coverslip-buffer interface were used to illuminate a very small volume (~1 pL) with a few hundred nanometers of the glass surface. The interaction of a single, TMR-labeled peptide with DNA was visualized by a CMOS camera (ORCA-Flash 4.0 from Hamamatsu) with 5 ms time-resolution. Despite the optical resolution limit imposed by diffraction, the centroid position of each signal in each frame is determined with sub-diffraction-limited resolution, typically 1-30 nm for bright fluorescent conjugates.

Labeled peptides were infused at concentration of 100-200 pM at rates of 20-50 mL/hour. High flow rates were chosen to drive the longitudinal DNA fluctuation faster than the imaging frame rate. The assay buffer consisted of 10 mM PBS (2 mM NaCl, 0.1 mM β-mercaptoethanol, 0.05 mM EDTA, 5% (v/v) glycerol, 0.01% (v/v) Tween-20, pH 6.8).

Figures 6A, 6B, 6C, 6D, 6E:
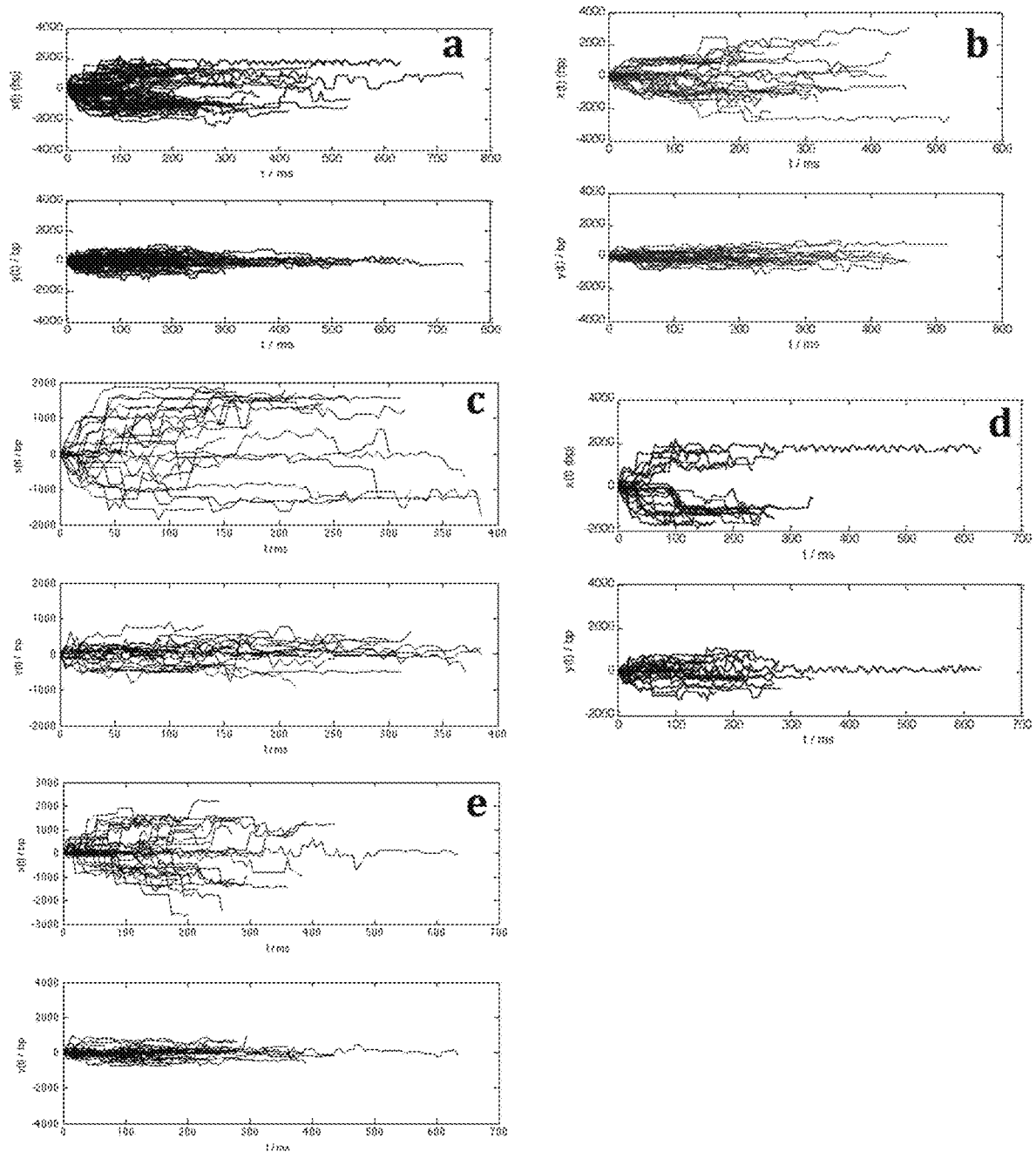
FIGS. 6A-6E depict kymographs of peptides diffusing along λ-DNA (x(t)) and estimated 1D diffusion constants, $D \times 10^{-6}$ (bp)$^2$/s in low salt buffer. a KRRR (SEQ ID NO: 2), D=20.3±7.9; b C-terminal sequence of p53, STSRHKKLM-FKTE (SEQ ID NO: 13), D=17.3±5.3; c Cell penetrating peptide, TAT, GRKKRRQRRRPPQ (SEQ ID NO: 14), D=21.0±7.5; d (K)$_{13}$, (SEQ ID NO: 52) D=17.3±5.3; e HHHHHH (SEQ ID NO: 15), D=14.9±6.9. Motion transverse to the DNA (y(t)) is represented, as a control.

FIG. 6 depicts kymographs of peptides diffusing along λ-DNA (x(t)) and estimated 1D diffusion constants, D x $10^{-6}$ $(bp)^2/s$ in low salt buffer. a KRRR (SEQ ID NO: 2), D=20.3±7.9; b C-terminal sequence of p53, STSRHKKLM-FKTE (SEQ ID NO: 13), D=17.3±5.3; c Cell penetrating peptide, TAT, GRKKRRQRRRPPQ (SEQ ID NO: 14), D=21.0±7.5; d $(K)_{13}$ (SEQ ID NO: 52), D=17.3±5.3; e HHHHHH (SEQ ID NO: 15), D=14.9±6.9. Motion transverse to the DNA (y(t)) is represented, as a control.

Example 2

This Example relates to building a library of peptide sequences (including non-natural sequences) capable of sliding on DNA. This library also relates to the correlation of sliding activity of a complex correlation with that of its individual components. In particular, is there cooperativity or anti-cooperativity.

Systems of interest include, but are not limited to, pVIc-pVIc, pVIc-reverse_pVIc, pVIc-scrambled_pVIc and pVIc-pVIc-pVIc.

Figure 7:
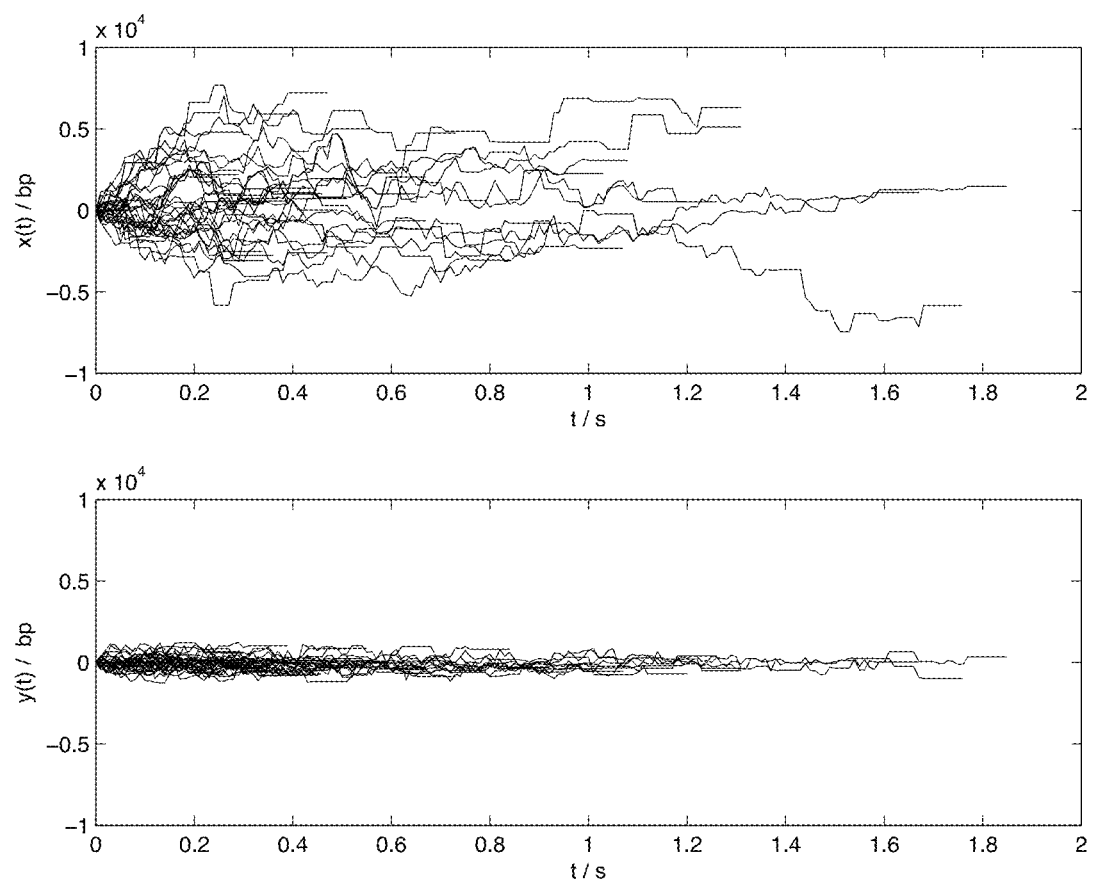
FIG. 7 depicts a kymograph of measured single molecule sliding trajectories and 1D diffusion constant of pVIc-pVIc, D+SD*: (12.5±7.4)×10$^6$ bp$^2$s$^{-1}$ and D+SEM*: (12.5±1.3)× 10$^6$ bp$^2$s$^{-1}$*SD: standard deviation; SEM: standard mean error.

FIG. 7 depicts a kymograph of measured single molecule sliding trajectories and 1D diffusion constant of pVIc-pVIc, D+SD*: (12.5±7.4)×$10^6$ $bp^2s^{-1}$ and D+SEM*: (12.5±1.3)×$10^6$ $bp^2s^{-1}$ *SD: standard deviation; SEM: standard mean error.

Figure 8:
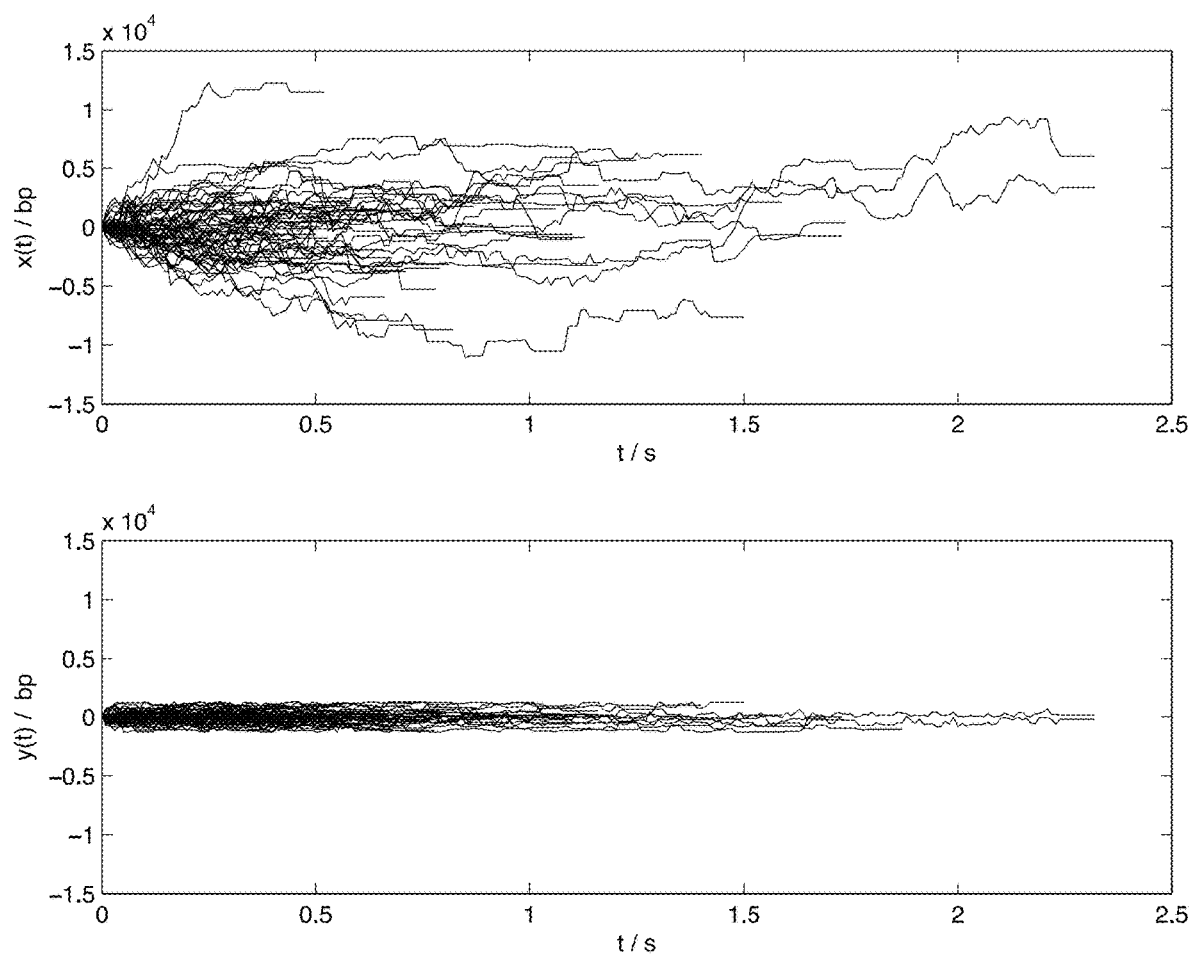
FIG. 8 depicts a kymograph of measured single molecule sliding trajectories and 1D diffusion constant of pVIc-reverse_pVIc, D+SD: (16.7±5.8)×10$^6$ bp$^2$s$^{-1}$ and D+SEM: (16.7±1.1)×10$^6$ bp$^2$s$^{-1}$
Figure 9:
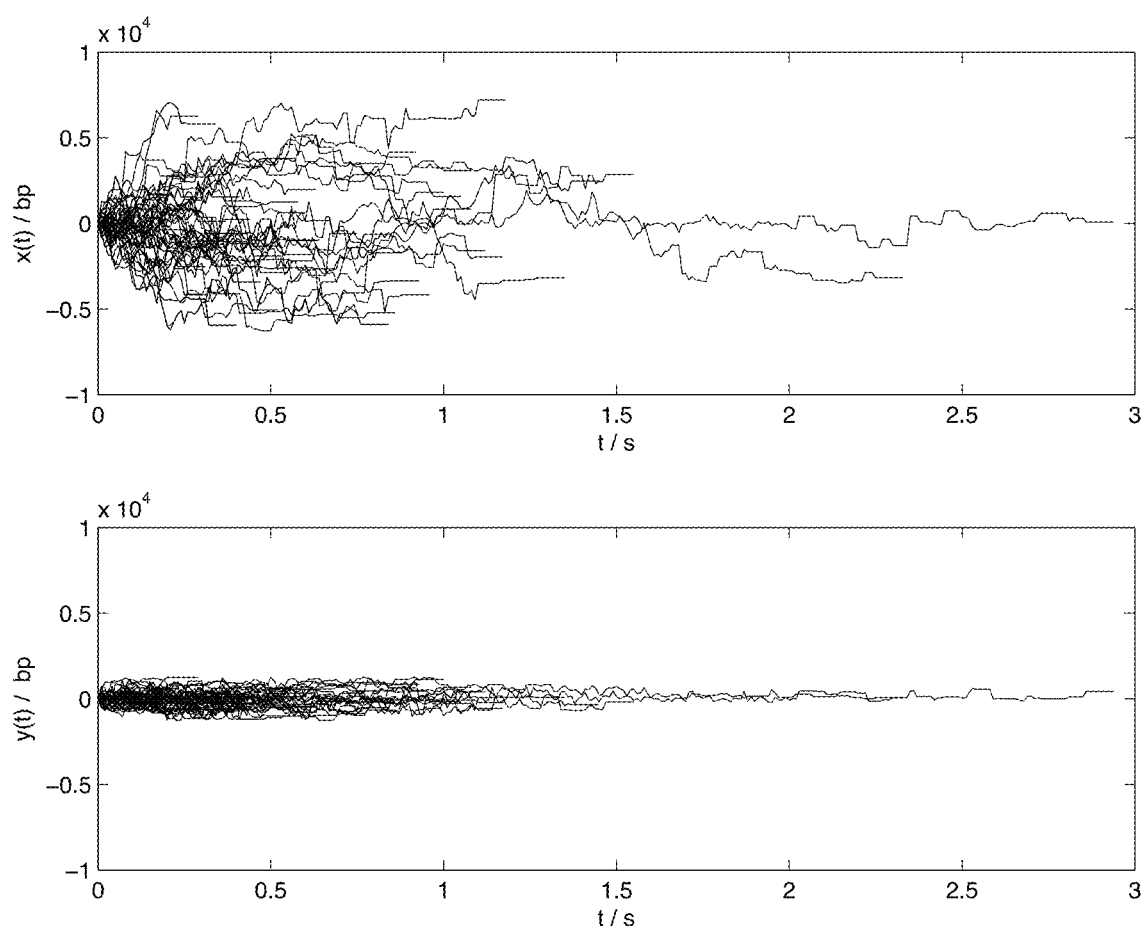
FIG. 9 depicts a kymograph of measured single molecule sliding trajectories and 1D diffusion constant of pVIc-scrambled_pVIc, D+SD: (12.5±5.3)×10$^6$ bp$^2$s$^{-1}$ and D+SEM: (12.5±0.7)×10$^6$ bp$^2$s$^{-1}$
Figure 10:
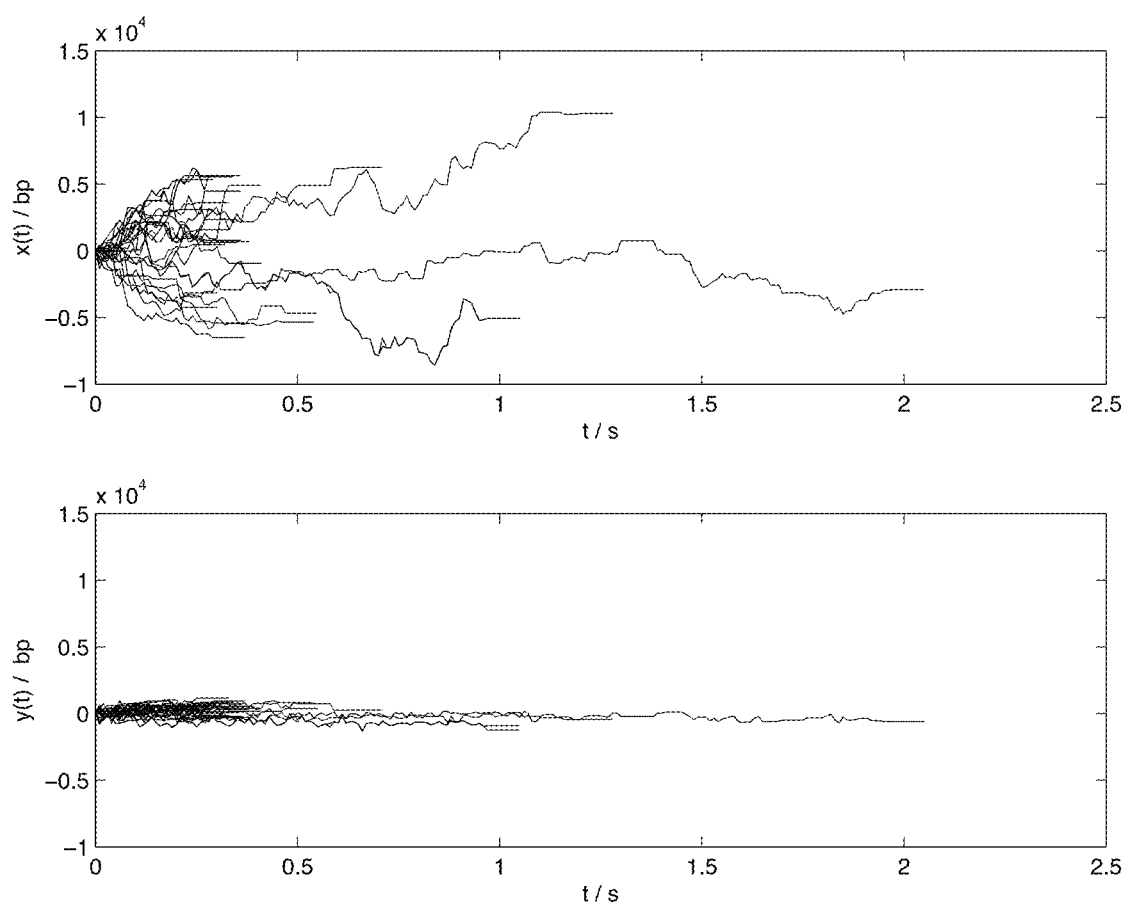
FIG. 10 depicts a kymograph of measured single molecule sliding trajectories and 1D diffusion constant of pVIc-pVIc-pVIc, D+SD: (16.7±5.8)×10$^6$ bp$^2$s$^{-1}$ and D+SEM: (16.7±1.1)×10$^6$ bp$^2$s$^{-1}$

FIG. 8 depicts a kymograph of measured single molecule sliding trajectories and 1D diffusion constant of pVIc-revers_epVIc, D+SD: (16.7±5.8)×$10^6$ $bp^2s^{-1}$ and D+SEM: (16.7±1.1)×$10^6$ $bp^2s^{-1}$ FIG. 9 depicts a kymograph of measured single molecule sliding trajectories and 1D diffusion constant of pVIc-scrambled_pVIc, D+SD: (12.5±5.3)×$10^6$ $bp^2s^{-1}$ and D+SEM: (12.5±0.7)×$10^6$ $bp^2s^{-1}$ FIG. 10 depicts a kymograph of measured single molecule sliding trajectories and 1D diffusion constant of pVIc-pVIc-pVIc, D+SD: (16.7±5.8)×$10^6$ $bp^2s^{-1}$ and D+SEM: (16.7±1.1)×$10^6$ $bp^2s^{-1}$ This Example also relates to fine tuning of sliding activity of a synthetic transcriptional factor on DNA and its target search speed with a peptide slide. Systems of interest include a GCN4 helix and a cMyc helix.

Figure 11A:
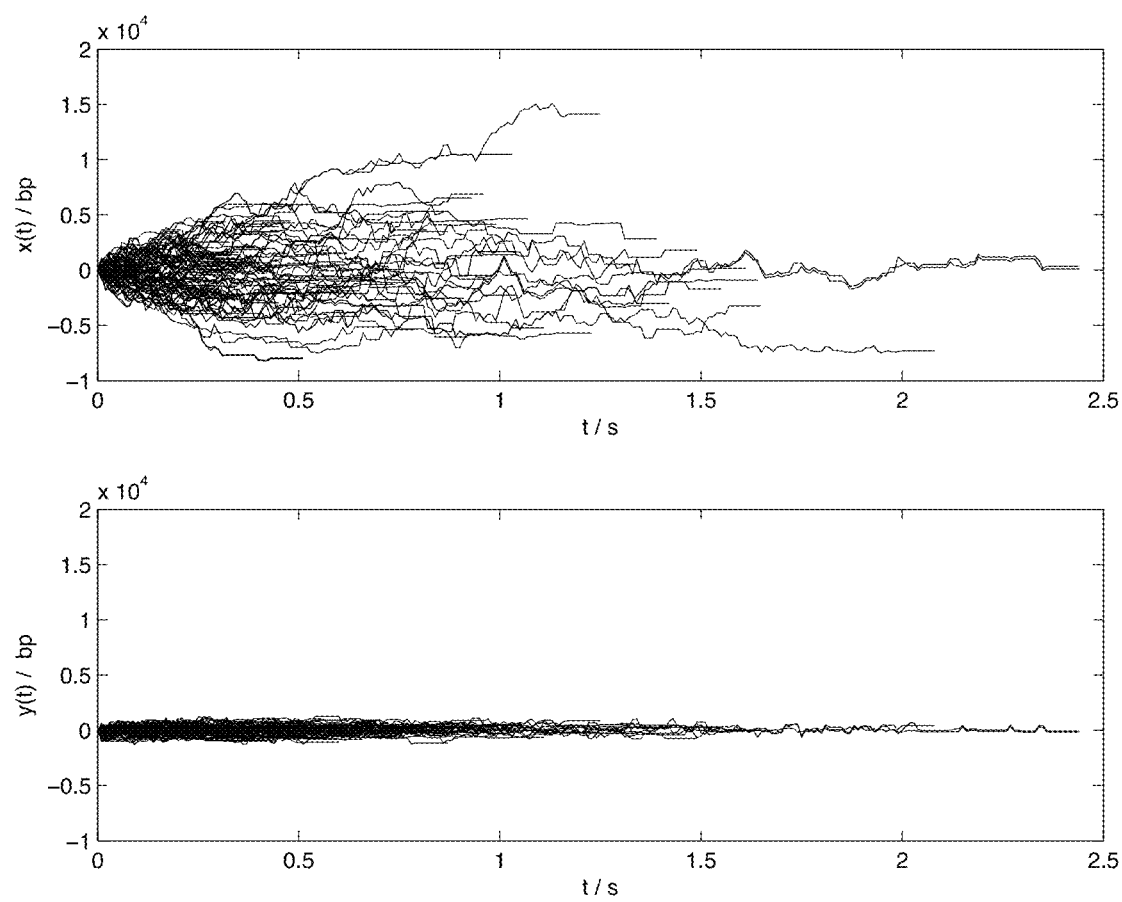
FIGS. 11A-11C depicts a kymograph of measured single molecule sliding trajectories and 1D diffusion constant of GCN4 helix and derivatives.
Figure 11B:
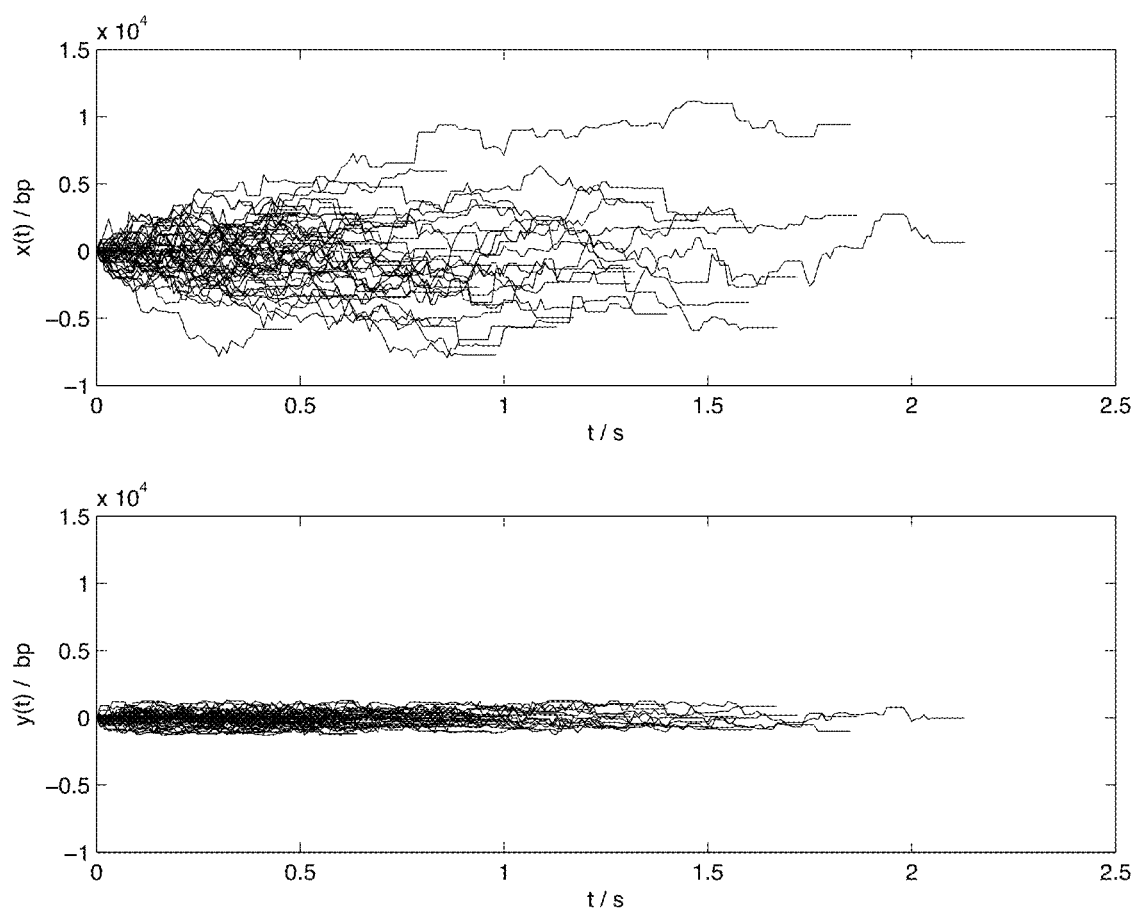
Figure 11C:
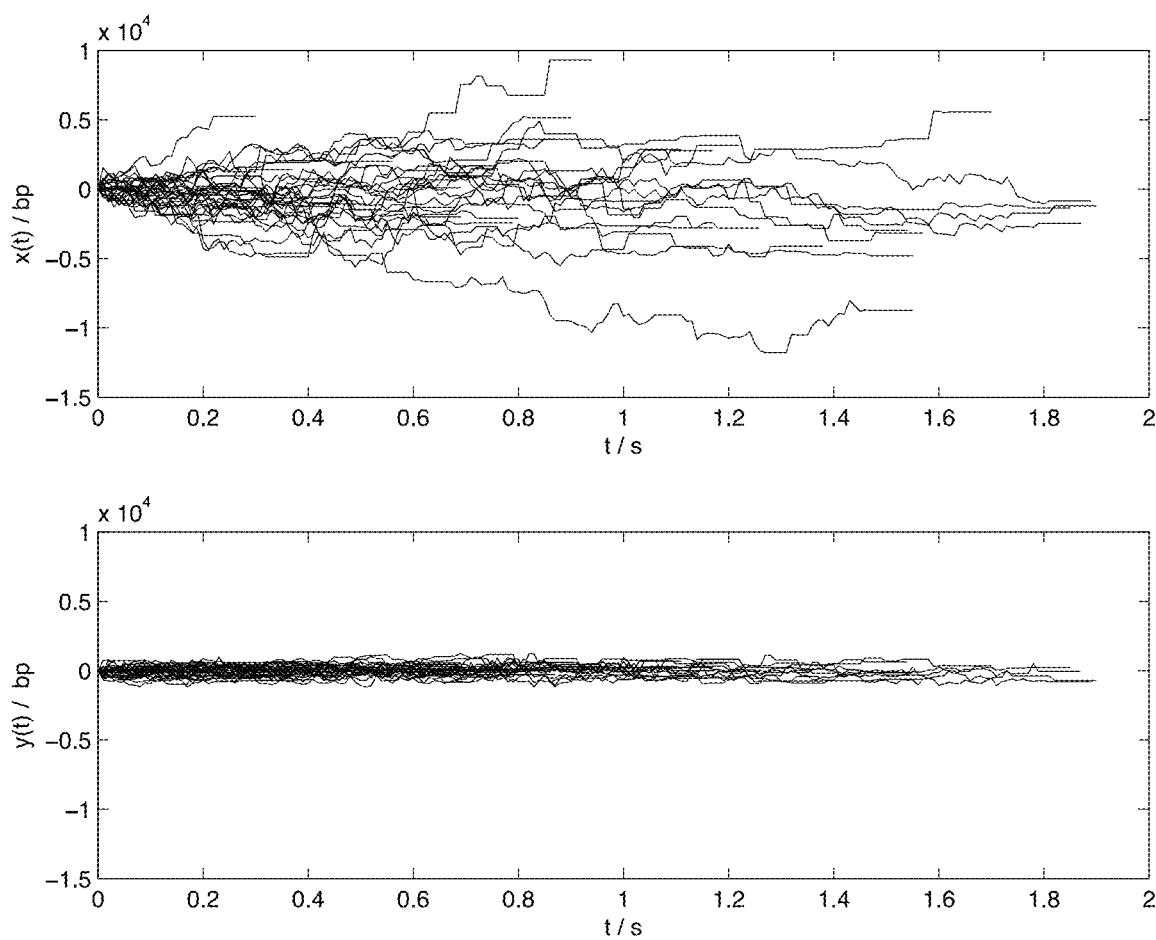

FIG. 11 depicts a kymograph of measured single molecule sliding trajectories and 1D diffusion constant of GCN4 helix and derivatives. FIG. 11A depicts the GCN4 helix, KRARN-TEAARRSRAR (SEQ ID NO: 16), D+SD*: (12.8±5.5)×$10^6$ $bp^2s^{-1}$ and D+SEM*: (12.8±0.6)×$10^6$ $bp^2s^{-1}$. FIG. 11B depicts the GCN4 helix-linker-KRRR ('KRRR' disclosed as SEQ ID NO: 2), KRARNTEAARRSRAR-GSGSGS-KRRR (SEQ ID NO: 17), D+SD: (11.3±4.1)×$10^6$ $bp^2s^{-1}$ and D+SEM: (11.3±0.6)×$10^6$ $bp^2s^{-1}$. FIG. 11C depicts the GCN4 helix-linker-pVIc, KRARNTEAARRSRAR-GSGSGS-pVIc ('KRARNTEAARRSRAR-GSGSGS' disclosed as SEQ ID NO: 18), D+SD: (9.6±4.3)×$10^6$ $bp^2s^{-1}$ and D+SEM: (9.6±0.7)×$10^6$ $bp^2s^{-1}$.

Figure 12A:
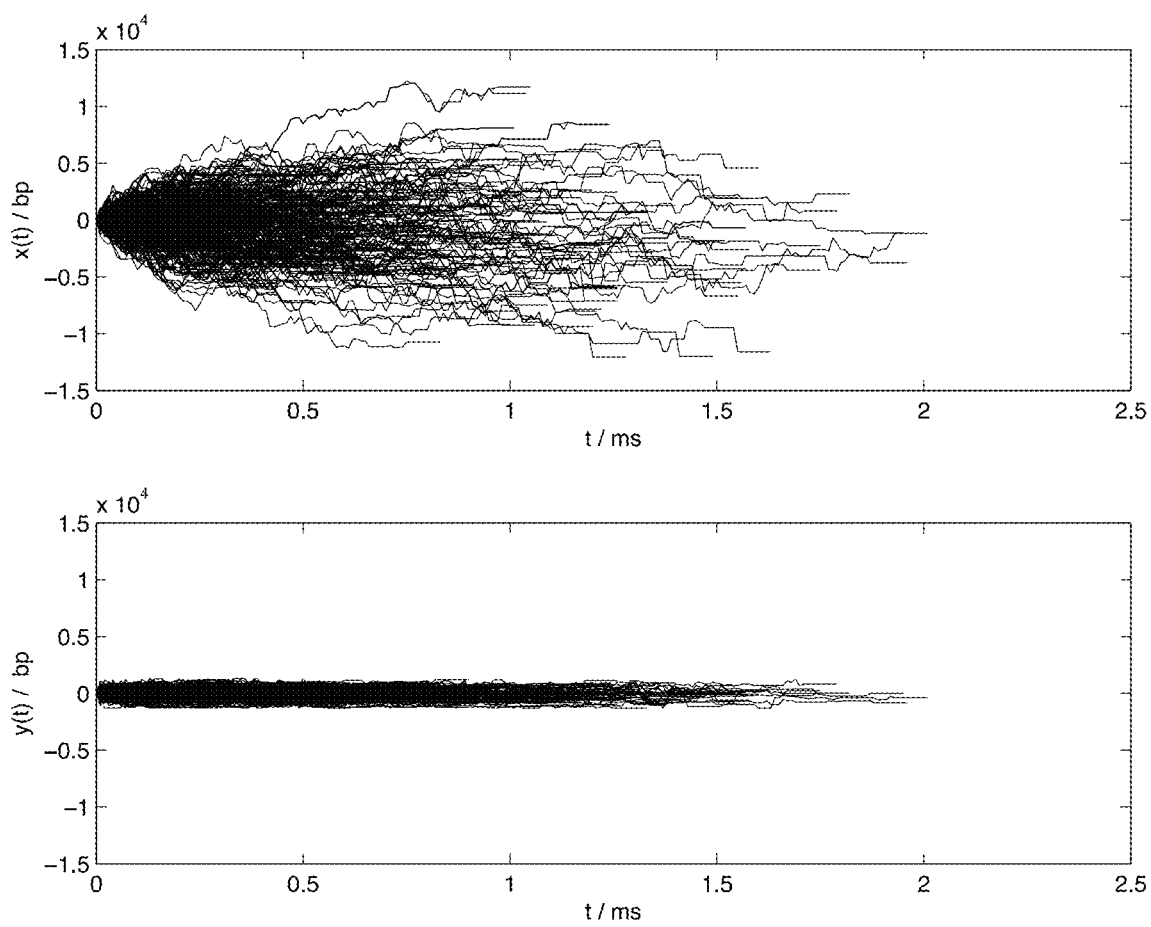
FIGS. 12A-12B depicts a kymograph of measured single molecule sliding trajectories and 1D diffusion constant of cMyc helix and derivatives.
Figure 12B:
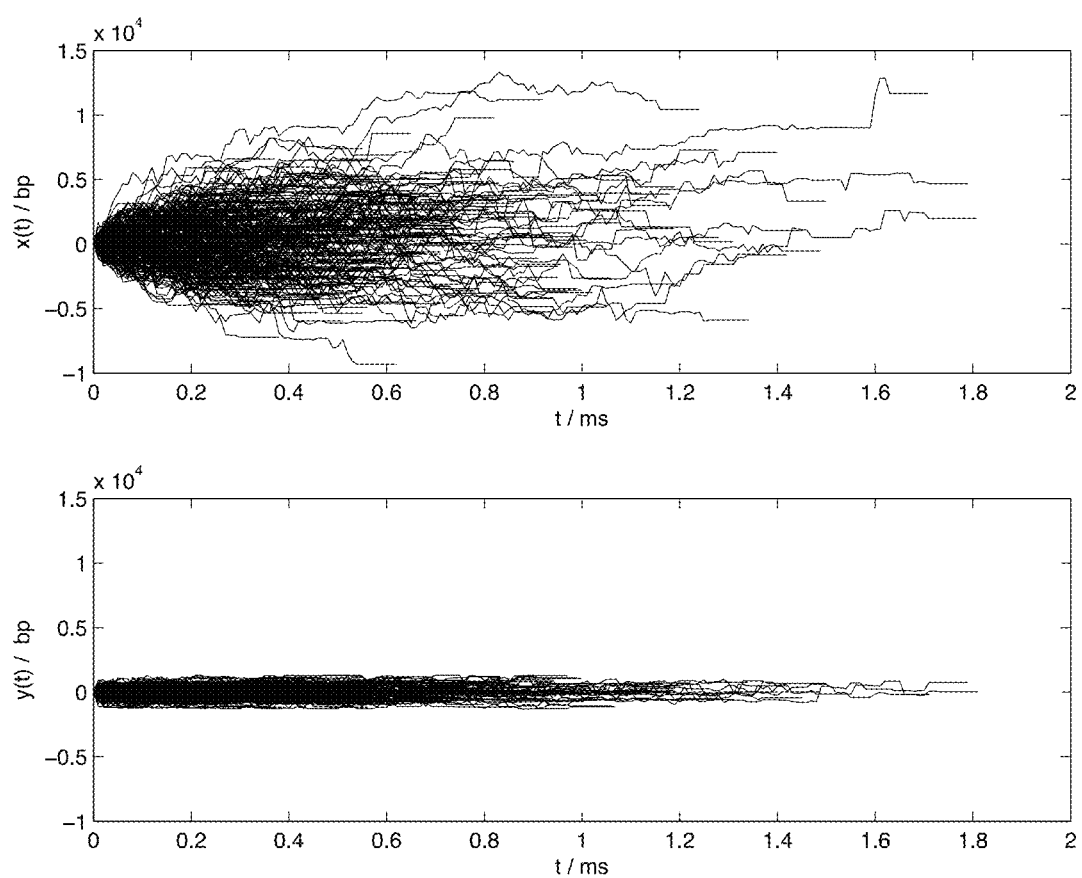

FIG. 12 depicts a kymograph of measured single molecule sliding trajectories and 1D diffusion constant of cMyc helix and derivatives. FIG. 12A depicts the cMyc helix, NVKRRTHNVLERQRRNELKRSFFALRDQ (SEQ ID NO: 19), D+SD: (12.8±5.0)×$10^6$ $bp^2s^{-1}$ and D+SEM: (12.8±0.3)×$10^6$ $bp^2s^{-1}$. FIG. 12B depicts the cMyc helix, NVKRRTHNVLERQRRNELKRSFFALRDQ (SEQ ID NO: 19), D+SD: (12.8±5.0)×$10^6$ $bp^2s^{-1}$ and D+SEM: (12.8±0.3)×$10^6$ $bp^2s^{-1}$.

Example 3

This Example discusses circumventing two types of drug resistance mechanisms by using peptide to deliver drug molecules as illustrated in Annu Rev. Med., 53, 615-27.

Figure 13A:
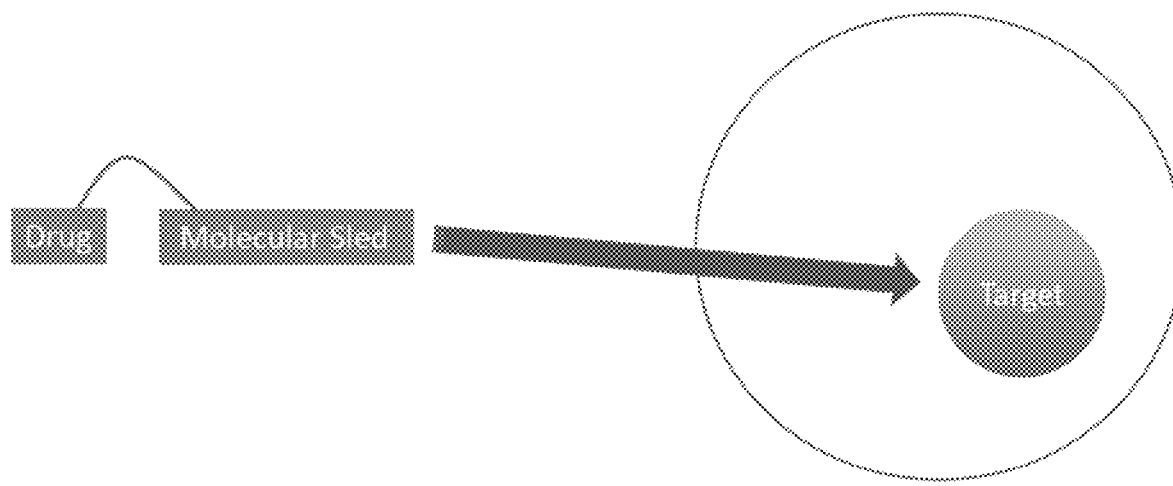
FIG. 13A depicts a strategy for developing a general model system for studying peptide drug delivery.

FIG. 13A depicts a strategy for developing a general model system for studying peptide drug delivery.

A luciferin-luciferase system is contemplated. Advantages of bioluminescence include 10-100 fold higher sensitivity than fluorescence and no external excitation, no photobleach and no phototoxicity.

Luciferin-luciferase subcellular imaging may be contemplated via the shuttling of importin-alpha protein between the cytosol and nucleus as shown in Plos One, 5, e10011 (2010).

Substrates of firefly luciferase are presented in Chem. Asian J. 2011, 6, 1800-1810 and Chem. Soc. Rev., 2013, 42, 662-676.

Figure 13B:
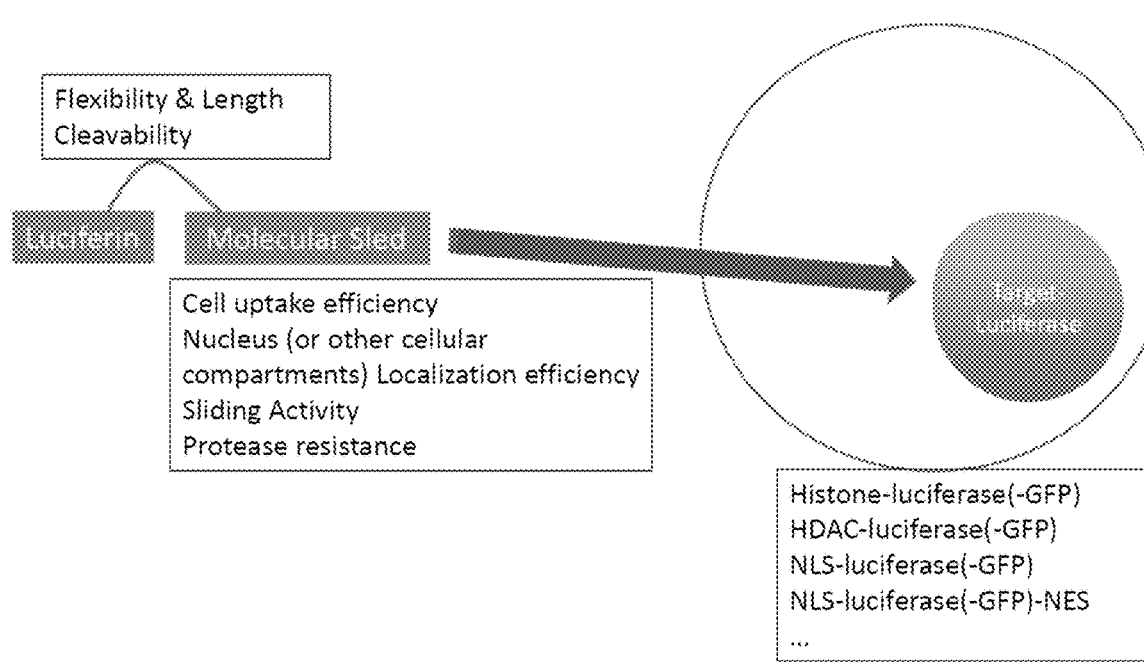
FIG. 13B depicts a strategy for (a) transfecting luciferase constructs (pcDNA3.1(+)/Luc2=tdT, pRLG3A from Addgene) into mammalian cells, checking expression level and bioluminescence sensitivity (with D-Luciferin); (b) making and transfecting luciferase-target constructs into mammalian cells, checking expression levels, cellular localization and bioluminescence sensitivity (with D-Luciferin); (c) determining cell uptake/NLS/Sliding activity of peptides; (d) synthesizing and purifying CycLuc1-peptide conjugates; (d) determining efficiency of peptide delivery of CycLuc1 to specific targets and (e) testing with real drugs.

This Example involves (a) transfecting luciferase constructs (pcDNA3.1(+)/Luc2=tdT, pRLG3A from Addgene) into mammalian cells, checking expression level and bioluminescence sensitivity (with D-Luciferin); (b) making and transfecting luciferase-target constructs into mammalian cells, checking expression levels, cellular localization and bioluminescence sensitivity (with D-Luciferin); (c) determining cell uptake/NLS/Sliding activity of peptides; (d) synthesizing and purifying CycLuc1-peptide conjugates; (d) determining efficiency of peptide delivery of CycLuc1 to specific targets and (e) testing with real drugs which is illustrated in FIG. 13B.

Example 4

Chemicals:

All TMR labeled peptides and peptidomimetics were purchased from Biopolymer & Proteomics Laboratory at MIT (with >85% purity). TMR labeled polyamides (see their chemical structures in FIG. 18 in the supplement) were obtained from Prof. Aseem Ansari's lab at University of Wisconsin. Cy3B-NHS ester was purchased from GE Healthcare Life Sciences. Cy3B-pentaethylenehexamine (PHEA) was prepared by reacting Cy3B-NHS ester with PHEA (the molar ratio of reactive dye to PHEA 1:10), and the final product was purified by HPLC and confirmed by MALDI analysis. λ-DNA was purchased from New England Biolabs, and a DNA oligo with a biotin attached, 5'-GGGCGGCGACCTAAAAAAAAAAA-biotin-3' (SEQ ID NO: 30) was ordered from IDT. A 30-mer oligo (5'-GACGACTAGGACGACGACGAGGATGACGAC-3' (SEQ ID NO: 31)) and its complementary strand were purchased from IDT and annealed together to form a double-stranded 30-mer for binding studies.

Single Molecule Flow Stretching Experiments:

The experimental details have been described by Xiong et al. Briefly, flow cells were constructed by sandwiching a double-sided tape with pre-cut channels between a poly (ethylene glycol) (PEG) functionalized coverslip and a PDMS slab containing inlet and outlet holes. The biotin-λ-DNA was made by ligating a DNA oligo with a biotin attached to the 5' overhang of λ-DNA, and then immobilized onto the flow channel surface by utilizing biotin and streptavidin chemistry. Samples were infused at 10-400 pM concentrations at rates of 25 ml/hr. The assay buffer consisted of 10 mM phosphate buffer, 2 mM NaCl, 50 μM EDTA, 20 mM ethanol, 5% (v/v) glycerol, 0.01% Tween-20 and 0.1% (v/v) β-mercaptoethanol, and the pH was adjusted to 7.4 by adding aliquots of concentrated NaOH solution. Individual dye-labeled molecules were imaged by using a home-built total internal reflection fluorescence microscope based on a Nikon Ti body with a Hamamatsu ORCA-Flash 4.0 V1 camera. Applicants used customized single particle tracking software to process the raw image data[11].

Fluorescence Polarization (FP) Experiments:

Steady-state FP measurements were performed using a SpectraMax M5 plate reader from Molecular Devices. Samples were prepared in a 96-well plate. To determine dissociation constant, $K_d$ values, the fluorophore-labeled sample concentrations were held at 10 nM, and 30 bp dsDNA was titrated from 3000 to 0 nM. The excitation/emission/cut-off wavelengths were set as 544/590/570 nm. The Kd values were estimated by fitting the FP data to a one-to-one stoichiometry binding model.[11] (Xiong et al).

To study the motion of single molecules bound to DNA, Applicants applied a single-molecule flow-stretching assay that prepares long double-stranded DNA molecules as spatially extended templates for analysis of binding and transport activity of molecular sleds labeled with fluorescent dye molecules. (Blainey, P. C.; van Oijen, A. M.; Banerjee, A.; Verdine, G. L.; Xie, X. S.; van Oijen, A. M.; Blainey, P. C.; Crampton, D. J.; Richardson, C. C.; Ellenberger, T.; Xie, X). In this assay (see a schematic in FIG. 19), functionalized DNA, e.g., biotin-λ-DNA, was immobilized to a flow channel surface by one end and a laminar flow was applied to flow stretch the DNA. The flow rate was chosen so that the contribution of DNA fluctuations to the apparent motion of DNA-bound molecules along the DNA is negligible and the trajectories of single molecules were tracked by time-lapse fluorescence imaging. Here, Applicants applied the flow-stretching assay to study one-dimensional diffusion of modified peptides, peptide analogs and synthetic small molecules bound to DNA. FIG. 22 shows the measured raw trajectories of different samples diffusing on λ-DNA, from which their 1D diffusion constant, D1 values were calculated.[11]

Converting a C-terminal carboxylate of peptidyl sleds to an amide dramatically increases their sliding activity and DNA affinity Applicants previously observed that retaining a free N-terminal amine increases the sliding activity and DNA affinity of peptidyl sleds, as shown in Table S1, below, in which one-dimensional diffusion constants (D1) and equilibrium dissociation constants ($K_d$) of pVIc and acetyl-pVIc. Cy3B was conjugated to Cys residues. Results from Xiong et al are indicted by "*".

TABLE S1

One-dimensional diffusion constants (D1) and equilibrium dissociation constants ($K_d$) of pVIc and acetyl-pVIc.

| Molecule sled | D1 ± s.e. (M(bp$^2$/S)) | s.d. (M(bp$^2$/S)) | $K_d$ (nM) |
|---|---|---|---|
| pVIc-Cy3B * | 35.1 ± 0.8 | 17.7 | 378 ± 20 |
| Acetyl-pVIc-Cy3B * | 16.4 ± 1.1 | 7.5 | 1307 ± 224 |

Here, a similar effect was observed upon converting a C-terminal carboxylate to an amide. The D1 value of TMR-$^L$K$^L$R$^L$R$^L$R (SEQ ID NO: 32) increases from 10.5±0.7 to 22.1±0.8 M(bp$^2$/s) upon converting its C-terminal carboxylate to an amide (FIG. 14), while its $K_d$ value decreases from 197±40 to 46±7 nM (Table S2, below). One-dimensional diffusion constants (D1) and equilibrium dissociation constants ($K_d$) of peptidyl molecular sleds. All the D1 and $K_d$ values were measured at pH 7.4. On average, >100 trajectories were analyzed to estimate each D1 value. Results from Xiong et al are indicted by "*".(Table S2 discloses SEQ ID NOS 32, 33, 35, 42, 34, 41, 40 and 43, respectively, in order of appearance).

TABLE S2

One-dimensional diffusion constants (D1) and equilibrium dissociation constants ($K_d$) of peptidyl molecular sleds

| Molecule sled | D1 ± s.e. (M(bp$^2$/S)) | s.d. (M(bp$^2$/S)) | $K_d$ (nM) |
|---|---|---|---|
| TMR-$^L$K$^L$R$^L$R$^L$R * | 10.5 ± 0.7 | 5.0 | 197 ± 40 |
| TMR-$^L$R$^L$R$^L$R$^L$R * | 11.3 ± 1.0 | 5.3 | 236 ± 10 |
| TMR-$^L$K$^L$R$^L$R$^L$R-NH$_2$ | 22.1 ± 0.8 | 9.2 | 46 ± 7 |
| TMR-$^L$R$^L$R$^L$R$^L$R-NH$_2$ | 14.9 ± 0.4 | 7.2 | 31 ± 6 |
| $^L$K$^L$R$^L$R$^L$R$^L$C(-TMR)-NH$_2$ | 22.6 ± 0.6 | 9.3 | 54 ± 19 |
| TMR-$^L$R$^L$R$^L$R$^L$R-K-NH$_2$ | 13.1 ± 0.5 | 5.4 | 28 ± 5 |
| TMR-$^L$K$^L$K$^L$K$^L$K-NH$_2$ | 23.3 ± 1.2 | 11.0 | 53 ± 8 |
| TMR-(CH$_2$)$_5$-$^L$K$^L$R$^L$R$^L$R-NH$_2$ | 20.6 ± 0.8 | 7.6 | 46 ± 9 |

Figure 15:
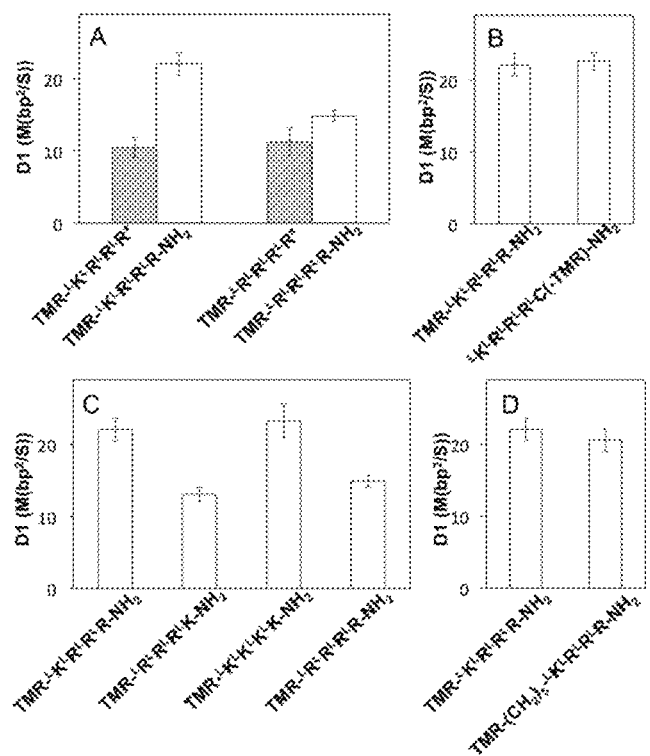
FIG. 15 illustrates one-dimensional diffusion constants (D1) of peptidyl molecular sleds in 2 mM NaCl buffer. TMR was conjugated to the N-terminal amines of all peptides except for $^LK^LR^LR^LR^LC$(-TMR)—NH2 (SEQ ID NO: 34) whose TMR was conjugated to the Cys residue. All the D1 values were measured at pH 7.4. On average, >100 trajectories were analyzed to estimate each D1 value. All the error bars represent 95% confidence intervals. * Results from Xiong11. See Supplementary Table S2 for D1 values.

Similarly, the D1 value of TMR-$^L$R$^L$R$^L$R$^L$R (SEQ ID NO: 33) increases from 11.3±1.0 to 14.9±0.4 M(bp$^2$/s), while its $K_d$ value decreases from 236±10 to 31±6 nM (Table S2). Knowing that either converting a C-terminal carboxylate to an amide or retaining a free N-terminal amine dramatically enhances activities of peptidyl sleds, Applicants were curious whether the C-terminal effect and the N-terminal effect could be combined. FIG. 15B and Table S2 show that the D1 and $K_d$ values of $^L$K$^L$R$^L$R$^L$R$^L$C(-TMR)—NH$_2$ (SEQ ID NO: 34), which has free N-terminal and C-terminal amide (TMR is conjugated to the Cys residue) are 20.6±0.8 M(bp$^2$/s) and 46±9 nM, respectively, essentially identical to those of TMR-$^L$K$^L$R$^L$R$^L$R—NH$_2$ (SEQ ID NO: 35) which has only a C-terminal amide, indicating that the N-terminal effect and the C-terminal effects are not additive.

Table S3 shows one-dimensional diffusion constants (D1) and equilibrium dissociation constants (Kd) of peptidyl sleds. TMR was conjugated to Cys residues of C(-TMR)-(K)13 (SEQ ID NO: 36) and C(-TMR)—(R)13 (SEQ ID NO: 37), while TMR was conjugated to the N-terminal amine of TMR-(K)13 (SEQ ID NO: 38) and TMR-(R)13 (SEQ ID NO: 39). Results from Xiong et al are indicted by "*". (Table S3 discloses SEQ ID NOS 36, 38, 37 and 39, respectively, in order of appearance).

TABLE S3

One-dimensional diffusion constants (D1) and equilibrium dissociation constants ($K_d$) of peptidyl sleds.

| Molecule sled | D1 ± s.e. (M(bp$^2$/S)) | s.d. (M(bp$^2$/S)) |
|---|---|---|
| C(-TMR)-(K)$_{13}$* | 19.9 ± 1.3 | 9.6 |
| TMR-(K)$_{13}$* | 8.9 ± 0.5 | 2.1 |
| C(-TMR)-(R)$_{13}$* | 12.9 ± 0.5 | 6.0 |
| TMR-(R)$_{13}$* | 7.7 ± 0.7 | 2.7 |

Converting a C-terminal carboxylate of peptidyl sleds to an amide renders their sliding activity sensitive to primary amino acid sequence variation Previously, Applicants observed that the D1 values of peptidyl sleds with a N-terminal fluorophore and a C-terminal carboxylate are insensitive to amino acid sequence variation. (Xiong et al). Here Applicants observed that converting a C-terminal carboxylate to an amide renders their sliding activity more sensitive to amino acid sequence variation. FIG. 15C shows that the D1 values of TMR-$^LK^LR^LR^LR$—NH$_2$ (SEQ ID NO: 35), TMR-$^LK^LK^LK^LK$—NH$_2$ (SEQ ID NO: 40), TMR-$^LR^LR^L$-R$^LK$—NH2 (SEQ ID NO: 41) and TMR-$^LR^LR^LR^LR$—NH$_2$ (SEQ ID NO: 42) range from 13.1±0.5 to 23.3±1.2 M(bp$^2$/s). Table S2 shows that the Kd values of the faster-sliding TMR-$^LK^LR^LR^LR$—NH2 (SEQ ID NO: 35) and TMR-$^LK^LK^LK^LK$—NH$_2$ (SEQ ID NO: 40) peptides (Kd=46±7, 53±8 nM, respectively) are higher than those of the slower-sliding TMR-$^LR^LR^LR^LK$—NH$_2$ (SEQ ID NO: 41) and TMR-$^LR^LR^LR^LR$—NH2 peptides (SEQ ID NO: 42) (Kd=28±5, 31±6 nM, respectively). These results are consistent with the notion in the facilitated diffusion field that a molecule that binds DNA more tightly slides more slowly due to greater interaction (friction) with the DNA.[20] FIG. 15D and Table S2 also show that inserting a C5 linker between TMR and the N-terminal amine does not significantly affect the sliding activity or DNA affinity of TMR-$^LK^LR^LR^LR$—NH$_2$ (SEQ ID NO: 35) (the D1 values of TMR-$^LK^LR^LR^LR$—NH$_2$ (SEQ ID NO: 35) and TMR-(CH$_2$)$_5$-$^LK^LR^LR^LR$—NH$_2$ (SEQ ID NO: 43) are 22.1±0.8 and 20.6±0.8 M(bp$^2$/s), respectively, and their Kd values are 46±7 and 46±9 nM, respectively), indicating that the sterically constrained N-terminal dye molecule does not interfere with sliding, consistent with Applicants' previous observation that peptides labeled N-terminally with different dye molecules slide with the same D1 value. (Xiong et al).

Figure 14:
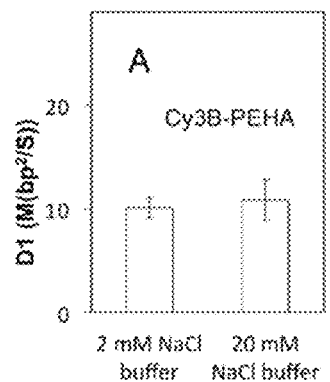
FIG. 14 illustrates one-dimensional diffusion constants (D1) of synthetic small molecules. A). The D1 values of Cy3B-PEHA in 2 mM NaCl and 20 mM NaCl buffers. B). The D1 values of TMR-PA4 and TMR-PA5 in 2 mM NaCl buffer. All the values were measured at pH 7.4. On average, >50 trajectories were analyzed to estimate each D1 value. All the error bars represent 95% confidence intervals. See Supplementary Table S5 for D1 values.
Figure 16:
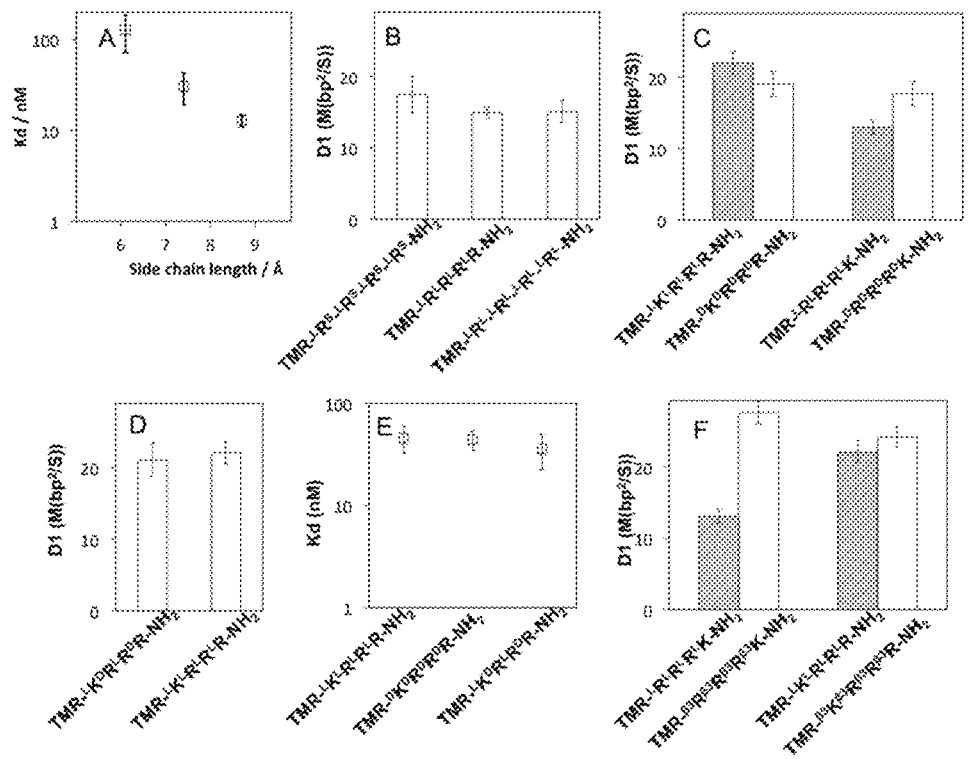
FIG. 16 shows a correlation between the $K_d$ values of tetra-arginine-like peptides and their side chain lengths. The fully extended side chain lengths of $^LR^S$, $^LR$ and $^LR^L$ are 6.1, 7.4 and 8.7 Å, respectively. B-D & F). One-dimensional diffusion constants (D1) of peptide analogs in 2 mM NaCl buffer. E). The effect of the peptide backbone chirality on equilibrium dissociation constants ($K_d$). TMR was conjugated to the N-terminal amines. All the D1 and $K_d$ values were measured at pH 7.4. On average, >100 trajectories were analyzed to estimate each D1 value. All the error bars represent 95% confidence intervals. See Supplementary Table S4 for D1 and Kd values.

The length of guanidinium side chains in tetra-arginine-like peptides has strong effects on DNA affinity but does not affect sliding activity: To study the side chain length effect on activities of molecular sleds, Applicants measured D1 and Kd values of tetra-arginine-like peptides with side chain lengths both shorter ($^LR^S$: L-2-amino-3-guanidinopropionic acid whose side chain has one less —CH$_2$— group than does arginine) and longer than arginine ($^LR^L$: L-homo-arginine whose side chain has one more —CH$_2$— group than does arginine). Previous structural modeling based on structural studies of pVIc in complex with the adenoviral proteinase (AVP; the enzyme it activates catalytically and endows with sliding activity) described the four basic residues of pVIc, KRRR (SEQ ID NO: 2) spanning the major groove (with backbone in a (3-sheet-like configuration) to contact up to four DNA phosphate groups.[9] Applicants subsequently presented an alternative model with lysine and arginine side chains inserted into the minor groove, which is much narrower than the major groove.[11] FIG. 16A shows that the Kd values of tetra-arginine-like peptides rapidly decrease as the side chain length increases (the Kd values of TMR-$^LR^S$-$^LR^S$-$^LR^S$-$^LR^S$—NH$_2$ (SEQ ID NO: 44), TMR-$^LR^LR^LR^LR$—N$_{H2}$ (SEQ ID NO: 42) and TMR-$^LR^{L-L}$R$^{L-L}$R$^{L-L}$R$^L$—NH$_2$ (SEQ ID NO: 45) are 129±29, 31±6 and 13±1 nM, respectively). The fact that tetra-arginine-like peptides with shorter side chains bind DNA more weakly suggests a structural constraint that prevents shorter side chains from reaching across the DNA major groove or alternatively, inserting far enough into the DNA minor groove (FIG. 14). Although the side chain length-dependent binding data do not clearly distinguish the major and minor groove models for molecular sled binding, Applicants prefer the minor groove model based on the observations that arginine and lysine more commonly insert into the DNA minor groove in available structures, the highly focused electric field found in the minor groove,[21] and Applicants' previous report that minor-groove binding dyes strongly interfered with molecular sled activity.[11] In contrast with the dramatic effect on DNA affinity, Applicants did not observe a dramatic side chain length dependence of sliding activity. FIG. 16B shows that D1 values of TMR-$^LR^S$-$^LR^S$-$^LR^S$—NH$_2$ (SEQ ID NO: 44), TMR-$^LR^LR^LR^LR$—NH$_2$ (SEQ ID NO: 42), TMR-$^LR^L$-$^LR^L$-$^LR^L$-$^LR^L$—NH$_2$ (SEQ ID NO: 45) are 17.4±1.3, 14.9±0.4 and 15.1±0.8 M(bp$^2$/s), respectively. The fact that peptides with shorter side chains slide as fast as peptides with longer side chains indicates that fast sliding does not require side chains to reach deeply into the DNA minor groove. The relative independence of DNA binding affinity and D1 in this series contrasts with the notion that greater affinity leads to greater friction with DNA[20] and indicates that other dynamics are at play. Previous studies also showed that the DNA affinity and sliding activity of molecular sleds do not always correlate, such as those across TAT and p53.[11]

The Chirality of the Peptide Backbone has Modest Impact on Sliding Activity and DNA Affinity.

Figure 17:
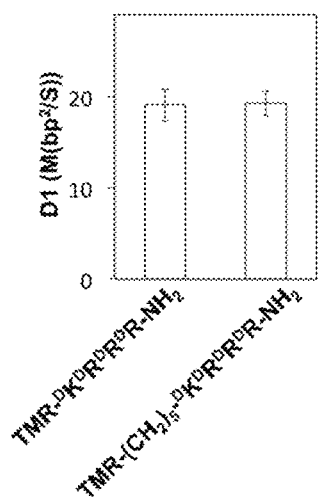
FIG. 17 illustrates one-dimensional diffusion constants of TMR—KRRR—NH$_2$ (SEQ ID NO: 48) and TMR-(CH$_2$)$_5$—KRRR—NH$_2$ (SEQ ID NO: 49) in 2 mM NaCl buffer. All the D1 values were measured at pH 7.4. On average, >100 trajectories were analyzed to estimate each D1 value. All the error bars represent 95% confidence intervals. See Supplementary Table S4 for D1 values.

To investigate the impact of the backbone chirality on the activities of molecular sleds, Applicants measured the D1 and Kd values of peptides containing all L-, all D- and alternating L-, D-amino acids. FIG. 16C shows that the D1 value of TMR-$^DK^DR^DR^DR$—NH$_2$ is slightly lower than that of TMR-$^LK^LR^LR^LR$—NH$_2$ (SEQ ID NO: 35) (D1=19.1±0.9 and 22.1±0.8 M(bp$^2$/s), respectively) while the D1 value of TMR-$^DR^DR^DR^DK$—NH2 is higher than that of TMR-$^LR^L$-R$^LR^LK$—NH$_2$ (SEQ ID NO: 41) (D1=17.8±0.9 and 13.1±0.5 M(bp$^2$/s), respectively). The D1 value of a peptide containing alternating L- and D-amino acid, TMR-K$^D$RR$^D$R—NH$_2$ is nearly identical to that of TMR-$^LK^LR^L$-R$^LR$—NH$_2$ (SEQ ID NO: 35) (D1=21.1±1.2 and 22.1±0.8 M(bp$^2$/s), respectively; see FIG. 16D). Applicants also observed that the Kd values of TMR-$^LK^DR^DR^DR$—NH$_2$ (SEQ ID NO: 35), TMR-$^LK^LR^LR^LR$—NH$_2$ and TMR-$^DK^DR^DR^DR$—NH$_2$ are essentially identical (Kd=36±7, 46±7 and 44±5 nM, respectively; see FIG. 16E). In the context of the major-groove sliding model, much lower DNA affinity would be expected for a β-strand peptide containing alternating L- and D-amino acids as its side chains are displayed on the same side of the DNA major groove compared to a β-strand peptide containing all L- or all D-amino acids whose side chains are displayed on two sides when the backbone is in the β-strand configuration.[22] Conversely, the minor groove model would predict somewhat stronger DNA affinity. The fact that alternating chirality of the peptide backbone has a minor impact (if anything strengthening DNA affinity) suggests that peptidyl sleds do not adopt β-strand conformation in their DNA-bound state as required in the major-groove model. FIG. 17 and Table S4 also show that inserting a flexible linker between TMR and the N-terminal amine does not impact D1 and Kd value (the D1 values of TMR-$^DK^DR^DR^DR$—NH$_2$ and TMR—(CH$_2$)$_5$-$^DK^DR^DR^DR$—NH$_2$ are 19.1±0.9 and 19.3±0.7 M(bp$^2$/s), respectively; and their Kd values are 44±5 and 47±8 nM, respectively), indicating that the N-terminal TMR does not interfere with sliding or DNA binding properties of D-peptides. One-dimensional diffusion constants (D1) and equilibrium dissociation constants ($K_d$) of peptidomimetics in 2 mM NaCl buffer. All the D1 and $K_d$ values were measured at pH 7.4. On average, >100 trajectories were analyzed to estimate each D1 value. *$^LR^S$: L-2-amino-3-guanidinopropionic acid whose side chain has one less—CH$_2$— group than does arginine) and longer than arginine ($^LR^L$: L-homo-arginine whose side chain has one more —CH$_2$—group than does arginine; ** $^LR$: homo-arginine whose side chain has one more —CH$_2$— group than does arginine. (Table S4 discloses SEQ ID NOS 44, 42, 45, 35, 41, 47 and 46, respectively, in order of appearance)

TABLE S4

One-dimensional diffusion constants (D1) and equilibrium dissociation constants ($K_d$) of peptide analog molecular sleds

| Molecule sled | D1 ± s.e. (M(bp$^2$/S)) | s.d. (M(bp$^2$/S)) | $K_d$ (nM) |
|---|---|---|---|
| TMR-$^LR^S$-$^LR^S$-$^LR^S$-$^LR^S$-NH$_2$* | 17.4 ± 1.3 | 9.0 | 129 ± 29 |
| TMR-$^LR^LR^LR^LR$-NH$_2$ | 14.9 ± 0.4 | 7.2 | 31 ± 6 |
| TMR-$^LR^L$-$^LR^L$-$^LR^L$-$^LR^L$-NH$_2$** | 15.1 ± 0.8 | 7.4 | 13 ± 1 |
| TMR-$^LK^LR^LR^LR$-NH$_2$ | 22.1 ± 0.8 | 9.3 | 46 ± 7 |
| TMR-$^LR^LR^LR^LK$-NH$_2$ | 13.0 ± 0.5 | 5.4 | 28 ± 5 |
| TMR-$^DK^DR^DR^DR$-NH$_2$ | 19.1 ± 0.9 | 9.7 | 44 ± 5 |
| TMR-$^DR^DR^DR^DK$-NH$_2$ | 17.8 ± 0.9 | 7.3 | 37 ± 9 |
| TMR-$^LK^DR^LR^DR$-NH$_2$ | 21.1 ± 1.2 | 12.7 | 36 ± 7 |
| TMR-(CH$_2$)$_5$-$^DK^DR^DR^DR$-NH$_2$ | 19.3 ± 0.7 | 8.6 | 47 ± 8 |
| TMR-$^{β3}K^{β3}R^{β3}R^{β3}R$-NH$_2$ | 24.2 ± 0.7 | 10.1 | 41 ± 7 |
| TMR-$^{β3}R^{β3}R^{β3}R^{β3}K$-NH$_2$ | 27.6 ± 0.8 | 12.2 | 49 ± 8 |

β3-peptides allows faster sliding activity but only slightly impacts DNA affinity To study how the backbone structure affects activities of molecular sleds, Applicants measured the D1 and Kd values of β$^3$-peptides, which have an additional methylene group in the backbone of each monomer. FIG. 16F shows that the D1 value of TMR-$^{β3}R^{β3}R^{β3}R^{β3}K$—NH$_2$ (SEQ ID NO: 46) is twice that of TMR-$^LR^LR^LR^LK$—NH$_2$ (SEQ ID NO: 41) (D1=27.6±0.8 and 13.1±0.5 M(bp$^2$/s), respectively) and the D1 value of TMR-$^{β3}K^{β3}R^{β3}R^{β3}R$—NH$_2$ (SEQ ID NO: 47) is slightly higher than that of TMR-$^LK^LR^LR^LR$—NH$_2$ (SEQ ID NO: 35) (D1=24.2±0.7 and 22.1±0.8 M(bp$^2$/s), respectively). Table S4 also shows that the Kd values of β$^3$-peptides are similar to those of natural peptides (the Kd values of TMR-$^{β3}R^{β3}R^{β3}R^{β3}K$—NH$_2$, (SEQ ID NO: 46) TMR-$^{β3}K^{β3}R^{β3}R^{β3}R$—NH$_2$ (SEQ ID NO: 47), TMR-$^LR^L$-$R^LT^LK$—NH$_2$ (SEQ ID NO: 41) and TMR-$^LK^LR^LR^LR$—NH$_2$ (SEQ ID NO: 35) are 49±8, 41±7, 28±5, 46±7 nM, respectively), suggesting electrostatic binding interactions with DNA that are analogous to standard peptides. The faster sliding activity of β$^3$-peptides might result from the more flexible backbone which allows them to adopt conformations that better accommodate the typical shape of the minor groove and/or DNA sequence-dependent groove shape variations along λ-DNA.

A Non-Brunched Small Molecule Slides on DNA:

Seeing that many examples of branched-chain peptides and peptide analogs slide on DNA here and in Applicants' previous works[9,11] Applicants were curious whether non-brunched small molecule(s) are capable of sliding. Previous studies have shown that the interactions between polyamines and DNA are predominantly electrostatic and DNA sequence non-specific[23-25] characteristics that mirror those of known peptide molecular sleds, suggesting that polyamines might also slide on DNA. Following Applicants' experience analyzing structure-function relationships in peptides and analogs Applicants studied previously, Applicants selected pentaethylenehexamine (PHEA) based on its small size, number and spacing of charges, and symmetry that would yield a homogeneous population after reactive dye labeling (with Cy3B-NHS). Applicants performed single molecule flow stretching experiments and observed that PHEA-Cy3B indeed binds DNA with a Kd value is 1320±248 nM (Table S5), in line with reported Kd values of other polyamines[23] and the predicted charge-affinity trends Applicants observed across peptides.[11] One-dimensional diffusion constants (D1) and equilibrium dissociation constants ($K_d$) of synthetic small molecules in 2 mM NaCl buffer. All the values were measured at pH 7.4. On average, >50 trajectories were analyzed to estimate each D1 value. * PEHA: pentaethylenehexamine; ** see their chemical structures in FIG. 18.

TABLE S5

One-dimensional diffusion constants (D1) and equilibrium dissociation constants ($K_d$) of synthetic molecular sleds

| Molecule sled | D1 ± s.e. (M(bp$^2$/S)) | s.d. (M(bp$^2$/S)) | $K_d$ (nM) |
|---|---|---|---|
| Cy3B-PEHA* | 10.1 ± 0.5 | 5.0 | 1320 ± 248 |

PHEA-Cy3B is also capable of fast 1D translocation on DNA with an estimated D1 value of 10.1±0.5 M(bp$^2$/s) (FIG. 14). Increasing the salt concentration does not increase the D1 value of PHEA further (FIG. 14), indicating that PHEA translocates on DNA by sliding (2006 PNAS). These results suggest that a wide variety of other polyamines and extremely low molar mass small molecules with DNA affinity may also slide on DNA.

Previous work regarding facilitated diffusion and sliding along DNA focused exclusively on natural proteins, protein fragments and peptide molecular sleds. In this work, Applicants extended Applicants' previous findings to further investigate the structure-function relationships of molecular sled activity. Applicants discovered new ways to modulate the sliding activity and DNA affinity by chemically modifying peptidyl sleds. Applicants also discovered sliding activity in peptide analogs and synthetic small molecules. Applicants' work shed new light on the molecular basis of sliding.

Applicants surprisingly observed that converting a C-terminal carboxylate of peptidyl sleds to an amide dramatically increases their sliding activity and DNA affinity. The similar effect was previously observed by retaining a free N-terminal amine, the interpretation of which was appealed to changes in proton exchange kinetics or hydrogen bonding dynamics upon N-terminal functionalization.[11] Both the C-terminal and the N-terminal effects are puzzling for two reasons: 1). Converting a C-terminal carboxylate to an amide or retaining a free N-terminal amine decreases electrostatic repulsion or increases electrostatic attraction interaction between peptides and DNA, both of which could increase friction for sliding and thus 'decrease' D1; 2).

Applicants previously did not observe an increase in D by increasing the number of basic residues on a peptide.[11] Incongruity between equilibrium electrostatics and sliding dynamics was also observed with the DNA repair protein, human oxoguanine DNA glcosylase (hOgg1). hOgg1 has a single basic residue in its DNA-binding interface (Histidine 270) and exhibits a reduction in D1 above pH 7.5 when this residue is mutated to alanine. Mutating the interfacial histidine to a neutral and less bulky form would be expected to reduce the interaction with DNA and 'increase' D1. The parallel mysterious behavior between small peptides and the hOgg1 protein underscores the utility of small peptides as simplified model systems for mechanistic studies that are relevant to the functionality of much larger DNA binding proteins. From the aspect of molecular engineering, modifying the C-terminal or the N-terminal group presents a simple means to dramatically modulate on-DNA activities of molecular sleds. In mammalian proteome, the molecular sled sequences predominantly appear in the middle of primary amino acid sequences of proteins, resembling molecule sleds with a C-terminal amide, and thus could possibly support fast sliding. Interestingly, the C-terminal effect and the N-terminal effect are not additive, indicating that there is a high limit of D1 for molecular sleds of the same amino acid sequence. These results suggest that the dynamic interactions (e.g., hydrogen bonding interactions) between DNA and single or a few chemical moiety(-ies) of molecular sleds residing at the DNA-binding interfaces could drive fast sliding.

In contrast with a previously observed lack of amino acid sequence dependence of D1 for peptides with a N-terminal fluorophore and a C-terminal carboxylate[11], here Applicants observed that converting a C-terminal carboxylate to an amide renders D1 sensitive to amino acid sequence. A dependence of D1 on amino acid sequence was also observed by retaining a free N-terminal amine (see Table S2 in the supplement). These results suggest that for peptides with a C-terminal amide or a N-terminal free amine, due to decreased electrostatic repulsion or increased electrostatic attraction interaction between peptides and DNA, their arginine and lysine side chains could be in closer contact with DNA, thus differences in side chain —DNA interactions (for example, hydrogen bonding interactions) could occur and lysine and arginine residues make differential contribution to sliding.

Figure 18:
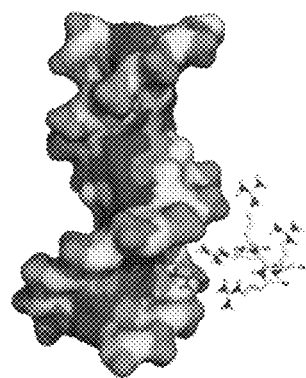
FIG. 18 is a model in which an α-helical-like RRRR peptide (SEQ ID NO: 50) slides in the minor groove of B-DNA (PDB code 1bdna). Between two and three arginine residues are contacting DNA phosphate groups.

Consistent with Applicants' most recent model[11], here Applicants' results suggest again that molecular sleds slide in the DNA minor groove. Furthermore, molecular sleds do not adopt β-strand conformation during sliding (FIG. 18). Applicants' previous structural modeling of the pVIc:AVP complex suggested that the complex could slide in the DNA major groove and the four basic residues of pVIc, KRRR (SEQ ID NO: 2) adopt β-strand conformation to contact up to four DNA phosphate groups[9]. It is noteworthy that Applicants did not have solid evidence for pVIc:AVP to slide in the DNA major groove, while a good structural fit between pVIc:AVP and DNA major groove suggest that sliding could still occur in the DNA major groove. It is known that many natural proteins capable of sliding recognize specific DNA sequences by interrogating bases in the DNA major groove, and it is compelling to study if they slide in the DNA major groove.

Like many natural transcriptional factors (TFs), pyrroleimidazole polyamides based TFs have to search for their DNA targets. While, polyamides based TFs do not work as well as natural TFs. Applicants expect that tuning sequence nonspecific binding and sliding activity of polyamides could accelerate their DNA target recognition. This proposed approach aims to improve the kinetics of cognate DNA binding of polyamides, in complementary with previous strategies focusing on optimizing their equilibrium properties. Furthermore, one major limitation of polyamides is their poor cellular permeability. Applicants recently reported that essentially all known nuclear localization signal sequences as well as many cell penetrating peptides are molecular sleds.[11] Future work will investigate whether tagging a molecular sled with cell penetrating and nuclear localization capabilities to polyamides based TFs could improve their pharmacokinetics.

Polyamines are known to play important roles in DNA function, such as in condensation of DNA, regulation of DNA structure, protection of DNA from external agents and against radiation damage.[23] Applicants' results suggest that polyamines with enough DNA affinity can slide on DNA. It is interesting to ask whether sliding plays a role in these biological processes. Furthermore, PHEA is the smallest molecular sled ever characterized, with a molecular weight (mw) of only ~230 Dalton. Applicants speculate that even smaller polyamines with a net charge of ≥3 may also be able to slide on DNA. A lower mw molecular sled might be more advantageous for driving the design of drug-like small molecules toward compatibility with Lipinski's rules.

Altogether, Applicants further investigated the structure-function relationships of sliding activity, and discovered sliding activity from peptide analogs to small molecules. In addition to revealing new ways to independently modulate Kd and D1 values, many of these molecular sleds carry other qualities such as very low molecular weights, cell penetrating and nuclear localization activity or resistance to proteolysis. These qualities could be important when designing molecular sleds for particular applications. Applicants speculate that molecular sleds could open a new vein for many applications such as in speeding up bimolecular reactions, improving the pharmacokinetics of drug molecules, or improving the functionality of synthetic TFs, etc.

Additional references of interest include, reference possibly made thereto in the prior description by superscript:

(1) Blainey, P. C.; van Oijen, A. M.; Banerjee, A.; Verdine, G. L.; Xie, X. S. P Natl Acad Sci USA 2006, 103, 5752.
(2) Etson, C. M.; Hamdan, S. M.; Richardson, C. C.; van Oijen, A. M. P Natl Acad Sci USA 2010, 107, 1900.
(3) Ponferrada-Marin, M. I.; Roldan-Arjona, T.; Ariza, R. R. Nucleic Acids Res 2012, 40, 11554.
(4) Chen, J. J.; Zhang, Z. J.; Li, L.; Chen, B. C.; Revyakin, A.; Hajj, B.; Legant, W.; Dahan, M.; Lionnet, T.; Betzig, E.; Tjian, R.; Liu, Z. Cell 2014, 156, 1274.
(5) Dikic, J.; Menges, C.; Clarke, S.; Kokkinidis, M.; Pingoud, A.; Wende, W.; Desbiolles, P. Nucleic Acids Res 2012, 40, 4064.
(6) Leith, J. S.; Tafvizi, A.; Huang, F.; Uspal, W. E.; Doyle, P. S.; Fersht, A. R.; Mirny, L. A.; van Oijen, A. M. P Natl Acad Sci USA 2012, 109, 16552.
(7) Blainey, P. C.; Luo, G. B.; Kou, S. C.; Mangel, W. F.; Verdine, G. L.; Bagchi, B.; Xie, X. S. Nat Struct Mol Biol 2009, 16, 1224.
(8) Cuculis, L.; Abil, Z.; Zhao, H.; Schroeder, C. M. Nat Commun 2015, 6, 7277.
(9) Mangel, W. F.; McGrath, W. J.; Xiong, K.; Graziano, V.; Blainey, P. C. Nature Communications 2016.
(10) Blainey, P. C.; Graziano, V.; Perez-Berna, A. J.; McGrath, W. J.; Flint, S. J.; Martin, C. S.; Xie, X. S.; Mangel, W. F. J Biol Chem 2013, 288, 2092.
(11) Xiong, K.; Blainey, P. C. Nucleic Acids Res 2016, in press.

(12) Turkin, A.; van Oijen, A. M.; Turkin, A. A. Physical review. E, Statistical, nonlinear, and soft matter physics 2015, 92, 052703.
(13) Turkin, A.; Zhang, L.; Marcozzi, A.; Mangel, W. F.; Herrmann, A.; van Oijen, A. M. Chem Sci 2016, 7, 916.
(14) Ngo, T. A.; Nakata, E.; Saimura, M.; *Morii*, T. J Am Chem Soc 2016.
(15) Slomovic, S.; Collins, J. J. Nat Methods 2015, 12, 1085.
(16) Li, X.; Liu, D. R. Angew. Chem. Int. Ed. 2004, 43, 4848
(17) Gartner, Z. J.; Tse, B. N.; Grubina, R.; Doyon, J. B.; Snyder, T. M.; Liu, D. R. Science 2004, 305, 1601.
(18) Kanan, M. W.; Rozenman, M. M.; Sakurai, K.; Snyder, T. M.; Liu, D. R. Nature 2004, 431, 545.
(19) van Oijen, A. M.; Blainey, P. C.; Crampton, D. J.; Richardson, C. C.; Ellenberger, T.; Xie, X. S. Science 2003, 301, 1235.
(20) Zandarashvili, L.; Esadze, A.; Vuzman, D.; Kemme, C. A.; Levy, Y.; Iwahara, J. P Natl Acad Sci USA 2015, 112, E5142.
(21) Rohs, R.; West, S. M.; Sosinsky, A.; Liu, P.; Mann, R. S.; Honig, B. Nature 2009, 461, 1248.
(22) Gabbay, E. J.; Adawadkar, P. D.; Kapicak, L.; Pearce, S.; Wilson, W. D. Biochemistry 1976, 15, 152.
(23) Ouameur, A. A.; Tajmir-Riahi, H. A. J Biol Chem 2004, 279, 42041.
(24) Wemmer, D. E.; Srivenugopal, K. S.; Reid, B. R.; Morris, D. R. J Mol Biol 1985, 185, 457.
(25) Deng, H.; Bloomfield, V. A.; Benevides, J. M.; Thomas, G. J., Jr. Nucleic Acids Res 2000, 28, 3379.
(26) Dervan, P. B.; Edelson, B. S. Current opinion in structural biology 2003, 13, 284.
(27) Erwin, G. S.; Bhimsaria, D.; Eguchi, A.; Ansari, A. Z. Angew Chem Int Edit 2014, 53, 10124.
(28) Carlson, C. D.; Warren, C. L.; Hauschild, K. E.; Ozers, M. S.; Qadir, N.;
Bhimsaria, D.; Lee, Y.; Cerrina, F.; Ansari, A. Z. P Natl Acad Sci USA 2010, 107, 4544.
(29) Blainey, P. C., Harvard University, 2007.
(30) Puckett, J. W.; Muzikar, K. A.; Tietjen, J.; Warren, C. L.; Ansari, A. Z.; Dervan, P. B. Journal of the American Chemical Society 2007, 129, 12310.

The invention is further described by the following numbered paragraphs:

1. A composition comprising a non-naturally occurring or engineered artificial transcription factor, wherein the transcription factor comprises a sequence specific DNA binding domain, a sliding domain, and one or more linkers, wherein the DNA binding domain and the sliding domain are operably connected by the one or more linkers.
2. The composition of paragraph 1 wherein the DNA binding domain is a transcription factor or a derivative thereof.
3. The composition of paragraph 2, wherein the transcription factor is GCN4 or cMyc.
4. The composition of paragraph 2, wherein the transcription is bZIP.
5. The composition of paragraph 1, wherein the DNA binding domain is a Dervan polyamide minor groove binder.
6. The composition of any one of paragraphs 1-5, wherein the sliding domain is pVIc or a derivative or refinement thereof.
7. The composition of paragraph 6, wherein the pVIc comprises the sequence GVQSLKRRRCF (SEQ ID NO: 1).
8. The composition of paragraph 6, wherein the refined pVIc comprises the sequence KRRR (SEQ ID NO: 2).
9. The composition of any one of paragraphs 1-8, wherein the sliding domain is a p53 C-terminus, HIV tat or a cationic homopolymer.
10. The composition of paragraph 1, wherein the composition comprises the sequence of KRARNTEAARRSRARKGGC-(G)n-KRRR (SEQ ID NO: 3) or NVKRRTHNNVLERQRNELKRSFFALRDQ-(G)n-KRRR (SEQ ID NO: 5).
11. The composition of paragraph 10, wherein the composition comprises the sequence of KRARNTEAARRSS-RAR-AAAAAA-KRRR (SEQ ID NO: 4).
12. The composition of paragraph 1, wherein the composition comprises a synthetic dsDNA binding molecule coupled to (G)n-GVQSLKRRRCF (SEQ ID NO: 6) or (G)n-KRRR (SEQ ID NO: 7).
13. The composition of any one of paragraphs 1-10 or 12 wherein the one or more linkers has a length of about one to about eighteen Angstroms or about the same length from about one to about twelve amino acids long.
14. The composition of paragraph 13, wherein the one or more linkers is poly alanine (4-6 residues) (SEQ ID NO: 28) or poly glycine (4-6 residues) (SEQ ID NO: 29).
15. The composition of paragraph 1 comprising:
    (a) the sliding domain comprising a molecular sled comprising a core sequence of amino acids XZ'ZZZ'X'X" wherein
       X, X' and X" is any amino acid, wherein X, X' or X" are optional
       Z' is any amino acid and is advantageously lysine (K), arginine (R) or histidine (H), wherein Z' is optional and
       Z is any basic residue and is lysine (K), arginine (R) or histidine (H)
    (b) the one or more linkers comprising X, X' and X" or one or more linkers attached to X, X' and/or X" and/or
    (c) molecular cargo linked to the one or more linkers;
       wherein the core sequence of amino acids XZ'ZZZ'X'X" is capable of sliding on a negatively charged polymer track.
16. The composition of paragraph 15, wherein the DNA binding domain comprises the molecular cargo.
17. The composition of paragraph 15 or 16, wherein X is lysine (K).
18. The composition of any one of paragraphs 15-17, wherein X' is cysteine (C).
19. The composition of any one of paragraphs 15-18, wherein X" is phenylalanine (F).
20. The composition of paragraph 15, wherein the core sequence is XKRRRCX" (SEQ ID NO: 8).
21. The composition of paragraph 15, wherein the core sequence is KKRRRCX" (SEQ ID NO: 9).
22. The composition of paragraph 15, wherein the core sequence is XKRRRCF (SEQ ID NO: 10).
23. The composition of paragraph 15, wherein the core sequence is KKRRRCF (SEQ ID NO: 11).
24. The composition of paragraph 15, wherein the core sequence is KRRRCF (SEQ ID NO: 12).
25. The composition of any one of paragraphs 15-24, wherein the composition is capable of penetrating a cell membrane.
26. The composition of any one of paragraphs 15-25 further comprising a nuclear localization signal (NLS).
27. The composition of any one of paragraphs 15-26, wherein X, X' or X" comprises one or more non-naturally occurring amino acids.
28. The composition of any one of paragraphs 15-26, wherein X, X' or X" are naturally occurring amino acids.

29. The composition of any one of paragraphs 1-28, wherein the one or more linkers are attached with a covalent bond, a non-covalent bond and/or a neutrally charged ionic bond.

30. The composition of any one of paragraphs 1-29, wherein the one or more linkers comprises a disulfide bond.

31. The composition of any one of paragraphs 1-30, wherein the one or more linkers has at least 4, at least 5, at least 6, at least 10, at least 20, at least 30, at least 40, at least 50, at least 60, at least 70, at least 80, at least 90, up to about 100 linear or straight-chain or branched carbon, nitrogen, oxygen, phosphorous, and/or sulfur atoms.

32. The composition of any one of paragraphs 1-31, wherein the one or more linkers is an organic linker.

33. The composition of paragraph 32, wherein the organic linker is an amide, carbon-sulfide, ester or ether.

34. The composition of any one of paragraphs 1-33, wherein the one or more linkers is poly(ethylene glycol).

35. The composition of any one of paragraphs 1-34, wherein the one of more linkers comprises a small component.

36. The composition of paragraph 35, wherein the small component is biotin or digoxigenin.

37. The composition of any one of paragraphs 1-36, wherein the one or more linkers is bioconjugated.

38. The composition of any one of paragraphs 1-37, wherein the one of more linkers is a peptide.

39. The composition of paragraph 38, wherein the peptide is an epitope.

40. The composition of paragraph 39, wherein the epitope is recognized by a FLAG or HISS antibody.

41. The composition of any one of paragraphs 15-40, wherein the cargo is naturally occurring.

42. The composition of any one of paragraphs 15-41, wherein the molecular cargo is a therapeutic agent.

43. The composition of any one of paragraphs 15-42, wherein the molecular cargo is a small molecule, a nucleic acid, a peptide, a protein or an analog or derivative thereof.

44. The composition of paragraph 43, wherein the small molecule is a drug.

45. The composition of paragraph 43, wherein the nucleic acid is a double stranded DNA, single stranded DNA or RNA.

46. The composition of paragraph 43 wherein the nucleic acid contains a residue with a 2' O-Me, LNA, or a minor-grove-binding moiety modification.

47. The composition of paragraph 43, wherein the protein is an antibody.

48. The composition of paragraph 47, wherein the antibody targets a nucleic acid binding protein.

49. The composition of paragraph 43, wherein the protein is Gemifloxacin or Norfloxacin.

50. The composition of paragraph 43, wherein the protein is a nucleic acid binding protein.

51. The composition of paragraph 50, wherein the nucleic acid binding protein binds a specific sequence.

52. The composition of paragraph 50 or 51, wherein the nucleic acid binding protein is a DNA gyrase, a transcription activator-like effector (TALE) DNA binding protein, a transcription factor, a zinc finger binding protein or a CRISPR-Cas complex.

53. The composition of paragraph 43, wherein the protein is an adenovirus proteinase (AVP), protein VI, pVI, or streptavidin.

54. The composition of any one of paragraphs 1-53, wherein the composition is chemically modified with one or more gyrase inhibitors.

55. The composition of any one of paragraphs 1-54 further comprising a molecular capsule.

56. The composition of paragraph 55, wherein the molecular capsule is a calixarene, cucurbituril, cyclodextrin or pillararene.

57. The composition of paragraph 56, wherein the cucurbituril comprises 5, 6, 7, 8 or 10 repeat units.

58. The composition of any one of paragraphs 15-57, wherein the cargo is a particle.

59. The composition of paragraph 58, wherein the particle is a nanoparticle, a bead, an organelle or a large protein complex.

60. The composition of any one of paragraphs 1-59, further comprising a label.

61. The composition of paragraph 60, wherein the label is a fluorescent label.

62. The composition of paragraph 61, wherein the fluorescent label is a perylene or a terrylen.

63. The composition of any one of paragraphs 15-62, wherein the molecular cargo is covalently linked to the one or more linkers.

64. The composition of any one of paragraphs 15-63 wherein the molecular cargo hydrogen bonds with the one or more linkers.

65. The composition of any one of paragraphs 1-64, wherein the one or more linkers and/or molecular cargo is light sensitive, wherein the molecular cargo is light-activated and/or light cleaves the one or more linkers to release the molecular cargo.

66. The composition of paragraph 65, wherein the light-activated molecular cargo is a major light-harvesting complex (LHCII).

67. The composition of any one of paragraphs 61-66, wherein the fluorescent label induces free radical formation.

68. The composition of any one of paragraphs 1-67, wherein the composition is displayed on an exterior bacterial cell surface.

69. The composition of any one of paragraphs 1-68, wherein the composition is displayed on an inner bacterial cell surface.

70. A nucleic acid encoding the composition of any one of paragraphs 1-69, wherein the one or more linkers is a DNA, peptide or protein linker.

71. The nucleic acid of paragraph 70, wherein the expression of the composition is inducible.

72. A virus particle comprising the nucleic acid of paragraph 70 or 71.

73. A diagnostic method for detecting cancer, a degenerative disease, a genetic disease or an infectious disease comprising targeting a composition according to any one of paragraphs 15-72 to a suspected cancer cell, genetically diseased cell or infected cell and detecting the molecular sled in the suspected cancer cell or infected cell, thereby detecting cancer, a genetic disease or an infectious disease.

74. The method of paragraph 73, wherein the targeting is to a marker specific to a cancer cell, genetically diseased cell or infected cell, wherein the targeting is by attachment to cargo of a particular size, by attachment via a pH-sensitive cleavable linker, or by a cargo with molecular recognition capability to target cancer biomarker or a singular cargo or a second, additional cargo.

75. A method for reducing the required dosage of an antibiotic comprising chemically attaching the composition of any one of paragraphs 1-74 to the antibiotic.

76. The method of paragraph 75, wherein the antibiotic is a gyrase or a topoisomerase inhibitor.

77. The method of paragraph 76, wherein the gyrase or topoisomerase inhibitor is gemifloxacin.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

---

What is claimed is:

1. A composition comprising a non-naturally occurring or engineered artificial transcription factor, wherein the transcription factor comprises a sequence specific DNA binding domain comprising KRARNTEAARRSRAR (SEQ ID NO: 20), a sliding domain comprising KRRR (SEQ ID NO: 2), and one or more linkers, wherein the DNA binding domain and the sliding domain are operably connected by the one or more linkers.

2. The composition of claim 1, wherein the composition comprises a sequence selected from the group consisting of KRARNTEAARRSRAR-GSGSGS-KRRR (SEQ ID NO: 17) and KRARNTEAARRSRAR-GSGSGS-GVQS-LKRRRCF (SEQ ID NO: 53).

3. The composition of claim 1, wherein the one or more linkers has a length of one to eighteen Angstroms.

4. The composition of claim 1, wherein the one or more linkers has a length of one to twelve amino acids.

5. The composition of claim 1, wherein the one or more linkers is selected from the group consisting of poly alanine (4-6 residues) (SEQ ID NO: 28) and poly glycine (4-6 residues) (SEQ ID NO: 29).

6. The composition of claim 1, further comprising a cargo linked to an amino acid residue of the artificial transcription factor.

7. The composition of claim 6, wherein the cargo is attached to the artificial transcription factor at a site selected from the group consisting of the DNA binding domain and the one or more linkers.

8. The composition of claim 6, wherein the cargo is attached to the DNA binding domain.

9. The composition of claim 6, wherein the cargo is a therapeutic agent.

10. The composition of claim 6, wherein the cargo is selected from the group consisting of a small molecule, a nucleic acid, a peptide, and an analog or derivative thereof.

11. The composition of claim 10, wherein the small molecule is a drug.

12. The composition of claim 6, wherein the cargo is naturally occurring.

13. The composition of claim 6, wherein the artificial transcription factor or the cargo comprises a nuclear localization signal (NLS).

14. The composition of claim 6, wherein the composition is capable of penetrating a cell membrane.

15. The composition of claim 10, wherein the peptide is an antibody.

16. The composition of claim 15, wherein the antibody targets a nucleic acid binding protein.

17. The composition of claim 10, wherein the peptide is a nucleic acid binding protein.

18. The composition of claim 17, wherein the nucleic acid binding protein is selected from the group consisting of a DNA gyrase, a transcription activator-like effector (TALE) DNA binding protein, a transcription factor, a zinc finger binding protein and a CRISPR-Cas complex.

19. The composition of claim 10, wherein the peptide is selected from the group consisting of Gemifloxacin, Norfloxacin, an adenovirus proteinase (AVP), protein VI, pVI, and streptavidin.

20. The composition of claim 10, wherein the nucleic acid is selected from the group consisting of a double stranded DNA, a single stranded DNA and a RNA.

21. The composition of claim 20, wherein the nucleic acid contains a residue with a modification selected from the group consisting of a 2' 0-Me, a locked nucleic acid (LNA), and a minor-grove-binding moiety modification.

22. The composition of claim 6, wherein the cargo is a particle.

23. The composition of claim 22, wherein the particle is selected from the group consisting of a nanoparticle, a bead, an organelle and a large protein complex.

24. The composition of claim 6, wherein the cargo is light-activated.

25. The composition of claim 24, wherein the light-activated cargo is a major light-harvesting complex (LHCII).

26. The composition of claim 6, wherein light cleaves the one or more linkers to release the cargo.

27. The composition of claim 1, further comprising a fluorescent label.

28. The composition of claim 27, wherein the fluorescent label is selected from the group consisting of a perylene and a terrylen.

29. The composition of claim 27, wherein the fluorescent label induces free radical formation.

30. A capsule comprising the composition of claim 1 encapsulated by a molecular capsule.

31. The capsule of claim 30, wherein the molecular capsule is selected from the group consisting of a calixarene, a cucurbituril, a cyclodextrin and a pillararene.

32. The capsule of claim 31, wherein the cucurbituril comprises 5, 6, 7, 8 or 10 repeat units.

* * * * *